US009988620B2

(12) United States Patent
Crine et al.

(10) Patent No.: US 9,988,620 B2
(45) Date of Patent: Jun. 5, 2018

(54) METHODS, COMPOSITIONS, AND KITS FOR THE TREATMENT OF MATRIX MINERALIZATION DISORDERS

(75) Inventors: Philippe Crine, Outremont (CA); Pierre Leonard, Montreal (CA)

(73) Assignee: Alexion Pharmaceuticals, Inc., New Haven, CT (US)

( * ) Notice: Subject to any disclaimer, the term of this patent is extended or adjusted under 35 U.S.C. 154(b) by 1136 days.

(21) Appl. No.: 13/695,127

(22) PCT Filed: Apr. 29, 2011

(86) PCT No.: PCT/CA2011/050258
§ 371 (c)(1),
(2), (4) Date: Jan. 14, 2013

(87) PCT Pub. No.: WO2011/134084
PCT Pub. Date: Nov. 3, 2011

(65) Prior Publication Data
US 2013/0108635 A1  May 2, 2013

Related U.S. Application Data

(60) Provisional application No. 61/329,877, filed on Apr. 30, 2010.

(51) Int. Cl.
C12N 9/96 (2006.01)
A61K 31/7088 (2006.01)
A61K 38/46 (2006.01)
A61K 47/68 (2017.01)

(52) U.S. Cl.
CPC ............ *C12N 9/96* (2013.01); *A61K 31/7088* (2013.01); *A61K 38/465* (2013.01); *A61K 47/6811* (2017.08)

(58) Field of Classification Search
None
See application file for complete search history.

(56) References Cited

U.S. PATENT DOCUMENTS

| | | | |
|---|---|---|---|
| 6,290,952 B1 | 9/2001 | Poelstra et al. | |
| 6,420,384 B2 | 7/2002 | Weigele et al. | |
| 6,436,386 B1 | 8/2002 | Roberts et al. | |
| 6,455,495 B1 | 9/2002 | Orgel et al. | |
| 6,458,579 B2 | 10/2002 | Hopwood et al. | |
| 6,905,689 B2 | 6/2005 | Schneidinger et al. | |
| 7,179,903 B2 | 2/2007 | McArthur et al. | |
| 7,399,466 B2 | 7/2008 | Boileau | |
| 7,625,564 B2 | 12/2009 | Wang et al. | |
| 7,763,712 B2 | 7/2010 | Crine et al. | |
| 7,803,769 B2 | 9/2010 | Sullivan et al. | |
| 7,943,126 B2 | 5/2011 | Tomatsu et al. | |
| 7,960,529 B2 | 6/2011 | Crine et al. | |
| 2002/0183276 A1 | 12/2002 | Millan et al. | |
| 2003/0158132 A1 | 8/2003 | Kovesdi | |
| 2004/0023916 A1 | 2/2004 | Millan et al. | |
| 2004/0234518 A1 | 11/2004 | Crine et al. | |
| 2005/0276796 A1 | 12/2005 | Tomatsu et al. | |
| 2006/0014687 A1 | 1/2006 | Crine et al. | |
| 2007/0041972 A1 | 2/2007 | Rother et al. | |
| 2007/0042957 A1 | 2/2007 | Burnett et al. | |
| 2007/0081984 A1 | 4/2007 | Tomatsu et al. | |
| 2007/0081986 A1 | 4/2007 | Tomatsu et al. | |
| 2008/0085862 A1 | 4/2008 | Kim et al. | |
| 2008/0181903 A1 | 7/2008 | Bhaskar et al. | |
| 2009/0053192 A1 | 2/2009 | Millan et al. | |
| 2009/0069243 A1 | 3/2009 | Burnett, Jr. et al. | |
| 2009/0142347 A1 | 6/2009 | Millan | |
| 2009/0238814 A1 | 9/2009 | Tomatsu et al. | |
| 2010/0008979 A1 | 1/2010 | Tomatsu et al. | |
| 2010/0184680 A1 | 7/2010 | Bevec | |
| 2010/0221234 A1 | 9/2010 | Crine et al. | |
| 2010/0240125 A1 | 9/2010 | Crine et al. | |
| 2010/0297119 A1 | 11/2010 | Crine et al. | |
| 2011/0250187 A1 | 10/2011 | Tomatsu et al. | |

FOREIGN PATENT DOCUMENTS

| | | |
|---|---|---|
| JP | 8070875 | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-530222 A | 9/2010 |
| WO | WO-92/020371 A1 | 11/1992 |
| WO | WO-98/35703 A2 | 8/1998 |
| WO | WO-00/18954 A2 | 4/2000 |

(Continued)

OTHER PUBLICATIONS

Orimo (J. Nippon Med Sch 2010, 77(1):4-12).*
Attwood (Science 290: 471-473, 2000).*
Skolnick et al. (Trends in Biotech. 18: 34-39, 2000).*
NCBI Protein Database Accession No. Q6PYX1. Retrieved on Oct. 15, 2013 (2 pages).
Oikawa et al., "Enzyme replacement theory on hypophosphatasia mouse model," J Inherit Metab Dis. 1-9(2013).
Official Notification and Search Report for Eurasian Patent Application No. 201291138, dated May 17, 2013 (3 pages).
Achord et al., "Human β-glucuronidase: In vivo clearance and in vitro uptake by a glycoprotein recognition system on reticuloendothelial cells," *Cell* 15:269-278 (1978).
Addison et al., "Pyrophosphate inhibits mineralization of osteoblast cultures by binding to mineral, up-regulating osteopontin, and inhibiting alkaline phosphate activity," *Biol Chem.* 282:15872-15883 (2007).

(Continued)

*Primary Examiner* — Sharon X Wen
(74) *Attorney, Agent, or Firm* — Clark & Elbing LLP

(57) ABSTRACT

The present invention provides methods, compositions, and kits for the treatment of matrix mineralization disorders such as hypophosphatasia. In particular, the present invention provides polypeptides having a soluble alkaline phosphatase fused to an Fc domain of an immunoglobulin. Such polypeptides can be administered to patients, e.g., subcutaneously, to treat hypophosphatasia using enzyme replacement therapy. The invention also features nucleic acids encoding such polypeptides and the use of the nucleic acids for treating matrix mineralization disorders.

31 Claims, 17 Drawing Sheets

(56) References Cited

FOREIGN PATENT DOCUMENTS

| WO | WO-00/050580 A2 | 8/2000 |
|---|---|---|
| WO | WO-00/64486 A2 | 11/2000 |
| WO | WO-01/36620 A2 | 5/2001 |
| WO | WO-02/015918 A2 | 2/2002 |
| WO | WO-02/068579 A2 | 9/2002 |
| WO | WO-2005/007809 A2 | 1/2005 |
| WO | WO-2005/042034 A1 | 5/2005 |
| WO | WO-2005/103263 A1 | 11/2005 |
| WO | WO-2006/039480 A2 | 4/2006 |
| WO | WO-2006/060641 A2 | 6/2006 |
| WO | WO-2008/053362 A2 | 5/2008 |
| WO | WO-2008/088422 A2 | 7/2008 |
| WO | WO-2008/138131 A1 | 11/2008 |
| WO | WO-2008/154226 A1 | 12/2008 |
| WO | WO-2009/158035 A2 | 12/2009 |
| WO | WO-2010/135541 A2 | 11/2010 |
| WO | WO-2011/134084 A1 | 11/2011 |
| WO | WO-2012/099851 A2 | 7/2012 |

OTHER PUBLICATIONS

Ali et al., "Isolation and characterization of calcifying matrix vesicles from epiphyseal cartilage," *Proc Natl Acad Sci USA* 67(3):1513-1520 (1970).

Altarescu et al., "The efficacy of enzyme replacement therapy in patients with chronic neuronopathic Gaucher's disease," *J Pediatr.* 168(4):539-547 (2001).

Anderson et al., "Pyrophosphate stimulation of calcium uptake into cultured embryonic bones. Fine structure of matrix vesicles and their role in calcification," *Dev Biol.* 34:211-227 (1973).

Anderson et al., "Impaired calcification around matrix vesicles of growth plate and bone in alkaline phosphatase-deficient mice," *Am J Pathol.* 164:841-847 (2004).

Anderson et al., "Matrix vesicles in osteomalacic hypophosphatasia bone contain apatite-like mineral crystals," *Am J Pathol.* 151:1555-1561 (1997).

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," *Am J Pathol.* 166(6):1711-1720 (2005).

Anderson et al., "The role of matrix vesicles in growth plate development and biomineralization," *Front Biosci.* 10:822-837 (2005).

Barranger et al., "Lessons learned from the development of enzyme therapy for Gaucher disease," *J Inherit Metab Dis.* 24(Supp 2):89-96 (2001).

Barton et al., "Replacement therapy for inherited enzyme deficiency—macrophage-targeted glucocerebrosidase for Gaucher's disease," *N. Engl J Med.* 324:1464-1470 (1991) (Abstract only).

Beertsen et al., "Root development in mice lacking functional tissue non-specific alkaline phosphatase gene: Inhibition of acellular cementum formation," *J Dent Res.* 78(6):1221-1229 (1999).

Bennett et al., "Extracellular domain-IgG fusion proteins for three human natriuretic peptide receptors," *J Biol Chem.* 266(34):23060-23067 (1991).

Bernardi et al., "Chromatography of proteins on hydoxyapatite," *Methods in Enzymology* 27:471-479 (1973).

Bernard, "Ultrastructural localization of alkaline phosphatase in initial intramembranous osteogenesis," *Clin Orthop Relat Res.* 135:218-225 (1978).

Bobé et al., "Fas-mediated liver damage in MRL hemopoietic chimeras undergoing Ipr-mediated graft-versus-host disease," *J Immunol.* 159:4197-4204 (1997).

Bonilla, "Pharmacokinetics of immunoglobulin administered via intravenous or subcutaneous routes," *Immunol Allergy Clin N Am.* 28:803-819 (2008).

Boskey, "Amorphous calcium phosphate: The contention of bone," *J Dent Res.* 76:1433-1436 (1997).

Boskey et al. "Matrix vesicles promote mineralization in a gelatin gel," *Calcif Tissue Int.* 60:309-315 (1997).

Byers et al., "Effect of enzyme replacement therapy on bone formation in a feline model of mucopolysaccharidosis type VI," *Bone* 21(5):425-431 (1997).

Cameron et al., "Minireview: natriuretic peptides during development of the fetal heart and circulation," *Endocrinology* 144(6):2191-2194 (2003).

Campbell et al., "Insulin-like growth factor (IGF)-binding protein-5-(201-218) region regulates hydroxyapatite and IGF-I binding," *Am J Physiol.* 273:E1005-1013 (1997).

Ciancaglini et al., "Contribution of matrix vesicles and alkaline phosphatase to ectopic bone formation," *Braz J Med Biol. Res.* 39:603-610 (2006).

Cleland et al., "Emerging protein delivery methods," *Curr Opin Biotechnol.* 12:212-219 (2001).

Clemens et al., "Pharmacokinetics and biological actions of subcutaneously administered human brain natriuretic peptide," *J Pharmacol Exp Ther.* 287:67-71 (1998).

Crawley et al., "Enzyme replacement therapy in a feline model of Maroteaux-Lamy Syndrome," *J Clin Invest.* 97:1864-1873 (1996).

Data Sheet for pFUSE-Seap-hFC: Plasmid designed for the expression of a SEAP-Fc Fusion protein, Invivogen, San Diego, CA (4 pages) (1989).

Di Mauro et al., "Kinetic characterization of hypophosphatasia mutations with physiological substrates," *J Bone Miner Res.* 17(8):1383-1391 (2002).

Dumont et al., "Monomeric Fc fusions: Impact on pharmacokinetic and biological activity of protein therapeutics," *BioDrugs* 20(3):151-160 (2006).

Engel et al., "Characterization of the hormone binding site of natriuretic peptide receptor-C," *FEBS Lett.* 360:169-172 (1995).

Eng et al., "Safety and efficacy of recombinant human α-Galactosidase a replacement therapy in Fabry's Disease," *N Engl J Med.* 345:9-16 (2001).

Farley et al., "Effects of tunicamycin, mannosamine, and other inhibitors of glycoprotein processing on skeletal alkaline phosphatase in human osteoblast-like cells," *Calcif Tissue Int.* 76:63-74 (2005).

Fedde et al., "Alkaline phosphatase knock-out mice recapitulate the metabolic and skeletal defects of infantile hypophosphatasia," *J Bone Miner Res.* 14(12):2015-2026 (1999).

Fujisaki et al., "Osteotropic Drug Delivery System (ODDS) based on bisphosphonic prodrug. IV effects of osteotropic estradiol on bone mineral density and uterine weight in ovariectomized rats," *J Drug Target* 5:129-138 (1997).

Fujisawa et al., "Acidic amino acid-rich sequences as binding sites of osteonectin to hydroxyapatite crystals," *Biochim Biophys Acta.* 1292:53-60 (1996).

Furbish et al., "Uptake and distribution of placental glucocerebrosidase in rat hepatic cells and effects of sequential deglycosylation," *Biochim Biophys Acta.* 673:425-434 (1981).

Garg, *Investigation of the role of FcRn in the absorption, distribution, and elimination of monoclonal antibodies.* Dissertation: State University of New York at Buffalo (2007) (Abstract only, 2 pages).

Gilbert et al., "Chimeric peptides of statherin and osteopontin that bind hydroxyapatite and mediate cell adhesion," *J Biol Chem.* 275:16213-16218 (2000).

Greenberg et al., "A homoallelic Gly[317]→Asp mutation in ALPL causes the perinatal (lethal) form of hypophosphatasia in Canadian mennonites," *Genomics* 17:215-217 (1993).

Guo et al., "Protein tolerance to random amino acid change," *Proc Natl Acad Sci U S A.* 101(25):9205-9210 (2004).

Halling Linder et al., "Glycosylation differences contribute to distinct catalytic properties among bone alkaline phosphotase isoforms," *Bone* 45:987-993 (2009).

Hardy et al., "Dissection of a carboxy-terminal region of the yeast regulatory protein RAP1 with effects on both transcriptional activation and silencing," *Mol Cell Biol.* 12(3):1209-1217 (1992).

Harmey et al., "Concerted regulation of inorganic pyrophosphate and osteopontin by Akp2, Enppl , and Ank," *Am J Pathol.* 164(4):1199-1209 (2004).

(56) References Cited

OTHER PUBLICATIONS

Harmey et al., "Elevated skeletal osteopontin levels contribute to the hypophosphatasia phenotype in Akp2$^{-/-}$ mice," *J Bone Miner Res.* 21(9):1377-1386 (2006).

Hawrylak et al., "The solubilization of tetrameric alkaline phosphatase from human liver and its conversion into various forms by phosphatidylinositol phospholipase C or proteolysis," *J Biol Chem.* 263(28):14368-14373 (1988).

Henthorn et al., "Missense mutations of the tissue non-specific alkaline phosphatase gene in hypophosphatasia," *Clin Chem.* 38:2501-2505 (1992).

Henthorn et al., "Different missense mutations at the tissue-non-specific alkaline phosphatase gene locus in autosomal recessively inherited forms of mild and severe hypophosphatasia," *Proc Natl Acad Sci USA* 89:9924-9928 (1992).

Hessle et al., "Tissue-nonspecific alkaline phosphatase and plasma cell membrane glucoprotein-1 are central antagonistic regulators of bone mineralization," *Proc Natl Acad Sci USA* 99(14): 9445-9449 (2002).

Hosain et al., "Targeted delivery of antineoplastic agent to bone: Biodistribution studies of technetium-99m-labeled gem-bisphosphonate conjugate of methotrexate," *J Nucl Med.* 37:105-107 (1996).

Hult et al., "Engineered enzymes for improved organic synthesis," *Curr Opin Biotechnol.* 14:395-400 (2003).

Hunter et al., "Modulation of crystal formation by bone phosphoproteins: Structural specificity of the osteopontin-mediated inhibition of hydroxyapatite formation," *Biochem J.* 300:723-728 (1994).

Ikezawa, "Glycosylphosphatidylinositol (GPI)-anchored proteins," *Biol Pharm Bull.* 25(4):409-417 (2002).

Jansonius, "Structure, evolution and action of vitamin B$_6$-dependent enzymes," *Curr Opin Struct Biol.* 8:759-769 (1998).

Jin et al., "Novel analog of atrial natriuretic peptide selective for receptor-A produces increased diuresis and natriuresis in rats," *J Clin Invest.* 98(4):969-976 (1996).

Johnson et al., "Matrix vesicle plasma cell membrane glycoprotein-1 regulates mineralization by murine osteoblastic MC3T3 cells," *J Bone Miner Res.* 14(6):883-892 (1999).

Kakkis et al., "Enzyme-replacement therapy in mucopolysaccharidosis I," *N Engl J Med.* 344(3):182-188 (2001).

Kasugai et al., "Selective drug delivery system to bone: Small peptide (Asp)$_6$ conjugation," *J Bone Miner Res.* 15(5):936-943 (2000).

Kaufmann et al., "Influence of low temperature on productivity, proteome and protein phosphorylation of CHO cells," *Biotechnol Bioeng.* 63:573-582 (1999).

Kochendoerfer, "Protein & peptide drug delivery—third international conference: Minimally invasive delivery methods," *IDrugs* 6(11): 1043-1045 (2003).

Kostenuik et al., "Infrequent delivery of a long-acting PTH-Fc fusion protein has potent anabolic effects on cortical and cancellous bone," *J Bone Miner Res.* 22(10):1534-1547 (2007).

Leone et al., "Allosteric modulation of pyrophosphatase activity of rat osseous plate alkaline phosphatase by magnesium ions," *Int J Biochem Cell Biol.* 30:89-97 (1998).

Mahmood et al., "Selection of the first-time dose in humans: Comparison of different approaches based on interspecies scaling of clearance," *J Clin Pharmacol.* 43:692-697 (2003).

Meyer, "Can biological calcification occur in the presence of pyrophosphate?" *Arch Biochem Biophys.* 231:1-8 (1984).

Michigami et al., "Common mutations F310L and T1559del in the tissue-nonspecific alkaline phosphatase gene are related to distinct phenotypes in Japanese patients with hypophosphatasia," *Eur J Pediatr.* 164:277-282 (2005).

Milián et al., "Enzyme Replacement Therapy for Murine Hypophosphatasia." *J. Bone Miner. Res.* 23: 777-787 (2008) (Epublished ahead of print on Dec. 17, 2007).

Milián, "Mammalian Alkaline Phosphatases," Wiley-WCH Verlag GmbH & Co., Weinheim, Germany (2006) (322 pages).

Morris et al., "Immunolocalization of alkaline phosphatase in osteoblasts and matrix vesicles of human fetal bone," *Bone Miner.* 19:287-298 (1992).

Moss et al., "Association of inorganic-pyrophosphatase activity with human alkaline-phosphatase preparations," *Biochem J.* 102:53-57 (1967).

Murray, "Lectin-specific targeting of lysosomal enzymes to reticuloendothelial cells," *Methods Enzymol.* 149:25-42 (1987).

Murshed et al., "Unique coexpression in osteoblasts of broadly expressed genes accounts for the spatial restriction of ECM mineralization to bone," *Genes Dev.* 19:1093-1104 (2005).

Narisawa et al., "Abnormal vitamin B6 etabolism in alkaline phosphatase knock-out mice causes multiple abnormalities, but not the impaired bone mineralization,"*J Pathol.* 193:125-133 (2001).

Narisawa et al., "Inactivation of Two Mouse Alkaline Phosphatase Genes and Establishment of a Model of Infantile Hypophosphatasia," *Dev. Dyn.* 208:432-446 (1997).

Nasu et al., "Aberrant interchain disulfide bridge of tissue-nonspecific alkaline phosphatase with an Arg433 → Cys substitution associated with severe hypophosphatasia," *FEBS Journal* 273:5612-5624 (2006).

NCBI Protein Database Accession No. AAF64516, downloaded on Apr. 16, 2013.

NCBI Protein Database Accession No. AAC33858, downloaded on Apr. 16, 2013.

NCBI Protein Database Accession No. AAH21289, downloaded on Apr. 16, 2013.

NCBI Protein Database Accession No. AAH66116, downloaded on Apr. 16, 2013.

NCBI Protein Database Accession No. AAH90861, downloaded on Apr. 16, 2013.

NCBI Protein Database Accession No. AAI10910, downloaded on Apr. 16, 2013.

NCBI Protein Database Accession No. AAI18209, downloaded on Apr. 16, 2013.

NCBI Protein Database Accession No. AAI26166, downloaded on Apr. 16, 2013.

NCBI Protein Database Accession No. AAN64273, downloaded on Apr. 16, 2013.

NCBI Protein Database Accession No. NP_000469, downloaded on Apr. 16, 2013.

NCBI Protein Database Accession No. NP_001036028, downloaded on Apr. 16, 2013.

NCBI Protein Database Accession No. NP_001253798, downloaded on Apr. 17, 2013.

NCBI Protein Database Accession No. NP_001622, downloaded on Apr. 16, 2013.

NCBI Protein Database Accession No. NP_001623, downloaded on Apr. 16, 2013.

NCBI Protein Database Accession No. NP_031457, downloaded on Apr. 16, 2013.

NCBI Protein Database Accession No. NP_037191, downloaded on Apr. 16, 2013.

NCBI Protein Database Accession No. NP_112603, downloaded on Apr. 16, 2013.

NCBI Protein Database Accession No. NP_776412, downloaded on Apr. 17, 2013.

NCBI Protein Database Accession No. NP_789828, downloaded on Apr. 16, 2013.

NCBI Protein Database Accession No. P01857, downloaded on Apr. 18, 2013.

NCBI Protein Database Accession No. P05186, downloaded on Apr. 16, 2013.

NCBI Protein Database Accession No. P05187, downloaded on Apr. 16, 2013.

NCBI Protein Database Accession No. P08289, downloaded on Apr. 16, 2013.

NCBI Protein Database Accession No. P09242, downloaded on Apr. 16, 2013.

NCBI Protein Database Accession No. P09487, downloaded on Apr. 16, 2013.

NCBI Protein Database Accession No. P09923, downloaded on Apr. 16, 2013.

(56) References Cited

OTHER PUBLICATIONS

NCBI Protein Database Accession No. P10696, downloaded on Apr. 16, 2013.
NCBI Protein Database Accession No. Q29486, downloaded on Apr. 16, 2013.
NCBI Protein Database Accession No. Q9NOVO, downloaded on Apr. 16, 2013.
NCBI Protein Database Accession No. XP-001109717, downloaded on Apr. 17, 2013.
Nishioka et al., "Enhancement of drug delivery to bone: characterization of human tissue-nonspecific alkaline phosphatase tagged with an acidic oligopeptide," *Mol Genet Metab.* 88:244-255 (2006).
Ngo et al., Computational Complexity, Protein Structure Prediction, and the Levinthal Paradox. *The Protein Folding Problem and Tertiary Structure Prediction*. Merz et al. (ed.), 433 and 492-495 (1994).
Nosjean et al., "Human tissue non-specific alkaline phosphatases: sugar-moiety-induced enzymic and antigenic modulations and genetic aspects," *Biochem J.* 321:297-303 (1997).
Oda et al., "A general method for rapid purification of soluble versions of glycosylphosphatidylinositol-anchored proteins expressed in insect cells: an application for human tissue-nonspecific alkaline phosphatase," *J Biochem.* 126:694-699 (1999).
Patti et al., "Critical residues in the ligand-binding site of the *Staphylococcus aureus* collagen-binding adhesin (MSCRAMM)," *J Biol Chem.* 270:12005-12011 (1995).
Pedersen et al., "Removal of N-terminal polyhistidine tags from recombinant proteins using engineered aminopeptidases," *Prot Expr Putifi.* 15:389-400 (1999).
Ramachandran et al., "Treatment of an anabolic bone deficiency in neurofibromatosis with bone morphogenetic proteins and its potential application for congenital pseudarthrosis of the tibia," *J Bone Joint Surg Br.* 91-B (Suppl. 1): Abstract 137 (2009).
Rezende et al., "Inorganic pyrophosphate-phosphohydrolytic activity associated with rat osseous plate alkaline phosphatase," *Cell Mol Biol.* (*Noisy-le-grand*) 44:293-302 (1998).
Rowe et al., "MEPE, A new gene expressed in bone marrow and tumors causing osteomalacia," *Genomics* 67:54-68 (2000).
Russell et al., "Inorganic pyrophosphate in plasma in normal persons and in patients with hypophosphatasia, osteogenesis imperfecta, and other disorders of bone," *J Clin Invest.* 50:961-969 (1971).
Salih et al., "Identification of the phosphorylated sites of metabolically $_{32}$P-labeled osteopontin from cultured chicken osteoblasts," *J Biol Chem.* 272:13966-13973 (1997).
Sands et al., "Enzyme replacement therapy for murine mucopolysaccharidosis type VII," *J Clin Invest.* 93:2324-2331 (1994).
Sekido et al., "Novel drug delivery system to bone using acidic oligopeptide: pharmacokinetic characteristics and pharmacological potential," *J Drug Target.* 9:111-121 (2000).
Sharom et al., "Glycosylphosphatidylinositol-anchored proteins: structure, function, and cleavage by phosphatidylinositol-specific phospholipase C," *Biochem Cell Biol.* 8:535-549 (2002).
Shull et al., "Enzyme replacement in a canine model of hurler syndrome," *Proc Natl Acad Sci. USA* 91:12937-12941 (1994).
Spears et al., "Deoxyuridylate effects on thymidylate synthase-5-fluorodeoxyuridylate-folate ternary complex formation," *Biochem Pharmacol.* 38:2985-2993 (1989).
Srinivas et al., "Assessment of dose proportionality, absolute bioavailability, and immunogenicity response of CTLA4lg (BMS-188667), a novel immunosuppressive agent, following subcutaneous and intravenous administration to rats," *Pharmaceutical Res.* 14(7):911-916 (1997).
Stahl et al., "Evidence for receptor-mediated binding of glycoproteins, glycoconjugates, and lysosomal glycosidases by alveolar macrophages," *Proc Natl Acad Sci USA* 75(3):1399-1403 (1978).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," *Eur J Med Chemistry* 27:825-833 (1992).
Symersky et al., "Structure of the collagen-binding domain from a *Staphylococcus aureus* adhesin," *Nat Struct Biol.* 4(10):833-838 (1997).
Tye et al., "Delineation of the hydroxyapatite-nucleating domains of bone sialoprotein," *J Biol Chem.* 278(10):7949-7955 (2003).
Uludag et al., "Bone affinity of a bisphosphonate-conjugated protein in vivo," *Biotechnol Prog.* 16:1115-1118 (2000).
Urlaub et al., "Deletion of the diploid dihydrofolate reductase locus from cultured mammalian cells," *Cell* 33:405-412 (1983).
Wang et al., "A mouse model for achondroplasia produced by targeting fibroblast growth factor receptor 3," *Proc Natl Acad Sci USA* 96:4455-4460 (1999).
Wang et al., "Structure-based chemical modification strategy for enzyme replacement treatment of phenylketonuria," *Mol Genet Metab.* 86:134-140 (2005).
Waymire et al., "Mice lacking tissue non-specific alkaline phosphatase die from seizures due to defective metabolism of vitamin B-6," *Nat Genet.* 11:45-51 (1995).
Weinberg, "An overview of infliximab, etanercept, efalizumab, and alefacept as biologic therapy for psoriasis," *Clin Ther.* 25:2487-2505 (2003).
Weiss et al., "A missense mutation in the human liver/bone/kidney alkaline phosphatase gene causing a lethal form of hypophosphatasia," *Proc Natl Acad Sci USA* 85:7666-7669 (1988).
Weiss et al., "Isolation and characterization of a cDNA encoding a human liver/bone/kidney-type alkaline phosphatase," *Proc Natl Acad Sci USA* 83:7182-7186 (1986).
Weiss et al., "Structure of the human liver/bone/kidney alkaline phosphatase gene," *J Biol Chem.* 263:12002-12010 (1988).
Weninger et al., "Biochemical and morphological effects of human hepatic alkaline phosphatase in a neonate with hypophosphatasia," *Acta Paediatr Scand.* Suppl. 360:154-160 (1989).
Whyte et al., "Alkaline phosphatase: placental and tissue non-specific isoenzymes hydrolyze phosphoethanolamine, inorganic pyrophosphate, and pyridoxal 5'-phosphate," *J Clin Invest.* 95:1440-1445 (1995).
Whyte et al., "Enzyme replacement therapy for infantile hypophosphatasia attempted by intravenous infusions of alkaline phosphatase-rich Paget plasma: Results in three additional patients," *J Pediatr.* 105(6):926-933 (1984).
Whyte et al., "Enzyme-replacement therapy in life-threatening hypophosphatasia," *N Engl J Med.* 366(10):904-913 (2012).
Whyte et al., "Infantile hypophosphatasia: enzyme replacement therapy by intravenous infusion of alkaline phosphatase-rich plasma from patients with Paget bone disease," *J. Pediatr.* 101:379-386 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," *J Pediatr.* 108(1):82-88 (1986).
Whyte et al., Heritable forms of rickets and osteomalacia. *Connective Tissues and Its Heritable Disorders*, Royce and Steinmann, Wiley-Liss, 765-787 (2002).
Whyte, "Hypophosphatasia," in *The Metabolic and Molecular Bases of Inherited Disease* (*8th ed.*), pp. 5313-5329 (2001) (McGraw-Hill Book Company) (epub pp. 1-41).
Whyte et al., "Markedly increased circulating pyridoxal-5'-phosphate levels in hypophosphatasia," *J Clin Invest.* 76:752-756 (1985).
Whyte et al., "Marrow cell transplantation for infantile hypophosphatasia," *J Bone Miner Res.* 18:624-636 (2003).
Whyte, "Hypophosphatasia and the role of Alkaline phosphatase in skeletal mineralization," *Endocr Rev.* 15(4):439-461 (1994).
Whyte, Hypophosphatasia: Nature's window on alkaline phosphatase function in man, *Principles of Bone Biology, 2nd ed.*, Bilezikian, Raisz, and Rodan. 2:1229-1248 (2002).
Wroblewski et al., "Pharmacokinetics, metabolic stability, and subcutaneous bioavailability of a genetically engineered analog of DcR3, flint [DcR3(R218Q)], in cynomolgus monkeys and mice," *Drug Metab Dispos.* 31(4):502-507 (2003).

(56) References Cited

OTHER PUBLICATIONS

Yamamoto et al., "Long term phenotypic correction of severe infantile hypophosphatasia in a mouse model by neonatal injection of lentiviral vector," *Mol Ther.* 17:S67-S68, Abstract 171 (2009).
Yamamoto et al., "Prolonged survival and phenotypic correction of Akp2$^{-/-}$hypophosphatasia mice by lentiviral gene therapy," *J Bone Miner Res.* 26(1):135-142 (2011).
Yokogawa et al., "Selective delivery of estradiol to bone by aspartic acid oligopeptide and its effects on ovariectomized mice," *Endocrinology* 142(3):1228-1233 (2001).
Young et al., "Structure, expression, and regulation of the major noncollagenous matrix proteins of bone," *Clin Orthop Relat Res.* 281:275-294 (1992).
Zierhut et al., "Population PK-PD model for Fc-osteoprotegerin in healthy postmenopausal women," *J Pharmacokinet Pharmacodyn.* 35:379-399 (2008).
Zurutuza et al., "Correlations of genotype and phenotype in hypophosphatasia," *Hum Mol Genet.* 8(6):1039-1046 (1999).
Advisory Action for U.S. Appl. No. 11/484,870, dated Dec. 20, 2007 (4 pages).
Communication from Examining Division for European Application No. EP 05 73 9065, dated Jun. 11, 2010 (5 pages).
Communication from Examining Division for European Application No. EP 05 73 9065, dated Jun. 18, 2009 (11 pages).
Communication from Examining Division for European Application No. EP 08 757 088, dated Apr. 20, 2011 (4 pages).
Declaration of Dr. Philippe Crine for EP 08757088.3, executed Jan. 14, 2011 (6 pages).
Extended European Search Report for European Application No. EP 11 00 4496, dated Aug. 26, 2011 (7 pages).
Extended European Search Report for European Application No. EP 11 00 0196, dated Jun. 22, 2011 (6 pages).
European Search Report for European Application No. EP08757088, dated Jun. 21, 2010 (6 pages).
International Preliminary Report on Patentability and Written Opinion for International Application No. PCT/CA2011/050258, dated Nov. 15, 2012 (9 pages).
International Search Report and Written Opinion for International Application No. PCT/CA2011/050258, dated Jul. 29, 2011 (14 pages).
International Search Report and Written Opinion for International Application No. PCT/CA2005/000615, dated Aug. 18, 2005 (14 pages).
International Search Report and Written Opinion for International Application No. PCT/CA2008/000923, dated Sep. 12, 2008 (11 pages).
International Search Report and Written Opinion for International Application No. PCT/US12/39004, dated Nov. 2, 2012 (22 pages).
Invitation to Pay Additional Fees for International Application No. PCT/US12/39004, dated Aug. 29, 2012 (2 pages).
Office Action for U.S. Appl. No. 11/111,664, dated Oct. 4, 2007 (11 pages).
Office Action for U.S. Appl. No. 11/111,664, dated May 14, 2008 (8 pages).
Office Action for U.S. Appl. No. 11/111,664, dated Dec. 4, 2008 (7 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Oct. 1, 2007 (12 pages).
Office Action for U.S. Appl. No. 11/484,870, dated Jun. 25, 2008 (16 pages).
Office Action for U.S. Appl. No. 11/484,870, dated Feb. 2, 2009 (16 pages).
Office Action for U.S. Appl. No. 11/484,870, dated Aug. 11, 2009 (15 pages).
Office Action for U.S. Appl. No. 12/405,920, dated Dec. 17, 2009 (14 pages).
Office Action for U.S. Appl. No. 12/405,920, dated Aug. 9, 2010 (7 pages).
Office Action for U.S. Appl. No. 12/793,517, dated Aug. 16, 2010.
Office Action for U.S. Appl. No. 13/071,445, dated Feb. 6, 2012 (22 pages).
Office Action for U.S. Appl. No. 13/071,445, dated May 25, 2012 (33 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (18 pages).
Supplementary European Search Report for European Application No. EP 05 73 9065, date of completion Nov. 7, 2008.
Supplementary European Search Report for European Application No. EP 08 75 7088 (date of completion of search Jun. 7, 2010, dated Jun. 21, 2010).
Tomatsu, Declaration Under 37 C.F.R. § 1.132 for U.S. Appl. No. 11/484,870, dated Nov. 27, 2007 (2 pages).
Tomatsu, Declaration Under 37 C.F.R. § 1.132 for U.S. Appl. No. 11/484,870, dated Jun. 1, 2009 (3 pages).
Choe et al., "Substrate profiling of cysteine proteases using a combinatorial peptide library identifies functionally unique specificities," J Biol Chem. 281(18):12824-12832 (2006).
Extended European Search Report for European Application No. 11774253.6, dated Oct. 14, 2013 (8 pages).
Yadav et al., "Dose response of bone-targeted enzyyme replacement for murine hypophosphatasia," Bone. 49(2):250-6 (2011) (20 pages).
Mornet et al., "Structural evidence for a functional role of human tissue nonspecific alkaline phosphatase in bone mineralization," J Biol Chem. 276(33):31171-8 (2001).

* cited by examiner

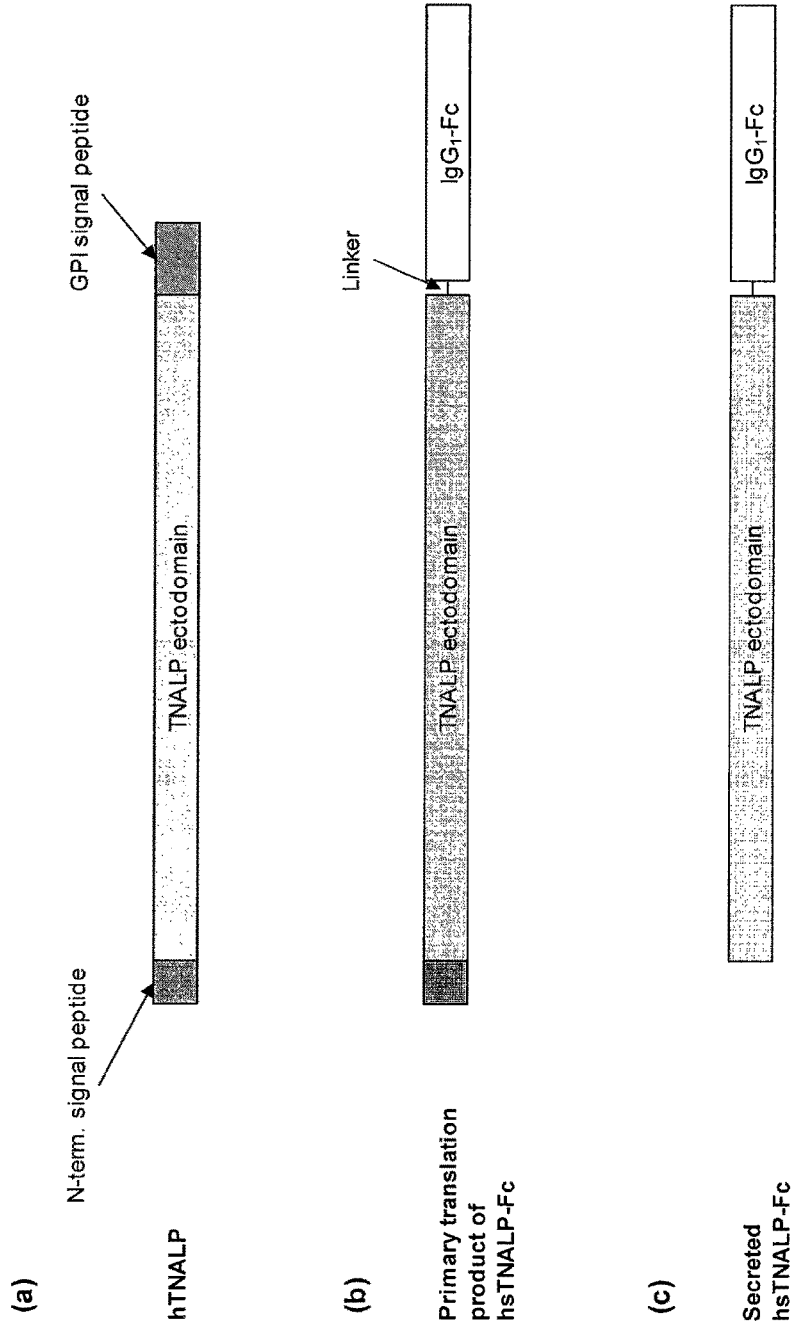

Figure 2

MVSPFLVLAIGTCLTNSLVPEKEKDPKYWRDQAQETLKYALELQKLNTNVAKNVIMFLGDGMGVS
TVTAARILKGQLHHNPGEETRLEMDKFPFVALSKTYNTNAQVPDSAGTATAYLCGVKANEGTVGV
SAATERSRCNTTQGNEVTSILRWAKDAGKSVGIVTTRVNHATPSAAYAHSADRDWYSDNEMPPE
ALSQGCKDIAYQLMHNIRDIDVIMGGGRKYMYPKNKTDVEYESDEKARGTRLDGLDLVDTWKSFK
PRYKHSHFIWNRTELITLDPHNVDYLLGLFEPGDMQYELNRNNVTDPSLSEMVVAIQILRKNPK
GFFLIVEGGRIDHGHHEGKAKQALHEAVEMDRAIGQAGSLTSSEDTLTVVTADHSHVFTFGGYTP
RGNSIFGLAPMLSDTDKKPFTAILYGNGPGYKVVGGERENVSMVDYAHNNYQAQSAVPLRHETHG
GEDVAVFSKGPMAHLLHGVHEQNYVPHVMAYAACIGANLGHCAPASSLKDKTHTCPPCPAPELLG
GPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEA
LHNHYTQKSLSLSPGK

Figure 3

LVPEKEKDPKYWRDQAQETLKYALELQKLNTNVAKNVIMFLGDGMGVSTVTAARILKGQLHHNPG
EETRLEMDKFPFVALSKTYNTNAQVPDSAGTATAYLCGVKANEGTVGVSAATERSRCNTTQGNEV
TSILRWAKDAGKSVGIVTTRVNHATPSAAYAHSADRDWYSDNEMPPEALSQGCKDIAYQLMHNI
RDIDVIMGGGRKYMYPRNKTDVEYESDEKARGTRLDGLDLVDTWKSFKPRYKHSHFIWNRTELLT
LDPHNVDYLLGLFEPGDMQYELNRNNVTDPSLSEMVVVAIQILRKNPKGFFLIVEGGRIDHGHHE
GKAKQALHEAVEMDRAIGQAGSLTSSEDTLTVVTADHSHVFTFGGYTPRGNSIFGLAPMLSDTDK
KPFTAILYGNGPGYKVVGGERENVSMVDYAHNNYQAQSAVPLRHETHGGEDVAVFSKGPMAHLLH
GVHEQNYVPHVMAYAACIGANLGHCAPASSLKDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK

Figure 4

ALP Multiple Sequence Alignment with TNALP Orthologs and Human ALP Isozymes (a)

```
CLUSTAL 2.0.12 multiple sequence alignment sp|Q29486|TNALP_FELCA    MISP-----FLVLAIGTCLTNSLVPEKEKDPKYWRDQAQQTLKNALRLQK    45
tr|Q9NOV0|TNALP_CANFA    --------------EKDPKYWRDQAQQTLKYALRLQN                23
sp|P09487|TNALP_BOVINE   MISP-----FLLAIGTCFASSLVPEKEKDPKYWRDQAQQTLKNALRLQT    45
sp|P09242|TNALP_MOUSE    MISP-----FLVLAIGTCLTNSFVPEKERDPSYWRQQAQETLKNALKLQK    45
sp|P08289|TNALP_RAT      MLLP-----FLVLAIGTCLTNSFVPEKEKDPSYWRQQAQETLKNALKLQK    45
sp|P05186|TNALP_HUMAN    MISP-----FLVLAIGTCLTNSLVPEKEKDPKYWRDQAQETLKYALELQK    45
sp|P10696|GCALP_HUMAN    MQGP----WVLLLLGLRLQLSLGIIPVEEENPDFWNRQAAEALGAAKKLQP   47
sp|P05187|PLALP_HUMAN    MLGPCMLLLLLGLRLQLSLGIIPVEEENPDFWNREAAEALGAAKKLQP     50
sp|P09923|IALP_HUMAN     MQGP----WVLLLGLRLQLSLGVIPAEEENPAFWNRQAAEALDAAKKLQP   47
Consensus                XXXXXXXXXXXXXXXXXXXXXXEXXPXXWXXAXXXLXXAXXLQX sp|Q29486|TNALP_FELCA    LNTNVVKNVIMFLGDGMGVSTVTAARILKGQLHHNPGEETRLEMDKFPYV   95
tr|Q9NOV0|TNALP_CANFA    LNTNVAKNVIMFLGDGMGVSTVTATRILKGQLHHNPGEETRLEMDKFPYV   73
sp|P09487|TNALP_BOVINE   LNTNVAKNVIMFLGDGMGVSTVTAARILKGQLHHSPGEETKLEMDKFPYV   95
sp|P09242|TNALP_MOUSE    LNTNVAKNVIMFLGDGMGVSTVTAARILKGQLHHNTGEETRLEMDKFPFV   95
sp|P08289|TNALP_RAT      LNTNVAKNTIMFLGDGMGVSTVTAARILKGQLHHNTGEETRLEMDKFPFV   95
sp|P05186|TNALP_HUMAN    LNTNVAKNVIMFLGDGMGVSTVTAARILKGQLHHNPGEETRLEMDKFPFV   95
sp|P10696|GCALP_HUMAN    AQT-AAKNLIIFLGDGMGVSTVTAARILKGQKKDKLGPETFLAMDRFPYV   96
sp|P05187|PLALP_HUMAN    AQT-AAKNLIIFLGDGMGVSTVTAARILKGQKKDKLGPEIPLAMDRFPYV   99
sp|P09923|IALP_HUMAN     IQK-VAKNLILFLGDGLGVPTVTATRILKGQKNGKLGPETPLAMDRFPYL   96
Consensus                XXXXXXXKNXIXFLGDGXGVXTVTAXRILKGQXXXXGXEXXLXMDXFPXX sp|Q29486|TNALP_FELCA    ALSKTYNTNAQVPDSAGTATAYLCGVKANEGTVGVSAATQRTQCNTTQGN   145
tr|Q9NOV0|TNALP_CANFA    ALSKTYNTNAQVPDSAGTATAYLCGVKANEGTVGVSAATQRTHCNTTQGN   123
sp|P09487|TNALP_BOVINE   ALSKTYNTNAQVPDSAGTATAYLCGVKANEGTVGVSAATQRSQCNTTQGN   145
sp|P09242|TNALP_MOUSE    ALSKTYNTNAQVPDSAGTATAYLCGVKANEGTVGVSAATERTRCNTTQGN   145
sp|P08289|TNALP_RAT      ALSKTYNTNAQVPDSAGTATAYLCGVKANEGTVGVSAATERTRCNTTQGN   145
sp|P05186|TNALP_HUMAN    ALSKTYNTNAQVPDSAGTATAYLCGVKANEGTVGVSAATERSRCNTTQGN   145
sp|P10696|GCALP_HUMAN    ALSKTYSVDKHVPDSGATATAYLCGVKGNFQTIGLSAAARFNQCNTTRGN   146
sp|P05187|PLALP_HUMAN    ALSKTYNVDKHVPDSGATATAYLCGVKGNFQTIGLSAAARFNQCNTTRGN   149
sp|P09923|IALP_HUMAN     ALSKTYNVDRQVPDSAATATAYLCGVKANFQTIGLSAAARFNQCNTTRGN   146
Consensus                ALSKTYXXXXXVPDSXXTATAYLCGVKXNXXTXGXSAAXXXXCNTTXGN
```

| | | |
|---|---|---|
| sp\|Q29486\|TNALP_FELCA | EVTSILRWAKDSGKSVGIVTTTRVNHATPSAAYAHSADRDWYSDNEMPPE | 195 |
| tr\|Q9N0V0\|TNALP_CANFA | EVTSILRWAKDAGKSVGIVTTTRVNHATPSAAYAHSADRDWYSDNEMPPE | 173 |
| sp\|P09487\|TNALP_BOVINE | EVTSILRWAKDAGKSVGIVTTTRVNHATPSASYAHSADRDWYSDNEMPPE | 195 |
| sp\|P09242\|TNALP_MOUSE | EVTSILRWAKDAGKSVGIVTTTRVNHATPSAAYAHSADRDWYSDNEMPPE | 195 |
| sp\|P08289\|TNALP_RAT | EVTSILRWAKDAGKSVGIVTTTRVNHATPSAAYAHSADRDWYSDNEMPPE | 195 |
| sp\|P05186\|TNALP_HUMAN | EVTSILRWAKDAGKSVGIVTTTRVNHATPSAAYAHSADRDWYSDNEMPPE | 195 |
| sp\|P10696\|GCALP_HUMAN | EVISVMNRAKKAGKSVGVVTTTRVQHASPAGAYAHTVNRNWYSDADVPAS | 196 |
| sp\|P05187\|PLALP_HUMAN | EVISVMNRAKKAGKSVGVVTTTRVQHASPAGTYAHTVNRNWYSDADVPAS | 199 |
| sp\|P09923\|IALP_HUMAN | EVISVMNRAKQAGKSVGVVTTTRVQHASPAGTYAHTVNRNWYSDADMPAS | 196 |
| Consensus | **: *::...:.:..:.*******:::::**: ::*.. | |
| | EVXSXXXXAKXXGKSVGXVTTTRVXHAXPXXXYAHXXXRXWYSDXXXPXX | |
| | | |
| sp\|Q29486\|TNALP_FELCA | ALSQGCKDIAYQLMHNVRDIEVIMGGGRKYMFPKNRTDVEYEMDEKARGT | 245 |
| tr\|Q9N0V0\|TNALP_CANFA | ALSQGCKDIAYQLMHNVRDIEVIMGGGRKYMFPKNRTDVEYEMDEKSTGA | 223 |
| sp\|P09487\|TNALP_BOVINE | ALSQGCKDIAYQLMHNIKDIEVIMGGGRKYMFPKNRTDVEYELDEKARGT | 245 |
| sp\|P09242\|TNALP_MOUSE | ALSQGCKDIAYQLMHNIKDIDVIMGGGRKYMYPKNRTDVEYELDEKARGT | 245 |
| sp\|P08289\|TNALP_RAT | ALSQGCKDIAYQLMHNIKDIDVIMGGGRKYMYPKNRTDVEYELDEKARGT | 245 |
| sp\|P05186\|TNALP_HUMAN | ALSQGCKDIAYQLMHNIRDIDVIMGGGRKYMYPKNKTDVEYESDEKARGT | 245 |
| sp\|P10696\|GCALP_HUMAN | ARQEGCQDIATQLISNM-DIDVILGGGRKYMFPMGTPDPEYPDYSQGGT | 245 |
| sp\|P05187\|PLALP_HUMAN | ARQEGCQDIATQL-SNM-DIDVILGGGRKYMFMRMGTPDPEYPDYSQGGT | 248 |
| sp\|P09923\|IALP_HUMAN | ARQEGCQDIATQL-SNM-DIDVILGGGRKYMFPMGTPDPEYPADASQNGI | 245 |
| Consensus | * .::..**:*: .******: . .*   | |
| | AXXXGCXDIAXQLXXNXXDIXVIXGGGRKYMXXXXXDXEYXXDXXXXGX | |
| | | |
| sp\|Q29486\|TNALP_FELCA | RLDGLNLVDIWKSFKPRHKHSHYVWNRTELLLTLDPY-GVDYLLGLFEPGD | 294 |
| tr\|Q9N0V0\|TNALP_CANFA | RLDGLNLIDIWKNFKPRHKHSHYVWNRTELLALDPY-TVDYLLGLFDPGD | 272 |
| sp\|P09487\|TNALP_BOVINE | RLDGLNLIDIWKSFKPKHKHSHYVWNRTDLLALDPH-SVDYLLGLFEPGD | 294 |
| sp\|P09242\|TNALP_MOUSE | RLDGLDLISIWKSFKPRHKHSHYVWNRTELLALDPS-RVDYLLGLFEPGD | 294 |
| sp\|P08289\|TNALP_RAT | RLDGLDLISIWKSFKPRHKHSHYVWNRTELLALDPS-RVDYLLGLFEPGD | 294 |
| sp\|P05186\|TNALP_HUMAN | RLDGLDLVDTWKSFKPRYKHSHFIWNRTELLLTLDPH-NVDYLLGLFEPGD | 294 |
| sp\|P10696\|GCALP_HUMAN | RLDGKNLVQEWL---AKHQGARYVWNRTELLQASLDPSVTHLMGLFEPGD | 292 |
| sp\|P05187\|PLALP_HUMAN | RLDGKNLVQEWL---AKRQGARYVWNRTELMQASLDPSVTHLMGLFEPGD | 295 |
| sp\|P09923\|IALP_HUMAN | RLDGKNLVQEWL---AKHQGAWYVWNRTELMQASLDQSVTHLMGLFEPGD | 292 |
| Consensus | **. .*. .:.:::****:*: . * :*:**:*** | |
| | RLDGXXLXXXXWXXXXXXXXXXXXXWNRTXLXXXXXXXXXXXXXLXGLFXPGD | |

```
sp|Q29486|TNALP_FELCA    MQYELNRNSTTDPSLSEMVEIAIKILSRNPKGFFLLVEGGRIDHGHHEGK    344
tr|Q9N0V0|TNALP_CANFA    MQYELNRNNVTDPSLSEMVEIAIKILSKKPRGFFLLVEGGRIDHGHHEGK    322
sp|P09487|TNALP_BOVINE   MQYELNRNNATDPSLSEMVENAIRILNKNPKGFFILVEGGRIDHGHHEGK    344
sp|P09242|TNALP_MOUSE    MQYELNRNNLIDPSLSEMVEVALRILTKNLKGFFLLVEGGRIDHGHHEGK    344
sp|P08289|TNALP_RAT      MQYELNRNNLIDPSLSEMVEVALRILTKNPKGFFLLVEGGRIDHGHHEGK    344
sp|P05186|TNALP_HUMAN    MQYELNRNNVTDPSLSEMVVVAIQILRKNPKGFFLLVEGGRIDHGHHEGK    344
sp|P10696|GCALP_HUMAN    MKYEIHRDSTLDPSLMEMTEAALLLLSRNPRGFFLFVEGGRIDHGHHESR    342
sp|P05187|PLALP_HUMAN    MKYEIHRDSTLDPSLMEMTEAALRLLSRNPRGFFLFVEGGRIDHGHHESR    345
sp|P09923|IALP_HUMAN     TKYEIHRDPTLDPSLMEMTEAALRLLSRNPRGFYLFVEGGRIDHGHHEGV    342
Consensus                 :**:::*. ****.**. *:. *: .:: ::.******.*****.
                         XXYEXXRXXXXDPSLXEMXXXXAXXXLXXXXXGFXLXVEGGRIDHGHHEXX sp|Q29486|TNALP_FELCA    AKQALHEAVEMDQAIGRAGAMTSVEDTLITIVTADHSHVFTFGGYTPRGNS   394
tr|Q9N0V0|TNALP_CANFA    AKQALHEAVEMDRAIGKAGVMTSLEDTLTVVTADHSHVFTFGGYTPRGNS   372
sp|P09487|TNALP_BOVINE   AKQALHEAVEMDQAIGQAGAMTSVEDTLITVVTADHSHVFTFGGYTPRGNS   394
sp|P09242|TNALP_MOUSE    AKQALHEAVEMDQAIGKAGAMTSQXDTLTVVTADHSHVFTFGGYTPRGNS   394
sp|P08289|TNALP_RAT      AKQALHEAVEMDEAIGKAGTMTSQXDTLTVVTADHSHVFTFGGYTPRGNS   394
sp|P05186|TNALP_HUMAN    AKQALHEAVEMDRAIGQAGSLTSSEDTLTVVTADHSHVFTFGGYTPRGNS   394
sp|P10696|GCALP_HUMAN    AYRALTETIMFDDAIERAGQLTSEEDTLSLVTADHSHVFSFGGYPLRGSS   392
sp|P05187|PLALP_HUMAN    AYRALTETIMFDDAIERAGQLTSEEDTLSLVTADHSHVFSFGGYPLRGSS   395
sp|P09923|IALP_HUMAN     AYQALTEAVMFDDAIERAGQLTSEEDTLTLVTADHSHVFSFGGYTLRGSS   392
Consensus                * .:** *:: :* ** .:** .:***.::********:.:***.. * . *
                         AXXALXEXXXXDXAIXXAGXXTSXXDTLXXVTADHSHVFXFGGYXXRGXS sp|Q29486|TNALP_FELCA    IFGLAPMVSDTDKKPFTSILYGNGPGYKVVGGERENVSMVDYAHNNYQAQ   444
tr|Q9N0V0|TNALP_CANFA    IFGLAPMVSDTDKKPFTAILYGNGPGYKVVGGERENVSMVDYAHNNYQAQ   422
sp|P09487|TNALP_BOVINE   IFGLAPMVSDTDKKPFTAILYGNGPGYKVVGGERENVSMVDYAHNNYQAQ   444
sp|P09242|TNALP_MOUSE    IFGLAPMVSDTDKKPFTAILYGNGPGYKVVDGERENVSMVDYAHNNYQAQ   444
sp|P08289|TNALP_RAT      IFGLAPMVSDTDKKPFTAILYGNGPGYKVVDGERENVSMVDYAHNNYQAQ   444
sp|P05186|TNALP_HUMAN    IFGLAPMLSDTDKKPFTAILYGNGPGYKVVGGERENVSMVDYAHNNYQAQ   444
sp|P10696|GCALP_HUMAN    IFGLAPGKAR-DRKAYTVLLYGNGPGYVLKDGARPDVTESESGSPEYRQQ   441
sp|P05187|PLALP_HUMAN    IFGLAPGKAR-DRKAYTVLLYGNGPGYVLKDGARPDVTESESGSPEYRQQ   444
sp|P09923|IALP_HUMAN     IFGLAPSKAQ-DSKAYTSILYGNGPGYVFNSGVRPDVNESESGSPDYQQQ   441
Consensus                ****** . . :* . :*******..: .. *.:.*:* .:.. *
                         IFGLAPXXXXXDXFXXXTXXLYGNGPGYXXXGXRXVXXXXXXXXYXXQ
```

```
sp|Q29486|TNALP_FELCA      SAVPLRHETHGGEDVAVFAKGPMAHLLHGVHEQNYIPHVMAYAACIG---  491
tr|Q9NOV0.TNALP_CANFA      SAVPLRHETHGGEDVAVFAKGPMAHLLHGVHEQNYIPHVMAYAACIG---  469
sp|P09487|TNALP_BOVINE     SAVPLRHETHGGEDVAVFAKGPMAHLLHGVHEQNYIPHVMAYAACIG---  491
sp|P09242|TNALP_MOUSE      SAVPLRHETHGGEDVAVFAKGPMAHLLHGVHEQNYIPHVMAYASCIG---  491
sp|P08289|TNALP_RAT        SAVPLRHETHGGEDVAVFAKGPMAHLLHGVHEQNYIPHVMAYASCIG---  491
sp|P05186|TNALP_HUMAN      SAVPLRHETHGGEDVAVFSKGPMAHLLHGVHEQNYVPHVMAYAACIG---  491
sp|P10696|GCALP_HUMAN      SAVPLDGETHAGEDVAVFARGPQAHLVHGVQEQTFIAHVMAFAACLEPYT  491
sp|P05187|PLALP_HUMAN      SAVPLDEETHAGEDVAVFARGPQAHLVHGVQEQTFIAHVMAFAACLEPYT  494
sp|P09923|IALP_HUMAN       AAVPLSSETHGGEDVAVFARGPQAHLVHGVQEQSFVAHVMAFAACLEPYT  491

Consensus                  :**** ***.***********:;**  ***.*;***:**  .:.****  :*:*:
                           XAVPLXXETHXGEDVAVFXXGPXAHLXHGVXEQXXXHVMAXAXCXXXXX sp|Q29486_TNALP_FELCA      -ANLDHCASASSAGGPSPGPLFLLLALPSIGILF---------  524
tr|Q9NOV0.TNALP_CANFA      -ANQDHCASASSAGGPSPGPLLLLLALLLPVGILF--------  502
sp|P09487|TNALP_BOVINE     -ANRDHCASASSSGSPSPGLLLLALLPLGSLF-----------  524
sp|P09242|TNALP_MOUSE      -ANLDHCAWAGSGSAPSPGALLLPLAVLSLPTLF---------  524
sp|P08289|TNALP_RAT        -ANLDHCAWASSASSPSPGALLLPLALFPLRTLF---------  524
sp|P05186|TNALP_HUMAN      -ANLGHCAPASSAGSLAAGPLLLALALYPLSVLF---------  524
sp P10696|GCALP_HUMAN      ACDLAPRAGTTDAAHPGFSVVPALLPLLAGTLLLLGTATAP    532
sp|P05187|PLALP_HUMAN      ACDLAPPAGTTDAAHPGRSVVPALLPLLAGTLLLLETATAP    535
sp P09923|IALP_HUMAN       ACCLAPPACTTDAAHP----VAASLPLLAGTLLLLGASAAP   528

Consensus                    .: *  .:.  *  .*:.. . .*.
                           XXXXXXXXXXAXXXXXXXXXXXXXLXXXXXXLXXXXXXXXX
```

Figure 5

(a) ALP Multiple Sequence Alignment with TNALP Orthologs

```
CLUSTAL 2.0.12 multiple sequence alignment sp|Q29486|TNALP_FELCA     MISPFIVLAIGTCLTNSLVPEKEKDPKYWRDQAQQTLKNALRLQKJNTNV  50
tr|Q9NOV0|TNALP_CANFA     ------------------------EKDPKYWRDQAQQTLKYALRLQN_NTNV  28
sp|P09487|TNALP_BOVINE    MISPFLLLAIGTCFASSLVPEKEKDPKYWRDQAQQTLKNALRLQT_NTNV  50
sp|P09242|TNALP_MOUSE     MISPFIVLAIGTCLTNSFVPEKERDPSYWRQQAQETLKNALKLQKNTNV   50
sp|P08289|TNALP_RAT       MILPFLVLAIGTCLTNSFVPEKEKDPSYWRQQAQETLKNALKLQKLNTNV  50
sp|P05186|TNALP_HUMAN     MISPFIVLAIGTCLTNSLVPEKEKDPKYWRDQAQETLKYALELQKLNTNV  50
                              ***:******: *** ** .******
Consensus                 XXXXXXXXXXXXXXXXXXXXEXDPXYWRXQAQXTLKXALXLQXLNTNV sp|Q29486|TNALP_FELCA     VKNVIMFLGDGMGVSTVTAARILKGQLHHNPGEETRLEMDKFPYVALSKT  100
tr|Q9NOV0|TNALP_CANFA     AKNVIMFLGDGMGVSTVTATRILKGQLHHNPGEETRLEMDKFPYVALSKT  78
sp|P09487|TNALP_BOVINE    AKNVIMFLGDGMGVSTVTAARILKGQLHHSPGEETKLEMDKFPYVALSKT  100
sp|P09242|TNALP_MOUSE     AKNVIMFLGDGMGVSTVTAARILKGQLHHNTGEETRLEMDKFPFVALSKT  100
sp|P08289|TNALP_RAT       AKNIIMFLGDGMGVSTVTAARILKGQLHHNTGEETRLEMDKFPFVALSKT  100
sp|P05186|TNALP_HUMAN     AKNVIMFLGDGMGVSTVTAARILKGQLHHNPGEETRLEMDKFPFVALSKT  100
                          .**.:*********.******:. ****.:*******:*:*******
Consensus                 XKNXIMFLGDGMGVSTVTAXRILKGQLHHXXGEETXLEMDKFPXVALSKT sp|Q29486|TNALP_FELCA     YNTNAQVPDSAGTATAYLCGVKANEGTVGVSAATQRTQCNTTQGNEVTSI  150
tr|Q9NOV0|TNALP_CANFA     YNTNAQVPDSAGTATAYLCGVKANEGTVGVSAATQRTHCNTTQGNEVTSI  128
sp|P09487|TNALP_BOVINE    YNTNAQVPDSAGTATAYLCGVKANEGTVGVSAATQRSQCNTTQGNEVTSI  150
sp|P09242|TNALP_MOUSE     YNTNAQVPDSAGTATAYLCGVKANEGTVGVSAATERTRCNTTQGNEVTSI  150
sp|P08289|TNALP_RAT       YNTNAQVPDSAGTATAYLCGVKANEGTVGVSAATERTRCNTTQGNEVTSI  150
sp|P05186|TNALP_HUMAN     YNTNAQVPDSAGTATAYLCGVKANEGTVGVSAATERSRCNTTQGNEVTSI  150
                          ****************************.*:.:***********
Consensus                 YNTNAQVPDSAGTATAYLCGVKANEGTVGVSAATXRXXCNTTQGNEVTSI sp|Q29486|TNALP_FELCA     LRWAKDSGKSVGIVTTTRVNHATPSAAYAHSADRDWYSDNEMPPEALSQG  200
tr|Q9NOV0|TNALP_CANFA     LRWAKDAGKSVGIVTTTRVNHATPSAAYAHSADRDWYSDNEMPPEALSQG  178
sp|P09487|TNALP_BOVINE    LRWAKDAGKSVGIVTTTRVNHATPSASYAHSADRDWYSDNEMPPEALSQG  200
sp|P09242|TNALP_MOUSE     LRWAKDAGKSVGIVTTTRVNHATPSAAYAHSADRDWYSDNEMPPEALSQG  200
sp|P08289|TNALP_RAT       LRWAKDAGKSVGIVTTTRVNHATPSAAYAHSADRDWYSDNEMPPEALSQG  200
sp|P05186|TNALP_HUMAN     LRWAKDAGKSVGIVTTTRVNHATPSAAYAHSADRDWYSDNEMPPEALSQG  200
                          ******.********************:********************
Consensus                 LRWAKDXGKSVGIVTTTRVNHATPSAXYAHSADRDWYSDNEMPPEALSQG
```

```
sp|Q29486|TNALP_FELCA    CKDIAYQLMHNVRDIEVIMGGGRKYMFPKNRTDVEYEMDEKARGTRLDGL 250
tr|Q9NOVO|TNALP_CANFA    CKDIAYQLMHNVKDIEVIMGGGRKYMFPKNRTDVEYEMDEKSTGARLDGL 228
sp|P09487|TNALP_BOVINE   CKDIAYQLMHNIKDIEVIMGGGRKYMFPKNRTDVEYELDEKARGTRLDGL 250
sp|P09242|TNALP_MOUSE    CKDIAYQLMHNIKDIDVIMGGGRKYMYPKNRTDVEYELDEKARGTRLDGL 250
sp|P08289|TNALP_RAT      CKDIAYQLMHNIKDIDVIMGGGRKYMYPKNRTDVEYELDEKARGTRLDGL 250
sp|P05186|TNALP_HUMAN    CKDIAYQLMHNIRDIDVIMGGGRKYMYPKNKTDVEYESDEKARGTRLDGL 250
                         *********..:*:*************:*******.****.:.:*****
Consensus                CKDIAYQLMHNXXDIXVIMGGGRKYMXPKNXTDVEYEXDEKXXGXRLDGL sp|Q29486|TNALP_FELCA    NLVDIWKSFKPRHKHSHYVWNRTELLTLDPYGVDYLLGLFEPGDMQYELN 300
tr|Q9NOVO|TNALP_CANFA    NLIDIWKNFKPRHKHSHYVWNRTELLALDPYTVDYLIGLFDPGDMQYELN 278
sp|P09487|TNALP_BOVINE   NLIDIWKSFKPKHKHSHYVWNRTDLLALDPHSVDYLLGLFEPGDMQYELN 300
sp|P09242|TNALP_MOUSE    DLISIWKSFKPRHKHSHYVWNRTELLALDPSRVDYLLGLFEPGDMQYELN 300
sp|P08289|TNALP_RAT      DLISIWKSFKPRHKHSHYVWNRTELLALDPSRVDYLLGLFEPGDMQYELN 300
sp|P05186|TNALP_HUMAN    DLVDTWKSFKPRYKHSHFIWNRTELJTLDPHNVDYLLGLFEPGDMQYELN 300
                         :*: .**..**.:****.:*****  :*:***. ***************
Consensus                XLXXXWKXFKPXXKHSHXXWNRTXLLXLDPXXVDYLLGLFXPGDMQYELN sp|Q29486|TNALP_FELCA    RNSTTDPSLSEMVE-AIKILSKNPKGFLLVEGGRIDHGHHEGKAKQALH 350
tr|Q9NOVO|TNALP_CANFA    RNNVTDPSLSEMVE-AIKILSKKPRGFFLLVEGGRIDHGHHEGKAKQALH 328
sp|P09487|TNALP_BOVINE   RNNATDPSLSEMVEMAIRILNKNPKGFFLLVEGGRIDHGHHEGKAKQALH 350
sp|P09242|TNALP_MOUSE    RNNLTDPSLSEMVEVALRILTKNIKGFFLLVEGGRIDHGHHEGKAKQALH 350
sp|P08289|TNALP_RAT      RNNLTDPSLSEMVEVALRILTKNPKGFFLLVEGGRIDHGHHEGKAKQALH 350
sp|P05186|TNALP_HUMAN    RNNVTDPSLSEMVVVAIQILRKNPKGFFLLVEGGRIDHGHHEGKAKQALH 350
                         **. .*********  *::.:** *: .******************** 
Consensus                RNXXTDPSLSEMVXXAXXILXKXXXGFFLLVEGGRIDHGHHEGKAKQALH sp|Q29486|TNALP_FELCA    EAVEMDQAIGRAGAMTSVEDTLITIVTADHSHVFTFGGYTFGGNSIFGLAP 400
tr|Q9NOVO|TNALP_CANFA    EAVEMDRAIGKAGVMTSLEDTLITVVTADHSHVFTFGGYTPRGNSIFGLAP 378
sp|P09487|TNALP_BOVINE   EAVEMDQAIGQAGAMTSVEDTLITVVTADHSHVFTFGGYTPRGNSIFGLAP 400
sp|P09242|TNALP_MOUSE    EAVEMDQAIGKACAMTSQKDCLITVVTADFSHVFTFGGYTPRGNSIFGLAP 400
sp|P08289|TNALP_RAT      EAVEMDEAIGKAGTMTSQKCLITVVTADFSHVFTFGGYTPRGNSIFGLAP 400
sp|P05186|TNALP_HUMAN    EAVEMDRAIGQAGSLTSSEDTLITVVTADHSHVFTFGGYTPRGNSIFGLAP 400
                         ******.:**:**  :** .:  :*****:*******************
Consensus                EAVEMDXAIGXAGXXTSXXDTLITXVTADHSHVFTFGGYTPRGNSIFGLAP
```

| | | |
|---|---|---|
| sp\|Q29486\|TNALP_FELCA | MVSDTDKKPFTSILYGNGPGYKVVGGERENVSMVDYAHNNYQAQSAVPLR | 450 |
| tr\|Q9NOV0\|TNALP_CANFA | MVSDTDKKPFTAILYGNGPGYKVVGGERENVSMVDYAHNNYQAQSAVPLR | 428 |
| sp\|P09487\|TNALP_BOVINE | MVSDTDKKPFTAILYGNGPGYKVVGGERENVSMVDYAHNNYQAQSAVPLR | 450 |
| sp\|P09242\|TNALP_MOUSE | MVSDTDKKPFTAILYGNGPGYKVVDGERENVSMVDYAHNNYQAQSAVPLR | 450 |
| sp\|P08289\|TNALP_RAT | MVSDTDKKPFTAILYGNGPGYKVVDGERENVSMVDYAHNNYQAQSAVPLR | 450 |
| sp\|P05186\|TNALP_HUMAN | MLSDTDKKPFTAILYGNGPGYKVVGGERENVSMVDYAHNNYQAQSAVPLR | 450 |
|  | *:*********:*****.************************* |  |
| Consensus | MXSDTDKKPFTXILYGNGPGYKVVXGERENVSMVDYAHNNYQAQSAVPLR |  |

| | | |
|---|---|---|
| sp\|Q29486\|TNALP_FELCA | HETHGGEDVAVFAKGPMAHLLHGVHEQNYIPHVMAYAACIGANLDHCASA | 500 |
| tr\|Q9NOV0\|TNALP_CANFA | HETHGGEDVAVFAKGPMAHLLHGVHEQNYIPHVMAYAACIGANQDHCASA | 478 |
| sp\|P09487\|TNALP_BOVINE | HETHGGEDVAVFAKGPMAHLLHGVHEQNYIPHVMAYAACIGANRDHCASA | 500 |
| sp\|P09242\|TNALP_MOUSE | HETHGGEDVAVFAKGPMAHLLHGVHEQNYIPHVMAYASCIGANLDHCAWA | 500 |
| sp\|P08289\|TNALP_RAT | HETHGGEDVAVFAKGPMAH-LFGVHEQNYIPHVMAYASC-GANLDHCAWA | 500 |
| sp\|P05186\|TNALP_HUMAN | HETHGGEDVAVFSKGPMAH-LFGVHEQNVPHVMAYAAC-GANLGHCAPA | 500 |
|  | **********:****:*******:*.*.* |  |
| Consensus | HETHGGEDVAVFXKGPMAHLLHGVHEQNYXPHVMAYAXCIGANXXHCAXA |  |

| | | |
|---|---|---|
| sp\|Q29486\|TNALP_FELCA | SSAGGPSPGPLFLLLALPSIGILF | 524 |
| tr\|Q9NOV0\|TNALP_CANFA | SSAGGPSPGPLLLLLALLPVGILF | 502 |
| sp\|P09487\|TNALP_BOVINE | SSSGSPSPGPLLLLALLPLGSLF | 524 |
| sp\|P09242\|TNALP_MOUSE | GSCSAPSPGALLLPLAVLSLPTLF | 524 |
| sp\|P08289\|TNALP_RAT | SSASSPSPGALLPLALFPLRTLF | 524 |
| sp\|P05186\|TNALP_HUMAN | SSAGSLAAGPLLLALALYPLSVLF | 524 |
|  | .*....:.*.:.:. |  |
| Consensus | XSXXXXXXGXLXLXLAXXXXXLF |  |

Figure 6

```
atggtttcaccattcttagtactggccattggcacctgccttactaactccttagtg
ccagagaaagagaaagaccccaagtactggcgagaccaagcgcaagagacactgaaa
tatgccctggagcttcagaagctcaacaccaacgtggctaagaatgtcatcatgttc
ctgggagatgggatgggtgtctccacagtgacggctgcccgcatcctcaagggtcag
ctccaccacaaccctggggaggagaccaggctggagatggacaagttccccttcgtg
gccctctccaagacgtacaacaccaatgcccaggtccctgacagcgccggcaccgcc
accgcctacctgtgtgggggtgaaggccaatgagggcaccgtggggtaagcgcagcc
actgagcgttcccggtgcaacaccacccaggggaacgaggtcacctccatcctgcgc
tgggccaaggacgctgggaaatctgtgggcattgtgaccaccacgagagtgaaccat
gccacccccagcgccgcctacgcccactcggctgaccgggactggtactcagacaac
gagatgcccctgaggccttgagccagggctgtaaggacatcgcctaccagctcatg
cataacatcagggacattgacgtgatcatggggggtggccggaaatacatgtacccc
aagaataaaactgatgtggagtatgagagtgacgagaaagccaggggcacgaggctg
gacggcctggacctcgttgacacctggaagagcttcaaaccgagatacaagcactcc
cacttcatctggaaccgcacggaactcctgacccttgaccccacaatgtggactac
ctattgggtctcttcgagccaggggacatgcagtacgagctgaacaggaacaacgtg
acggacccgtcactctccgagatggtggtggtggccatccagatcctgcggaagaac
cccaaaggcttcttcttgctggtggaaggaggcagaattgaccacgggcaccatgaa
ggaaaagccaagcaggccctgcatgaggcggtggagatggaccgggccatcgggcag
gcaggcagcttgacctcctcggaagacactctgaccgtggtcactgcggaccattcc
cacgtcttcacatttggtggatacaccccgtggcaactctatctttggtctggcc
cccatgctgagtgacacagacaagaagcccttcactgccatcctgtatggcaatggg
cctggctacaaggtggtgggcggtgaacgagagaatgtctccatggtggactatgct
cacaacaactaccaggcgcagtctgctgtgcccctgcgccacgagacccacggcggg
gaggacgtggccgtcttctccaagggccccatggcgcacctgctgcacggcgtccac
gagcagaactacgtcccccacgtgatggcgtatgcagcctgcatcggggccaacctc
ggccactgtgctcctgccagctcgcttaaggacaaaactcacacatgcccaccgtgc
ccagcacctgaactcctgggggaccgtcagtcttcctcttccccccaaaacccaag
gacaccctcatgatctcccggacccctgaggtcacatgcgtggtggtggacgtgagc
cacgaagaccctgaggtcaagttcaactggtacgtggacggcgtggaggtgcataat
gccaagacaaagccgcgggaggagcagtacaacagcacgtaccgtgtggtcagcgtc
ctcaccgtcctgcaccaggactggctgaatggcaaggagtacaagtgcaaggtctcc
aacaaagccctcccagcccccatcgagaaaaccatctccaaagccaagggcagccc
cgagaaccacaggtgtacaccctgcccccatcccgggaggagatgaccaagaaccag
gtcagcctgacctgcctggtcaaaggcttctatcccagcgacatcgccgtggagtgg
gagagcaatgggcagccggagaacaactacaagaccacgcctcccgtgctggactcc
gacggctccttcttcctctatagcaagctcaccgtggacaagagcaggtggcagcag
gggaacgtcttctcatgctccgtgatgcatgaggctctgcacaaccactacacgcag
aagagcctctccctgtctccgggtaaa
```

METHODS, COMPOSITIONS, AND KITS FOR THE TREATMENT OF MATRIX MINERALIZATION DISORDERS

CROSS-REFERENCE TO RELATED APPLICATIONS

This application is the U.S. National Stage filing under 35 U.S.C. § 371 of International Application No. PCT/CA2011/050258, filed Apr. 29, 2011, which claims the benefit of U.S. Provisional Application No. 61/328,877, filed Apr. 30, 2010.

BACKGROUND OF THE INVENTION

The present invention relates to the treatment of matrix mineralization disorders such as hypophosphatasia (HPP). HPP is a rare, heritable disease caused by one or more loss-of-function mutation in the gene ALPL, which encodes tissue-nonspecific alkaline phosphatase (TNALP; a.k.a liver/bone/kidney type ALP). Alkaline phosphatase deficiency in osteoblasts and chondrocytes impairs skeletal mineralization, leading to rickets or osteomalacia. The severity of HPP depends on its age of onset. Perinatal HPP, the most severe form of HPP, results in an almost complete absence of bone mineralization in utero and can cause stillbirth. Infantile HPP, diagnosed before the age of six months, results in impaired skeletal mineralization that can lead to fractures and deformities. Childhood HPP can cause the premature loss of deciduous teeth and rickets. Finally, adult HPP can cause stress fractures and attacks of arthritis and pyrophosphate arthropathy.

Given the devastating immediate and long-term impact of matrix mineralization disorders such as HPP on affected patients, particularly infants and children, there is a need to develop methods and compositions for treating matrix mineralization disorders.

SUMMARY OF THE INVENTION

In the present invention, it has surprisingly been found that an alkaline phosphatase-Fc fusion protein lacking a polyaspartic acid or polyglutamic acid region is effective in treating HPP in an HPP mouse model. Accordingly, the present invention provides compositions including an sALP-Fc or Fc-sALP polypeptide and compositions including a nucleic acid that encodes an sALP-Fc or Fc-sALP polypeptide. The invention also provides methods and kits for using such polypeptides and nucleic acids to treat matrix mineralization disorders such as HPP and its associated phenotypes.

Accordingly, in one aspect, the invention features a method of treating a matrix mineralization disorder in a subject, the method including administering to the subject a therapeutically effective amount of a pharmaceutical composition including: (a) a polypeptide including the structure Z-sALP-Y-Fc-X or the structure Z-Fc-Y-sALP-X; and (b) a pharmaceutically acceptable excipient, where sALP is the extracellular domain of an alkaline phosphatase; each of X, Y, and Z is absent or is an amino acid sequence of at least one amino acid; and the polypeptide does not include a polyaspartic acid or polyglutamic acid region longer than three consecutive aspartic acid or glutamic acid residues.

In another aspect, the invention features a pharmaceutical composition including: (a) a polypeptide including the structure Z-sALP-Y-Fc-X or the structure Z-Fc-Y-sALP-X; and (b) a pharmaceutically acceptable excipient, where sALP is the extracellular domain of an alkaline phosphatase; each of X, Y, and Z is absent or is an amino acid sequence of at least one amino acid; and the polypeptide does not include a polyaspartic acid or polyglutamic acid region longer than three consecutive aspartic acid or glutamic acid residues.

In yet another aspect, the invention features a method of treating a matrix mineralization disorder in a subject, the method including administering to the subject a therapeutically effective amount of a pharmaceutical composition including: (a) an isolated nucleic acid encoding a polypeptide including the structure Z-sALP-Y-Fc-X or the structure Z-Fc-Y-sALP-X; and (b) a pharmaceutically acceptable excipient, where sALP is the extracellular domain of an alkaline phosphatase; each of X, Y, and Z is absent or is an amino acid sequence of at least one amino acid; and the isolated nucleic acid does not encode an amino acid sequence including a polyaspartic acid or polyglutamic acid region longer than three consecutive aspartic acid or glutamic acid residues.

In another aspect, the invention features a pharmaceutical composition formulated for the treatment of a matrix mineralization disorder in a subject, the pharmaceutical composition including: (a) an isolated nucleic acid encoding a polypeptide including the structure Z-sALP-Y-Fc-X or the structure Z-Fc-Y-sALP-X; and (b) a pharmaceutically acceptable excipient, where sALP is the extracellular domain of an alkaline phosphatase; each of X, Y, and Z is absent or is an amino acid sequence of at least one amino acid; and the isolated nucleic acid does not encode an amino acid sequence including a polyaspartic acid or polyglutamic acid region longer than three consecutive aspartic acid or glutamic acid residues.

In any embodiment of the invention, the polypeptide may optionally include the structure Z-sALP-Y-Fc-X.

In any embodiment, the polypeptide optionally does not include a polyaspartic acid or polyglutamic acid region longer than two consecutive aspartic acid or glutamic acid residues.

In any embodiment, the polypeptide optionally does not include a bone-targeting moiety.

In any embodiment, the amino acid sequence of the sALP optionally includes or consists of amino acid residues 23-508 of SEQ ID NO: 15. For example, the amino acid sequence of the sALP optionally includes or consists of amino acid residues 23-512 of SEQ ID NO: 15.

In any embodiment, the amino acid sequence of the sALP optionally includes or consists of amino acid residues 18-498 of SEQ ID NO: 16. For example, the amino acid sequence of the sALP may optionally include or consist of amino acid residues 18-502 of SEQ ID NO: 16.

In any embodiment, the amino acid sequence of the sALP optionally includes an amino acid sequence having at least 85% (e.g., at least 95% or 99%) sequence identity to SEQ ID NO: 5. For example, the amino acid sequence of the sALP optionally includes SEQ ID NO: 5 or consists of SEQ ID NO: 5.

In any embodiment, the Fc may optionally include a $C_{H2}$ domain, a $C_{H3}$ domain and a hinge region. For example, the Fc optionally is a constant domain of an immunoglobulin selected from the group consisting of IgG-1, IgG-2, IgG-3, IgG-3 and IgG-4. In particular embodiments, the immunoglobulin is IgG-1. In other particular embodiments, the Fc includes an amino acid sequence having at least 85% (e.g., at least 95% or 99%) sequence identity to SEQ ID NO: 3.

For example, the amino acid sequence of the Fc optionally includes SEQ ID NO: 3 or consists of SEQ ID NO: 3.

In any embodiment, Z is optionally absent.

In any embodiment, Y is optionally two amino acid residues (e.g., leucine-lysine).

In any embodiment, X is optionally absent.

In any embodiment, Z and X may both be absent, and Y may be absent or may be an amino acid sequence of at least one amino acid. For example, the polypeptide may consist of the structure sALP-Y-Fc or the structure Fc-Y-sALP. In some embodiments of polypeptides consisting of the structure sALP-Y-Fc or Fc-Y-sALP, Y may consist of two amino acid residues, e.g., leucine-lysine. For example, the polypeptide may consist of the structure sALP-Y-Fc. Optionally, the amino acid sequence of sALP is the amino acid sequence of SEQ ID NO: 5, the amino acid sequence of Y is leucine-lysine, and/or the amino acid sequence of Fc is the amino acid sequence of SEQ ID NO: 3. For example, the amino acid sequence of the polypeptide may consist of the amino acid sequence of SEQ ID NO: 4.

In any embodiment, the amino acid sequence of the polypeptide optionally includes an amino acid sequence having at least 85% (e.g., at least 95% or 99%) sequence identity to SEQ ID NO: 4. For example, the amino acid sequence of the polypeptide may optionally include SEQ ID NO: 4 or consist of SEQ ID NO: 4.

In any embodiment, the polypeptide optionally is pegylated or glycosylated.

In any embodiment, the pharmaceutical composition optionally includes a dimer of the polypeptide.

In any embodiment, the pharmaceutically acceptable excipient optionally includes saline.

In any embodiment, the pharmaceutical composition is optionally lyophilized.

In any of the methods of the invention, the pharmaceutical composition is optionally administered subcutaneously, intravenously, orally, nasally, intramuscularly, sublingually, intrathecally, or intradermally. In certain embodiments, the pharmaceutical composition is administered subcutaneously. For example, the methods of the invention may optionally include administering a pharmaceutical composition including the polypeptides of the invention to the subject in a dosage of about 0.5 mg/kg/day to about 10 mg/kg/day (e.g., about 2 mg/kg/day to about 3 mg/kg/day). In other examples, the methods include administering the pharmaceutical composition to the subject between one and seven times a week (e.g., three times a week).

In any of the methods of the invention, the matrix mineralization disorder is optionally hypophosphatasia (e.g., infantile HPP, childhood HPP, perinatal HPP, adult HPP, or odontohypophosphatasia).

In any of the methods of the invention, the pharmaceutical composition is optionally administered in an amount that is therapeutically effective to treat a HPP phenotype selected from the group consisting of HPP-related seizure, premature loss of deciduous teeth, incomplete bone mineralization, elevated blood and/or urine levels of inorganic pyrophosphate ($PP_i$), elevated blood and/or urine levels of phosphoethanolamine (PEA), elevated blood and/or urine levels of pyridoxal 5'-phosphate (PLP), inadequate weight gain, rickets, bone pain, calcium pyrophosphate dihydrate crystal deposition, aplasia, hypoplasia, and dysplasia of the dental cementum. In some embodiments, the incomplete bone mineralization is incomplete femoral bone mineralization, incomplete tibial bone mineralization, incomplete metatarsal bone mineralization, or incomplete rib bone mineralization.

In any embodiment, the subject may be human.

Any of the pharmaceutical compositions of the invention may optionally be formulated for treating a matrix mineralization disorder in a subject.

In any of the methods of the invention featuring the administration of an isolated nucleic acid, the isolated nucleic acid is optionally administered to the subject in a lentiviral vector. In some embodiments, the isolated nucleic acid is optionally administered to the subject at a dosage of from about 0.1 mg to about 10 mg.

Any of the pharmaceutical composition of the invention featuring an isolated nucleic acid may optionally include a recombinant expression vector (e.g., a lentiviral vector) including the isolated nucleic acid.

The invention also features an isolated recombinant host cell transformed or transfected with such a vector.

The invention also features methods of producing any polypeptide of the invention, including culturing such a host cell in a culture medium under conditions suitable to effect expression of the polypeptide and recovering the polypeptide from the culture medium. For example, the host cell is optionally an L cell, a C127 cell, a 3T3 cell, a CHO cell, a BHK cell, or a COS-7 cell. In some embodiments, the host cell is a CHO cell (e.g., a CHO-DG44 cell).

The invention also features kits. For example, the invention features a kit including: (a) any of the pharmaceutical compositions of the invention and (b) instructions for administering the pharmaceutical composition to a subject to treat a matrix mineralization disorder.

By "about" is meant ±10% of the recited value.

By "bone-targeting moiety" is meant an amino acid sequence of between 6 and 20 amino acid residues in length having a sufficient affinity to the bone matrix such that the bone-targeting moiety has an in vivo binding affinity to the bone matrix that is at least $10^{-6}$ M or better (e.g., $10^{-7}$M, $10^{-8}$M, $10^{-9}$ M, or better).

By "Fc" is meant a fragment crystallizable region of an immunoglobulin, e.g., IgG-1, IgG-2, IgG-3, IgG-3 or IgG-4, including the $C_{H2}$ and $C_{H3}$ domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 3.

By "matrix mineralization disorder" is meant a disorder affecting mineralization of the bone matrix or any phenotype associated with the disorder. Matrix mineralization disorders and their associated phenotypes include, for example, rickets (defects in growth plate cartilage), osteomalacia, osteogenesis imperfecta, severe osteoporosis, and hypophosphatasia (HPP) (e.g., infantile HPP, childhood HPP, perinatal HPP, adult HPP, or odontohypophosphatasia), HPP-related seizure, premature loss of deciduous teeth, incomplete bone mineralization, elevated blood and/or urine levels of inorganic pyrophosphate ($PP_i$), elevated blood and/or urine levels of phosphoethanolamine (PEA), elevated blood and/or urine levels of pyridoxal 5'-phosphate (PLP), inadequate weight gain, bone pain, calcium pyrophosphate dihydrate (CPPD) crystal deposition, and aplasia, hypoplasia or dysplasia of the dental cementum. Matrix mineralization disorders can be diagnosed, for example, by growth retardation with a decrease of long bone length (such as femur, tibia, humerus, radius, ulna), a decrease of the mean density of total bone and a decrease of bone mineralization in bones such as femur, tibia, ribs and metatarsi, and phalange, a decrease in teeth mineralization, and premature loss of deciduous teeth (e.g., aplasia, hypoplasia or dysplasia of dental cementum). Without being so limited, treatment of matrix mineralization disorders may be observed by one or more of the following: an increase of long bone length, an increase of mineralization in bone and/or teeth, a correction of bowing of the legs, a reduction of bone pain and a reduction of CPPD crystal deposition in joints.

By "pharmaceutical composition" is meant a composition containing a polypeptide or nucleic acid described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for subcutaneous administration; or any other formulation described herein.

By "pharmaceutically acceptable excipient" is meant a carrier that is physiologically acceptable to the treated subject while retaining the therapeutic properties of the compound with which it is administered. One exemplary pharmaceutically acceptable excipient is physiological saline. Other physiologically acceptable excipients and their formulations are known to one skilled in the art and described, for example, in "Remington: The Science and Practice of Pharmacy" (20th ed., ed. A. R. Gennaro, 2000, Lippincott Williams & Wilkins).

By "polypeptide" is meant any natural or synthetic chain of amino acids at least two amino acids in length, including those having post-translational modification (e.g, glycosylation or phosphorylation).

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al. *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

The terms "sALP," "soluble alkaline phosphatase," and "extracellular domain of an alkaline phosphatase" are used interchangeably and mean a soluble, non-membrane-bound alkaline phosphatase or a domain, biologically active fragment, or biologically active variant thereof. sALPs include, for example, an alkaline phosphatase lacking a C-terminal GPI signal sequence, e.g., a polypeptide including or consisting of the amino acids 18-502 of human TNALP (SEQ ID NO: 6). sALPs further include, for example, soluble, non-membrane-bound forms of mammalian orthologs of human TNALP (e.g., polypeptides including or consisting of amino acids 16-502 or 18-502 of SEQ ID NO: 7, amino acids 18-502 of SEQ ID NO: 8, amino acids 18-502 of SEQ ID NO: 9, amino acids 18-502 of SEQ ID NO: 10, or amino acids 1-480 of SEQ ID NO: 11), soluble, non-membrane-bound forms of human IALP, GCALP, and PLALP (e.g., polypeptides including or consisting of amino acids 20-503 of SEQ ID NO: 12, amino acids 20-503 of SEQ ID NO: 13, or amino acids 23-506 of SEQ ID NO: 14), and additional variants and analogs thereof which retain alkaline phosphatase activity, e.g., the ability to hydrolyze $PP_i$.

By "subject" is meant any mammal, e.g., a human.

By "therapeutically effective amount" is meant an amount of a nucleic acid or polypeptide of the invention that is sufficient to substantially treat, prevent, delay, suppress, or arrest any symptom of a matrix mineralization disorder. A therapeutically effective amount of a compound of the invention may depend on the severity of the matrix mineralization disorder and the condition, weight and general state of the subject and can be determined by ordinarily-skilled artisan with consideration of such factors. A therapeutically effective amount of a compound of the invention can be administered to a mammal in a single dose or in multiple doses administered over a period of time.

By "treating" is meant administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

BRIEF DESCRIPTION OF THE DRAWINGS

FIG. 1 shows schematic representations of polypeptides of the present invention. (a) The complete primary translation product of the human tissue non-specific alkaline phosphatase gene (hTNALP), including the N-terminal signal peptide and the transient membrane-anchored signal for GPI addition. (b) The primary translation product of the hsTNALP-Fc fusion protein. (c) The secreted hsTNALP-Fc, which lacks the N-terminal signal peptide.

FIG. 2 shows the amino acid sequence of hsTNALP-Fc (SEQ ID NO: 1), including the N-terminal signal peptide (the first 17 amino acid residues, underlined and italicized; position 2, a valine, differs from the wild-type residue in that position, isoleucine). Amino acids of the hsTNALP portion of the polypeptide (SEQ ID NO: 2), which correspond to amino acids 1-502 of hTNALP (SEQ ID NO: 6), with the exception of position 2 as noted above, are italicized. The Fc portion of this polypeptide (SEQ ID NO: 3) is underlined. A two amino acid leucine-lysine linker between the hsTNALP and Fc portions is shown in bold.

FIG. 3 shows the amino acid sequence of secreted hsT-NALP-Fc (SEQ ID NO: 4), which lacks the N-terminal signal peptide. Amino acids of the hsTNALP portion of the polypeptide (SEQ ID NO: 5), which correspond to amino acids 18-502 of hTNALP, are italicized. The Fc portion of this polypeptide (SEQ ID NO: 3) is underlined. A two amino acid leucine-lysine linker between the hsTNALP and Fc portions is shown in bold.

FIGS. 4(a)-(d) show a CLUSTAL™ W (1.82) multiple sequence alignment of mammalian TNALP orthologs and human ALP isozymes. Mammalian TNALP orthologs include human TNALP ("sp|P05186|TNALP_HUMAN"; Accession No. P05186; SEQ ID NO: 6), cow TNALP ("sp|P09487|TNALP_BOVINE"; Accession No. P09487; SEQ ID NO: 7); cat TNALP ("sp|Q29486|TNALP_FELCA"; Accession No. Q29486; SEQ ID NO: 8), mouse TNALP ("sp|P09242|TNALP_MOUSE"; Accession. No. P09242; SEQ ID NO: 9), rat TNALP ("sp|P08289|TNALP_RAT"; Accession No. P08289; SEQ ID NO: 10), and a partial sequence of dog TNALP ("tr|Q9N0V0|TNALP_CANFA"; Accession No. Q9N0V0; SEQ ID NO: 11). Human ALP isozymes include a human IALP ("sp|P09923|IALP_HUMAN"; Accession No. P09923; SEQ ID NO: 12), a human GCALP ("sp|P10696|GCALP_HUMAN"; Accession No. P10696; SEQ ID NO: 13), and a human PLALP ("sp|P05187|PLALP_HUMAN"; Accession No. 05187; SEQ ID NO: 14). "*" denotes that the residues in that column are identical in all sequences of the alignment, ":" denotes that conserved substitutions are observed, and "." denotes that semi-conserved substitutions are observed. A consensus sequence is derived from this alignment ("Consensus"; SEQ ID NO: 15), where X denotes degenerate positions.

FIGS. 5(a)-(c) show a CLUSTAL™ W (1.82) multiple sequence alignment of mammalian TNALP orthologs, including human TNALP ("sp|P05186|TNALP_HUMAN"; Accession No. P05186; SEQ ID NO: 6), cow TNALP ("sp|P09487|TNALP_BOVINE"; Accession No. P09487; SEQ ID NO: 7); cat TNALP ("sp|Q29486|TNALP_FELCA"; Accession No. Q29486; SEQ ID NO: 8), mouse TNALP ("sp|P09242|TNALP_MOUSE"; Accession No. P09242; SEQ ID NO: 9), rat TNALP ("sp|P08289|TNALP_RAT"; Accession No. P08289; SEQ ID NO: 10), and a partial sequence of dog TNALP ("tr|Q9N0V0|TNALP_CANFA"; Accession No. Q9N0V0; SEQ ID NO: 11). "*" denotes that the residues in that column are identical in all sequences of the alignment, ":" denotes that conserved substitutions are observed, and "." denotes that semi-conserved substitutions are observed. A consensus sequence is derived from this alignment ("Consensus"; SEQ ID NO: 16), where X denotes degenerate positions.

FIG. 6 shows a nucleic acid sequence (SEQ ID NO: 17) encoding the hsTNALP-Fc polypeptide depicted in FIG. 2.

DETAILED DESCRIPTION

Figure 7:
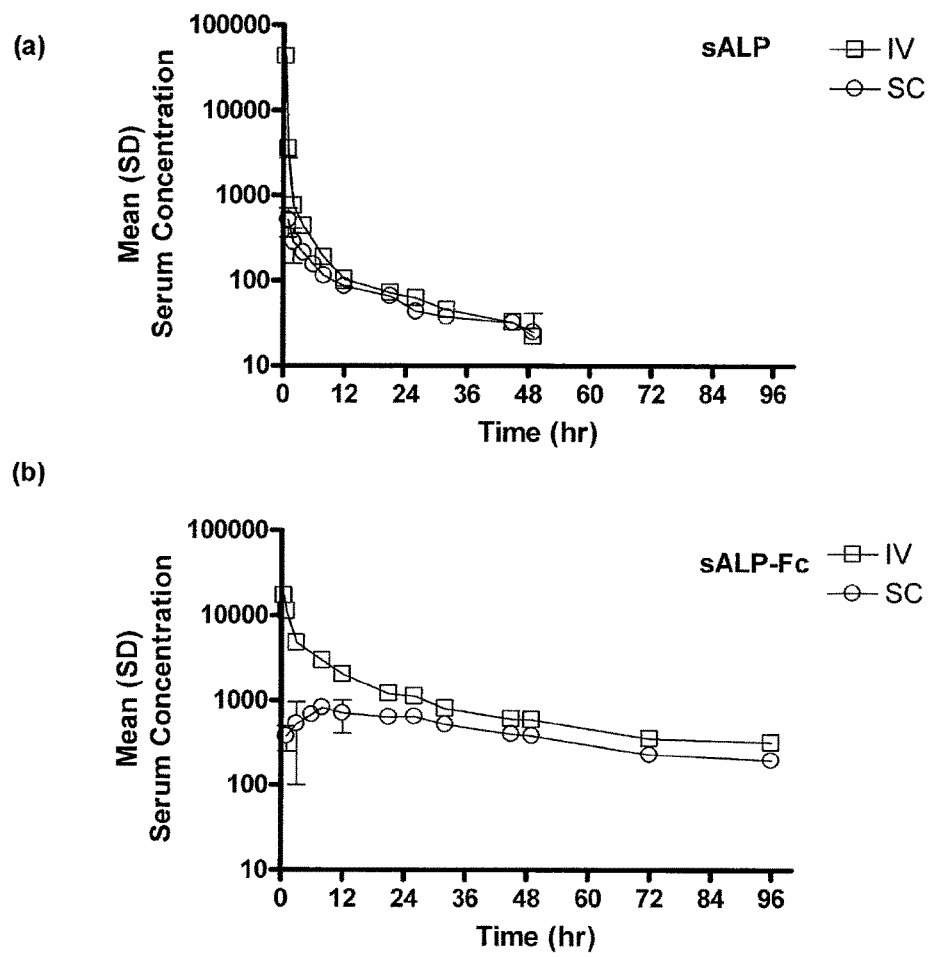
FIG. 7 shows the mean (±SD) concentration profile in serum following single dose IV and SC administration of (a) sALP and (b) sALP-Fc.

The present invention features soluble alkaline phosphatase (sALP) fused to Fc, nucleic acid encoding such, and their uses to treat matrix mineralization disorders such as hypophosphatasia. Additional details of the invention are provided below.

Alkaline Phosphatase

Alkaline phosphatases encompass a group of enzymes that share the property of being able to cleave phosphate in a variety of contexts (e.g., hydrolysis of pyrophosphate, $PP_i$). There are four known mammalian alkaline phosphatase (ALP) isozymes: tissue non-specific alkaline phosphatase (TNALP; described further below), placental alkaline phosphatase (PLALP) (e.g., Accession Nos. P05187, NP_112603, and NP_001623), germ cell alkaline phosphatase (GCALP) (e.g., Accession No. P10696), and intestinal alkaline phosphatase (IALP) (e.g., Accession Nos. P09923 and NP_001622). These isozymes possess very similar three dimensional structures. Each of their catalytic sites contains four metal binding domains that bind to metal ions necessary for enzymatic activity, including two zinc ions and one magnesium ion. These enzymes catalyze the hydrolysis of monoesters of phosphoric acid and also catalyze a transphosphorylation reaction in the presence of high concentrations of phosphate acceptors. It has been shown that PALP is physiologically active toward phosphoethanolamine (PEA), inorganic pyrophosphate ($PP_i$), and pyridoxal 5'-phosphate (PLP), all three being known natural substrate for TNALP (Whyte, 1995). An alignment between these isozymes is shown in FIGS. 4(a)-4(d). Additional alkaline phosphatases are described, e.g., in WO 2008/138131 and in U.S. Publication No. 2006/0014687, which are hereby incorporated by reference.

Tissue non-specific phosphatases are a family of proteins, encoded by a single genes, that differ from each other by post-translational modification. TNALPs are present predominantly in the liver, kidneys, and bone, but can occur throughout the body. Known TNALPs in mammals include, e.g., human TNALP (Accession Nos. NP-000469, AAI10910, AAH90861, AAH66116, AAH21289, and AAI26166); rhesus TNALP (Accession No. XP-001109717); rat TNALP (Accession No. NP_037191); dog TNALP (Accession No. AAF64516; pig TNALP (Accession No. AAN64273), mouse (Accession No. NP_031457), cow TNALP (Accession Nos. NP_789828, NP_776412, AAM 8209, AAC33858), and cat TNALP (Accession No. NP_001036028), in addition to other examples provided herein.

Soluble Alkaline Phosphatase

The soluble alkaline phosphatases (sALP) of the invention include, for example, soluble (e.g., extracellular or non membrane-bound) forms of any of the alkaline phosphatases described herein. The soluble alkaline phosphatase of the invention can be, for example, a soluble form of human TNALP. A schematic representation of the domains of human TNALP (hTNALP) is shown in FIG. 1. TNALP is a membrane-bound protein anchored through a glycolipid bound to its C-terminal (Swiss-Prot, P05186). This glycolipid anchor (GPI) is added post translationally after the removal of a hydrophobic C-terminal end, which serves both as a temporary membrane anchor and as a signal for the addition of the GPI. This GPI anchor is buried in the cell membrane, and the remaining portions of the protein are extracellular. TNALP, including hTNALP, can be engineered to replace the first amino acid of the hydrophobic C-terminal sequence (an alanine) with a stop codon. The engineered hTNALP so formed contains all amino acids of the native anchored form of TNALP but lacks the GPI membrane anchor. An hTNALP which is soluble is herein referred to as "hsTNALP". One skilled in the art will appreciate that the position of the GPI membrane anchor will vary in different alkaline phosphatases and may include, for example, the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. For example, the GPI membrane anchor of the hTNALP of SEQ ID NO: 6 is amino acids 503-524. The amino acid sequence of this hsTNALP (with one variation at position 2), as fused to Fc, is shown in FIG. 2. The sequence of a nucleic acid encoding this hsTNALP-Fc fusion polypeptide is shown in FIG. 6.

In addition to the C-terminal GPI anchor, TNALP also has an N-terminal signal peptide sequence. The N-terminal signal peptide is initially present on the protein when it is synthesized, but is cleaved after translocation into the ER. Thus, the N-terminal signal peptide is absent from the secreted form of TNALP. The sALPs of the invention include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and may include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. For example, the N-terminal signal peptide of the hTNALP of SEQ ID NO: 6 is its first 17 amino acids. Thus, a secreted, soluble form of this hTNALP is amino acids 18-502 of SEQ ID NO: 6 (SEQ ID NO: 5). The amino acid sequence of this secreted hsTNALP, as fused to Fc, is shown in FIG. 3. The sALPs of the invention include both secreted and non-secreted forms thereof. One of skill in the art can predict the position of a signal sequence cleavage site, e.g., by an appropriate computer algorithm such as that described in Bendtsen et al. (*J. Mol. Biol.* 340(4):783-795, 2004) and available on the Web at http://www.cbs.dtu.dk/services/SignalP/.

The sALPs of the invention also include, for example, polypeptide sequences satisfying a consensus sequence derived from the ALP extracellular domain of human ALP isozymes and of mammalian TNALP orthologs (human, mouse, rat, cow, cat, and dog) (SEQ ID NO:15), or a consensus derived from just the ALP extracellular domain of human ALP isozymes (SEQ ID NO:16). The sALPs of the invention also include those which satisfy similar consensus sequences derived various combinations of these TNALP orthologs or human ALP isozymes. Such consensus sequences are given, for example, in WO 2008/138131, herein incorporated by reference.

Furthermore, it has been shown that recombinant hsTNALP retaining original amino acids 1 to 501 (18 to 501 when secreted) (Oda et al., *J. Biochem* 126: 694-699, 1999), amino acids 1 to 502 (18 to 502 when secreted) (WO 2008/138131), amino acids 1 to 504 (18 to 504 when secreted) (U.S. Pat. No. 6,905,689, which is herein incorporated by reference) and amino acids 1 to 505 (18-505 when secreted) (US 2007/0081984, which is herein incorporated by reference), are enzymatically active. This indicates that certain amino acid residues can be truncated from the C-terminal end of the soluble hsTNALP polypeptide without affecting its enzymatic activity. This also indicates that certain amino acids residues of the GPI membrane anchor, when present, do not significantly affect the solubility of the polypeptide. Hence, the sALPs of the invention also include those where, e.g., up to five (e.g., one, two, three, four, or five) amino acid residues are truncated on its C-terminal end, and those where, e.g., up to five (e.g., one, two, three, four, or five) amino acid residues of the GPI membrane anchor are present. For example, non-secreted sALPs of the invention include those containing amino acid residues 1-497, 1-498, 1-499, 1-500, 1-501, 1-502, 1-503, 1-504, 1-505, 1-506 or 1-507 of SEQ ID NO: 6 as well as variants thereof where the amino acid at position 2 is a valine, and secreted sALPs of the invention include those containing amino acid residues 18-497, 18-498, 18-499, 18-500, 18-501, 18-502, 18-503, 18-504, 18-505, 18-506, or 18-507 of SEQ ID NO: 6.

One skilled in the art will appreciate that many mutations in the amino acid sequence of an enzyme will not significantly disrupt the catalytic function of the enzyme. In some cases, certain mutation may even benefit the catalytic function of the enzyme in the context of therapy for matrix mineralization disorders. Therefore, the sALPs of the invention include not only the wild type sequence of the alkaline phosphatases described above, but also include any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases. It is known, however, that specific mutations in TNALP are known to cause HPP. Such pathogenic mutations are preferably absent in the sALPs of the invention. Examples of such mutations are listed below.

In particular, the sALPs of the invention, using the numbering of the consensus sequence of SEQ ID NO:15, the amino acid at position 22 is not a phenylalanine residue; the amino acid at position 33 (position 11 in the sequence without signal peptide) is not a cysteine residue; the amino acid at position 38 (position 16 in the sequence without signal peptide) is not a valine residue; the amino acid at position 42 (position 20 in the sequence without signal peptide) is not a proline residue; the amino acid at position 45 (position 23 in the sequence without signal peptide) is not a valine residue; the amino acid residue at position 56 (position 34 in the sequence without signal peptide) is not a serine or a valine residue; the amino acid residue at position 67 (position 45 in the sequence without signal peptide) is not a leucine, an isoleucine or a valine residue; the amino acid residue at position 68 (position 46 in the sequence without signal peptide) is not a valine residue; the amino acid residue at position 73 (position 51 in the sequence without signal peptide) is not a methionine residue; the amino acid residue at position 76 (position 54 in the sequence without signal peptide) is not a cysteine, a serine, a proline or a histidine residue; the amino acid residue at position 77 (position 55 in the sequence without signal peptide) is not a threonine residue; the amino acid residue at position 80 (position 58 in the sequence without signal peptide) is not a serine residue; the amino acid residue at position 81 (position 59 in the sequence without signal peptide) is not an asparagine residue; the amino acid residue at position 105 (position 83 in the sequence without signal peptide) is not a methionine residue; the amino acid residue at position 113 (position 89 in the sequence without signal peptide) is not a leucine residue; the amino acid residue at position 116 (position 94 in the sequence without signal peptide) is not a threonine residue; the amino acid residue at position 117 (position 95 in the sequence without signal peptide) is not a serine residue; the amino acid residue at position 119 (position 97 in the sequence without signal peptide) is not a glycine residue; the amino acid residue at position 121 (position 99 in the sequence without signal peptide) is not a serine or a threonine residue; the amino acid residue at position 125 (position 103 in the sequence without signal peptide) is not an arginine residue; the amino acid residue at position 128 (position 106 in the sequence without signal peptide) is not a aspartate residue; the amino acid residue at position 133 (position 111 in the sequence without signal peptide) is not a methionine residue; the amino acid residue at position 134 (position 112 in the sequence without signal peptide) is not an arginine residue; the amino acid residue at position 137 (position 115 in the sequence without signal peptide) is not a threonine or a valine residue; the amino acid residue at position 139 (position 117 in the sequence without signal peptide) is not a histidine or an asparagine residue; the amino acid residue at position 141 (position 119 in the sequence without signal peptide) is not a histidine residue; the amino acid residue at position 153 (position 131 in the sequence without signal peptide) is not an alanine or an isoleucine residue; the amino acid residue at position 167 (position 145 in the sequence without signal peptide) is not a serine or a valine residue; the amino acid residue at position 172 (position 150 in the sequence without signal peptide) is not a methionine residue; the amino acid residue at position 175 (position 153 in the sequence without signal peptide) is not an aspartate residue; the amino acid residue at position 176 (position 154 in the sequence without signal peptide) is not a tyrosine or an arginine residue; the amino acid residue at position 181 (position 159 in the sequence without signal peptide) is not a threonine residue; the amino acid residue at position 182 (position 160 in the sequence without signal peptide) is not a threonine residue; the amino acid residue at position 184 (position 162 in the sequence without signal peptide) is not a threonine residue; the amino acid residue at position 186 (position 164 in the sequence without signal peptide) is not a leucine residue; the amino acid residue at position 189 (position 167 in the sequence without signal peptide) is not a tryptophan residue; the amino acid residue at position 194 (position 172 in the sequence without signal peptide) is not a glutamate residue; the amino acid residue at position 196 (position 174 in the sequence without signal peptide) is not a lysine or a glycine residue; the amino acid residue at position 197 (position 175 in the sequence without signal peptide) is not a threonine residue; the amino acid residue at position 198 (position 176 in the sequence without signal peptide) is not an alanine residue; the amino acid residue at position 206 (position 184 in the sequence without signal peptide) is not a tyrosine residue; the amino acid residue at position 208 (position 186 in the sequence without signal peptide) is not a glutamate residue; the amino acid residue at position 207 (position 190 in the sequence without signal peptide) is not a proline residue; the amino acid residue at position 216 (position 194 in the sequence without signal peptide) is not a aspartate residue; the amino acid residue at position 217 (position 195 in the sequence without signal peptide) is not a phenylalanine residue; the amino acid residue at position 223 (position 201 in the sequence without signal peptide) is not a threonine residue; the amino acid residue at position 225 (position 203 in the sequence without signal peptide) is not a valine or an alanine residue; the amino acid residue at position 226 (position 204 in the sequence without signal peptide) is not a valine residue; the amino acid residue at position 228 (position 206 in the sequence without signal peptide) is not a tryptophan or a glutamine residue; the amino acid residue at position 229 (position 207 in the sequence without signal peptide) is not a glutamate residue; the amino acid residue at position 231 (position 209 in the sequence without signal peptide) is not a threonine residue; the amino acid residue at position 240 (position 218 in the sequence without signal peptide) is not a glycine residue; the amino acid residue at position 251 (position 229 in the sequence without signal peptide) is not a serine residue; the amino acid residue at position 254 (position 232 in the sequence without signal peptide) is not a valine residue; the amino acid residue at position 269 (position 247 in the sequence without signal peptide) is not an arginine residue; the amino acid residue at position 277 (position 255 in the sequence without signal peptide) is not a cysteine, a leucine or a histidine residue; the amino acid residue at position 280 (position 258 in the sequence without signal peptide) is not a proline residue; the amino acid residue at position 295 (position 273 in the sequence without signal peptide) is not a phenylalanine residue; the amino acid residue at position 297 (position 275 in the sequence without signal peptide) is not a lysine residue; the amino acid residue at position 298 (position 276 in the sequence without signal peptide) is not a threonine residue; the amino acid residue at position 300 (position 278 in the sequence without signal peptide) is not a tyrosine or an alanine residue; the amino acid residue at position 301 (position 279 in the sequence without signal peptide) is not a valine, a threonine or an isoleucine residue; the amino acid residue at position 303 (position 281 in the sequence without signal peptide) is not an aspirate residue; the amino acid residue at position 304 (position 282 in the sequence without signal peptide) is not a lysine residue; the amino acid residue at position 305 (position 283 in the sequence without signal peptide) is not a praline residue; the amino acid residue at position 312 (position 290 in the sequence without signal peptide) is not a valine residue; the amino acid residue at position 313 (position 291 in the sequence without signal peptide) is not a serine or a leucine residue; the amino acid residue at position 317 (position 295 in the sequence without signal peptide) is not a lysine residue; the amino acid residue at position 332 (position 310 in the sequence without signal peptide) is not an arginine residue; the amino acid residue at position 333 (position 311 in the sequence without signal peptide) is not a cysteine, a glycine or a leucine residue; the amino acid residue at position 334 (position 312 in the sequence without signal peptide) is not a leucine residue; the amino acid residue at position 340 (position 318 in the sequence without signal peptide) is not an aspartate residue; the amino acid residue at position 345 (position 323 in the sequence without signal peptide) is not an arginine or a glutamate residue; the amino acid residue at position 354 (position 332 in the sequence without signal peptide) is not a threonine residue; the amino acid residue at position 360 (position 338 in the sequence without signal peptide) is not an aspartate residue; the amino acid residue at position 361 (position 339 in the sequence without signal peptide) is not a threonine or an isoleucine residue; the amino acid residue at position 377 (position 355 in the sequence without signal peptide) is not a leucine residue; the amino acid residue at position 380 (position 358 in the sequence without signal peptide) is not a methionine residue; the amino acid residue at position 383 (position 361 in the sequence without signal peptide) is not a valine residue; the amino acid residue at position 384 (position 362 in the sequence without signal peptide) is not a valine residue; the amino acid residue at position 387 (position 365 in the sequence without signal peptide) is not an arginine residue; the amino acid residue at position 388 (position 366 in the sequence without signal peptide) is not a leucine residue; the amino acid residue at position 395 (position 373 in the sequence without signal peptide) is not a leucine residue; the amino acid residue at position 397 (position 375 in the sequence without signal peptide) is not a cysteine or a histidine residue; the amino acid residue at position 398 (position 376 in the sequence without signal peptide) is not an alanine residue; the amino acid residue at position 401 (position 379 in the sequence without signal peptide) is not a threonine residue; the amino acid residue at position 405 (position 383 in the sequence without signal peptide) is not a serine or a valine residue; the amino acid residue at position 406 (position 384 in the sequence without signal peptide) is not a leucine residue; the amino acid residue at position 412 (position 390 in the sequence without signal peptide) is not a glycine residue; the amino acid residue at position 416 (position 394 in the sequence without signal peptide) is not a leucine residue; the amino acid residue at position 417 (position 395 in the sequence without signal peptide) is not an alanine residue; the amino acid residue at position 420 (position 398 in the sequence without signal peptide) is not a methionine residue; the amino acid residue at position 423 (position 401 in the sequence without signal peptide) is not a serine residue; the amino acid residue at position 426 (position 404 in the sequence without signal peptide) is not a serine residue; the amino acid residue at position 429 (position 407 in the sequence without signal peptide) is not an alanine residue; the amino acid residue at position 430 (position 408 in the sequence without signal peptide) is not a methionine residue; the amino acid residue at position 432 (position 410 in the sequence without signal peptide) is not a cysteine or an aspartate residue; amino acid residue at position 434 (position 412 in the sequence without signal peptide) is not a proline residue; amino acid residue at position 435 (position 413 in the sequence without signal peptide) is not a lysine residue; amino acid residue at position 442 (position 420 in the sequence without signal peptide) is not a histidine residue; amino acid residue at position 451 (position 429 in the sequence without signal peptide) is not a praline residue; amino acid residue at position 456 (position 434 in the sequence without signal peptide) is not a histidine or a cysteine residue; amino acid residue at position 458 (position 436 in the sequence without signal peptide) is not a lysine residue; amino acid residue at position 460 (position 438 in the sequence without signal peptide) is not an arginine residue; amino acid residue at position 461 (position 439 in the sequence without signal peptide) is not a serine or an aspartate residue; amino acid residue at position 462 (position 440 in the sequence without signal peptide) is not a tryptophan or an arginine residue; amino acid residue at position 465 (position 443 in the sequence without signal peptide) is not a methionine or a leucine residue; amino acid residue at position 472 (position 450 in the sequence without signal peptide) is not a leucine residue; amino acid residue at position 473 (position 451 in the sequence without signal peptide) is not a threonine residue; amino acid residue at position 474 (position 452 in the sequence without signal peptide) is not a threonine residue; amino acid residue at position 479 (position 457 in the sequence without signal peptide) is not a serine residue; amino acid residue at position 482 (position 460 in the sequence without signal peptide) is not a lysine or a glycine residue; amino acid residue at position 484 (position 462 in the sequence without signal peptide) is not a leucine residue; amino acid residue at position 495 (position 473 in the sequence without signal peptide) is not a serine residue; amino acid residue at position 496 (position 474 in the sequence without signal peptide) is not a phenylalanine residue; and amino acid residue at position 497 (position 475 in the sequence without signal peptide) is not an arginine residue.

Also more specifically, when a sTNALP is used in the bone targeted sALPs of the present invention, using the numbering of the human TNALP sequence, the amino acid at position 17 is not a phenylalanine residue; the amino acid at position 28 (position 11 in the sequence without signal peptide) is not a cysteine residue; the amino acid at position 33 (position 16 in the sequence without signal peptide) is not a valine residue; the amino acid at position 37 (position 20 in the sequence without signal peptide) is not a proline residue; the amino acid at position 40 (position 23 in the sequence without signal peptide) is not a valine residue; the amino acid residue at position 51 (position 34 in the sequence without signal peptide) is not a serine or a valine residue; the amino acid residue at position 62 (position 45 in the sequence without signal peptide) is not a leucine, an isoleucine or a valine residue; the amino acid residue at position 63 (position 46 in the sequence without signal peptide) is not a valine residue; the amino acid residue at position 68 (position 51 in the sequence without signal peptide) is not a methionine residue; the amino acid residue at position 71 (position 54 in the sequence without signal peptide) is not a cysteine, a serine, a proline or a histidine residue; the amino acid residue at position 72 (position 55 in the sequence without signal peptide) is not a threonine residue; the amino acid residue at position 75 (position 58 in the sequence without signal peptide) is not a serine residue; the amino acid residue at position 76 (position 59 in the sequence without signal peptide) is not an asparagine residue; the amino acid residue at position 100 (position 83 in the sequence without signal peptide) is not a methionine residue; the amino acid residue at position 108 (position 89 in the sequence without signal peptide) is not a leucine residue; the amino acid residue at position 111 (position 94 in the sequence without signal peptide) is not a threonine residue; the amino acid residue at position 112 (position 95 in the sequence without signal peptide) is not a serine residue; the amino acid residue at position 114 (position 97 in the sequence without signal peptide) is not a glycine residue; the amino acid residue at position 116 (position 99 in the sequence without signal peptide) is not a serine or a threonine residue; the amino acid residue at position 120 (position 103 in the sequence without signal peptide) is not an arginine residue; the amino acid residue at position 123 (position 106 in the sequence without signal peptide) is not a aspartate residue; the amino acid residue at position 128 (position 111 in the sequence without signal peptide) is not a methionine residue; the amino acid residue at position 129 (position 112 in the sequence without signal peptide) is not an arginine residue; the amino acid residue at position 132 (position 115 in the sequence without signal peptide) is not a threonine or a valine residue; the amino acid residue at position 134 (position 117 in the sequence without signal peptide) is not a histidine or an asparagine residue; the amino acid residue at position 136 (position 119 in the sequence without signal peptide) is not a histidine residue; the amino acid residue at position 148 (position 131 in the sequence without signal peptide) is not an alanine or an isoleucine residue; the amino acid residue at position 162 (position 145 in the sequence without signal peptide) is not a serine or a valine residue; the amino acid residue at position 167 (position 150 in the sequence without signal peptide) is not a methionine residue; the amino acid residue at position 170 (position 153 in the sequence without signal peptide) is not an aspartate residue; the amino acid residue at position 171 (position 154 in the sequence without signal peptide) is not a tyrosine or an arginine residue; the amino acid residue at position 176 (position 159 in the sequence without signal peptide) is not a threonine residue; the amino acid residue at position 177 (position 160 in the sequence without signal peptide) is not a threonine residue; the amino acid residue at position 179 (position 162 in the sequence without signal peptide) is not a threonine residue; the amino acid residue at position 181 (position 164 in the sequence without signal peptide) is not a leucine residue; the amino acid residue at position 184 (position 167 in the sequence without signal peptide) is not a tryptophane residue; the amino acid residue at position 189 (position 172 in the sequence without signal peptide) is not a glutamate residue; the amino acid residue at position 191 (position 174 in the sequence without signal peptide) is not a lysine or a glycine residue; the amino acid residue at position 192 (position 175 in the sequence without signal peptide) is not a threonine residue; the amino acid residue at position 193 (position 176 in the sequence without signal peptide) is not an alanine residue; the amino acid residue at position 201 (position 184 in the sequence without signal peptide) is not a tyrosine residue; the amino acid residue at position 203 (position 186 in the sequence without signal peptide) is not a glutamate residue; the amino acid residue at position 207 (position 190 in the sequence without signal peptide) is not a praline residue; the amino acid residue at position 211 (position 194 in the sequence without signal peptide) is not a aspartate residue; the amino acid residue at position 212 (position 195 in the sequence without signal peptide) is not a phenylalanine residue; the amino acid residue at position 218 (position 201 in the sequence without signal peptide) is not a threonine residue; the amino acid residue at position 220 (position 203 in the sequence without signal peptide) is not a valine or an alanine residue; the amino acid residue at position 221 (position 204 in the sequence without signal peptide) is not a valine residue; the amino acid residue at position 223 (position 206 in the sequence without signal peptide) is not a tryptophane or a glutamine residue; the amino acid residue at position 224 (position 207 in the sequence without signal peptide) is not a glutamate residue; the amino acid residue at position 226 (position 209 in the sequence without signal peptide) is not a threonine residue; the amino acid residue at position 235 (position 218 in the sequence without signal peptide) is not a glycine residue; the amino acid residue at position 246 (position 229 in the sequence without signal peptide) is not a serine residue; the amino acid residue at position 249 (position 232 in the sequence without signal peptide) is not a valine residue; the amino acid residue at position 264 (position 247 in the sequence without signal peptide) is not an arginine residue; the amino acid residue at position 272 (position 255 in the sequence without signal peptide) is not a cysteine, a leucine or a histidine residue; the amino acid residue at position 275 (position 258 in the sequence without signal peptide) is not a proline residue; the amino acid residue at position 289 (position 272 in the sequence without signal peptide) is not a phenylalanine residue; the amino acid residue at position 291 (position 274 in the sequence without signal peptide) is not a lysine residue; the amino acid residue at position 292 (position 275 in the sequence without signal peptide) is not a threonine residue; the amino acid residue at position 294 (position 277 in the sequence without signal peptide) is not a tyrosine or an alanine residue; the amino acid residue at position 295 (position 278 in the sequence without signal peptide) is not a valine, a threonine or an isoleucine residue; the amino acid residue at position 297 (position 280 in the sequence without signal peptide) is not an aspirate residue; the amino acid residue at position 298 (position 281 in the sequence without signal peptide) is not a lysine residue; the amino acid residue at position 299 (position 282 in the sequence without signal peptide) is not a proline residue; the amino acid residue at position 306 (position 289 in the sequence without signal peptide) is not a valine residue; the amino acid residue at position 307 (position 290 in the sequence without signal peptide) is not a serine or a leucine residue; the amino acid residue at position 311 (position 294 in the sequence without signal peptide) is not a lysine residue; the amino acid residue at position 326 (position 309 in the sequence without signal peptide) is not an arginine residue; the amino acid residue at position 327 (position 310 in the sequence without signal peptide) is not a cysteine, a glycine or a leucine residue; the amino acid residue at position 328 (position 311 in the sequence without signal peptide) is not a leucine residue; the amino acid residue at position 334 (position 317 in the sequence without signal peptide) is not an aspartate residue; the amino acid residue at position 339 (position 322 in the sequence without signal peptide) is not an arginine or a glutamate residue; the amino acid residue at position 348 (position 331 in the sequence without signal peptide) is not a threonine residue; the amino acid residue at position 354 (position 337 in the sequence without signal peptide) is not an aspartate residue; the amino acid residue at position 355 (position 338 in the sequence without signal peptide) is not a threonine or an isoleucine residue; the amino acid residue at position 371 (position 354 in the sequence without signal peptide) is not a leucine residue; the amino acid residue at position 374 (position 357 in the sequence without signal peptide) is not a methionine residue; the amino acid residue at position 377 (position 360 in the sequence without signal peptide) is not a valine residue; the amino acid residue at position 378 (position 361 in the sequence without signal peptide) is not a valine residue; the amino acid residue at position 381 (position 364 in the sequence without signal peptide) is not an arginine residue; the amino acid residue at position 382 (position 365 in the sequence without signal peptide) is not a leucine residue; the amino acid residue at position 389 (position 372 in the sequence without signal peptide) is not a leucine residue; the amino acid residue at position 391 (position 374 in the sequence without signal peptide) is not a cysteine or a histidine residue; the amino acid residue at position 392 (position 375 in the sequence without signal peptide) is not an alanine residue; the amino acid residue at position 395 (position 378 in the sequence without signal peptide) is not a threonine residue; the amino acid residue at position 399 (position 382 in the sequence without signal peptide) is not a serine or a valine residue; the amino acid residue at position 400 (position 383 in the sequence without signal peptide) is not a leucine residue; the amino acid residue at position 406 (position 389 in the sequence without signal peptide) is not a glycine residue; the amino acid residue at position 410 (position 393 in the sequence without signal peptide) is not a leucine residue; the amino acid residue at position 411 (position 394 in the sequence without signal peptide) is not an alanine residue; the amino acid residue at position 414 (position 397 in the sequence without signal peptide) is not a methionine residue; the amino acid residue at position 417 (position 400 in the sequence without signal peptide) is not a serine residue; the amino acid residue at position 420 (position 403 in the sequence without signal peptide) is not a serine residue; the amino acid residue at position 423 (position 406 in the sequence without signal peptide) is not an alanine residue; the amino acid residue at position 424 (position 407 in the sequence without signal peptide) is not a methionine residue; the amino acid residue at position 426 (position 409 in the sequence without signal peptide) is not a cysteine or an aspartate residue; amino acid residue at position 428 (position 411 in the sequence without signal peptide) is not a proline residue; amino acid residue at position 429 (position 412 in the sequence without signal peptide) is not a lysine residue; amino acid residue at position 436 (position 419 in the sequence without signal peptide) is not a histidine residue; amino acid residue at position 445 (position 428 in the sequence without signal peptide) is not a proline residue; amino acid residue at position 450 (position 433 in the sequence without signal peptide) is not a histidine or a cysteine residue; amino acid residue at position 452 (position 435 in the sequence without signal peptide) is not a lysine residue; amino acid residue at position 454 (position 437 in the sequence without signal peptide) is not an arginine residue; amino acid residue at position 455 (position 438 in the sequence without signal peptide) is not a serine or an aspartate residue; amino acid residue at position 456 (position 439 in the sequence without signal peptide) is not a tryptophane or an arginine residue; amino acid residue at position 459 (position 442 in the sequence without signal peptide) is not a methionine or a leucine residue; amino acid residue at position 466 (position 449 in the sequence without signal peptide) is not a leucine residue; amino acid residue at position 467 (position 450 in the sequence without signal peptide) is not a threonine residue; amino acid residue at position 468 (position 451 in the sequence without signal peptide) is not a threonine residue; amino acid residue at position 473 (position 456 in the sequence without signal peptide) is not a serine residue; amino acid residue at position 476 (position 459 in the sequence without signal peptide) is not a lysine or a glycine residue; amino acid residue at position 478 (position 461 in the sequence without signal peptide) is not a leucine residue; amino acid residue at position 489 (position 472 in the sequence without signal peptide) is not a serine residue; amino acid residue at position 490 (position 473 in the sequence without signal peptide) is not a phenylalanine residue; and amino acid residue at position 491 (position 474 in the sequence without signal peptide) is not an arginine residue. In other specific embodiments, one or more Xs are defined as being any of the amino acids found at that position in the sequences of the alignment or a residue that constitutes a conserved or semi-conserved substitution of any of these amino acids. In other specific embodiments, Xs are defined as being any of the amino acids found at that position in the sequences of the alignment. For instance, the amino acid residue at position 51 (position 34 in the sequence without signal peptide) is an alanine or a valine residue; the amino acid residue at position 177 (position 160 in the sequence without signal peptide) is an alanine or a serine residue; the amino acid residue at position 212 (position 195 in the sequence without signal peptide) is an isoleucine or a valine residue; the amino acid residue at position 291 (position 274 in the sequence without signal peptide) is a glutamic acid or an aspartic acid residue; and the amino acid residue at position 374 (position 357 in the sequence without signal peptide) is a valine or an isoleucine residue.

Fragment Crystallizable Region (Fc) Fragments

The fusion polypeptides of the invention may include a C-terminal domain such as Fc, a fragment crystallizable region of an immunoglobulin. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the $V_H$ and $C_{H1}$ domains of the heavy chain) and Fc (containing the $C_{H2}$ and $C_{H3}$ domains of the heavy chain, along with adjoining sequences). Cleavage typically occurs in a flexible hinge region joining the Fab and Fc regions. For example, papain cleaves the hinge region immediately before the disulfide bonds joining the two heavy chains.

Useful Fc fragments of the invention include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), taken from any mammal (e.g., human). The Fc fragments of the invention include, for example, the $C_{H2}$ and $C_{H3}$ domains of the heavy chain, as well as any portion of the hinge region. Furthermore, the Fc region can be glycosylated at various amino acid residues known to those skilled in the art. In some embodiments, the Fc fragment is of human IgG-1. In particular embodiments, the Fc fragment of the fusion polypeptide has the amino acid sequence of SEQ ID NO: 3, or has at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to SEQ ID NO: 3.

Additional Polypeptide Features

The polypeptides of the invention optionally include one or more additional amino acids 1) at the N-terminus of the polypeptide 2) between the sALP and Fc regions of the polypeptide, and 3) at the C-terminus of the polypeptide. Thus, the invention includes, for example, polypeptides of the form Z-sALP-Y-Fc-X or Z-Fc-Y-sALP-X, where Z is one or more (e.g., 2, 3, 4, 5, 6, 7, 8, 9, 10, 11, 12, 13, 14, 15, 17, 20, 25, 30, 35, 40, 45, 50, or more) additional amino acids at the N-terminus of the polypeptide, Y is one or more (e.g., 2, 3, 4, 5, 6, 7, 8, 9, 10, 11, 12, 13, 14, 15, 17, 20, 25, 30, 35, 40, 45, 50, or more) additional amino acids (i.e., a linker) between the sALP and Fc regions of the polypeptide, and X is one or more (e.g., 2, 3, 4, 5, 6, 7, 8, 9, 10, 11, 12, 13, 14, 15, 17, 20, 25, 30, 35, 40, 45, 50, or more) additional amino acids at the C-terminus of the polypeptide. In a particular example, Y is the dipeptide leucine-lysine. Alternatively, any combination of X, Y, and Z may be present or absent. For example, in some embodiments, Z and X are both absent, and Y is absent or is an amino acid sequence of at least one amino acid. For example, the polypeptide may consist of the structure sALP-Y-Fc or the structure Fc-Y-sALP. In some embodiments of polypeptides consisting of the structure sALP-Y-Fc or Fc-Y-sALP, Y may consist of two amino acid residues, e.g., leucine-lysine. For example, the polypeptide may consist of the structure sALP-Y-Fc. Optionally, the amino acid sequence of sALP is the amino acid sequence of SEQ ID NO: 5, the amino acid sequence of Y is leucine-lysine, and/or the amino acid sequence of Fc is the amino acid sequence of SEQ ID NO: 3. In some embodiments, the amino acid sequence of the polypeptide consists of the amino acid sequence of SEQ ID NO: 4.

In some embodiments, additional amino acids can be introduced into the polypeptide according to the cloning strategy used to produce the fusion polypeptides. In some embodiments, the additional amino acids do not provide an additional GPI anchoring signal so as to maintain the polypeptide in a soluble form. Furthermore, in some embodiments, any such additional amino acids, when incorporated into the polypeptide of the invention, do not provide a cleavage site for endoproteases of the host cell. The likelihood that a designed sequence would be cleaved by the endoproteases of the host cell can be predicted as described, e.g., by Ikezawa (Biol. Pharm. Bull. 25:409-417, 2002).

The polypeptides of the invention also include any polypeptide having one or more post-translational modifications such as glycosylation (e.g., mannosylation and other forms of glycosylation discussed herein), acetylation, amidation, blockage, formylation, gamma-carboxyglutamic acid hydroxylation, methylation, ubiquitination, phosphorylation, pyrrolidone carboxylic acid modification, and sulfation.

In certain embodiments, the polypeptides of the invention are associated into dimers or tetramers. For example, two sALP-Fc monomers can covalently linked through two disulfide bonds located in the hinge regions of the Fc fragments.

Production of Nucleic Acids and Polypeptides

The nucleic acids and polypeptides of the invention can be produced by any method known in the art. Typically, a nucleic acid encoding the desired fusion protein is generated using molecular cloning methods, and is generally placed within a vector, such as a plasmid or virus. The vector is used to transform the nucleic acid into a host cell appropriate for the expression of the fusion protein. Representative methods are disclosed, for example, in Maniatis, et al. (Cold Springs Harbor Laboratory, 1989). Many cell types can be used as appropriate host cells, although mammalian cells are preferable because they are able to confer appropriate post-translational modifications. For example, Chinese Hamster Ovary (CHO) cells have been used as a host for expressing the fusion proteins of the present invention, as described in more detail in the examples below. Other host cells useful for expressing the fusion proteins of the invention include, for example, L cells, C127 cells, 3T3 cells, BHK cells, or COS-7 cells. Particular CHO cells of interest for expressing the fusion proteins of the present invention include CHO-DG44 and CHO/dhfr⁻. This latter cell line is available through the American Type Culture Collection (ATCC number CRL-9096).

The polypeptides of the invention can be produced under any conditions suitable to effect expression of the polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12 and IMDM supplemented with 2-4 mM L-glutamine and 5% Fetal bovine serum; regular commercially available animal protein free media like Hyclone™ SFM4CHO, Sigma CHO DHFR⁻, Cambrex POWER™ CHO CD supplemented with 2-4 mM L-glutamine. These media are desirably prepared without thymidine, hypoxanthine and L-glycine to maintain selective pressure, allowing stable protein-product expression.

Additional details of the production of the polypeptides and nucleic acids of the invention are given in the Examples.

Therapeutic Applications

The nucleic acids and polypeptides of the invention can have a wide variety of therapeutic applications, e.g., in the fields of congenital bone disease, fracture repair, bone and dental implants, vertebrae fusion, and others. In particular, the nucleic acids and polypeptides of the invention are useful for the treatment of matrix mineralization disorders, as described herein, such as HPP.

Hypophosphatasia (HPP)

HPP is historically classified according to age at diagnosis and includes (in order from most severe to least severe) perinatal, infantile, childhood, adult, and odontohypophosphatasia forms. The most severe form, perinatal (lethal) HPP, is manifest as an almost complete absence of bone mineralization in utero and can cause stillbirth. Some neonates with perinatal HPP may survive for several days, but suffer increased respiratory compromise due to hypoplastic and rachitic disease of the chest. In infantile HPP, diagnosed before 6 months-of-age, postnatal development seems normal until the onset of poor feeding, inadequate weight gain, and appearance of rickets. Infantile HPP has characteristic radiological features showing impaired skeletal mineralization, sometimes with progressive skeletal demineralization leading to rib fractures and chest deformity. Childhood HPP has highly variable clinical expression. One symptom of childhood HPP is the premature loss of deciduous teeth resulting from aplasia, hypoplasia or dysplasia of dental cementum that connects the tooth root with the periodontal ligament. Another symptom of childhood HPP is rickets, which causes short stature and skeletal deformities such as bowed legs and enlarged wrists, knees and ankles as a result of flared metaphysis. Adult HPP usually presents during middle age, but is frequently preceded by a history of rickets and/or early loss of teeth followed by good health during adolescence and young adult life. In adult HPP, recurrent metatarsal stress fractures are common, and calcium pyrophosphate dihydrate deposition can cause attacks of arthritis and pyrophosphate arthropathy. Finally, odontohypophosphatasia is diagnosed when the only clinical abnormality is dental disease, and radiological studies and even bone biopsies reveal no signs of rickets or osteomalacia.

The more severe clinical forms of HPP are usually inherited as autosomal recessive traits, with parents of such patients showing subnormal levels of serum AP activity. For the milder forms of HPP, i.e., adult HPP and odontohypophosphatasia, an autosomal dominant pattern of inheritance has also been documented.

In the healthy skeleton, TNALP is an ectoenzyme present on the surface of the plasma membrane of osteoblasts and chondrocytes, and on the membranes of their shed matrix vesicles (MVs), where the enzyme is particularly enriched. Deposition of hydroxyapatite during bone mineralization normally initiates within the lumen of these MVs. Electron microscopy has shown that TNALP-deficient MVs from severely affected HPP patients and Akp2⁻/⁻ mice (a TNALP null mouse model, see below) contain hydroxyapatite crystals, but that extravesicular crystal propagation appears retarded. This defect is attributed to the extracellular accumulation of $PP_i$, a potent inhibitor of calcification, due to a deficiency of TNALP activity.

At physiological concentrations (0.01-0.1 mM), $PP_i$ has the ability to stimulate mineralization. This has been demonstrated in organ-cultured chick femurs and in isolated rat MVs. However, at concentrations above 1 mM, $PP_i$ inhibits calcium phosphate mineral formation by coating hydroxyapatite crystals, thus preventing mineral crystal growth and proliferative self-nucleation. Thus, $PP_i$ has a dual physiological role: it functions as a promoter of mineralization at low concentrations but as an inhibitor of mineralization at higher concentrations. TNALP has been shown to hydrolyze the mineralization inhibitor $PP_i$ to facilitate mineral precipitation and growth. Recent studies using the $Akp2^{-/-}$ mice have indicated that the primary role of TNALP in vivo is to restrict the size of the extracellular $PP_i$ pool to allow proper skeletal mineralization.

The severity of hypophosphatasia depends on the nature of the TNALP mutation. Missense mutations at a variety of positions in TNALP, including the enzyme's active site vicinity, homodimer interface, crown domain, amino-terminal arm, and calcium-binding site, have all been found to affect its catalytic activity. In addition, missense, nonsense, frame-shift, and splice site mutations have also been shown to lead to aberrant mutant proteins or intracellular trafficking defects that lead to subnormal activity on the cell surface. The multitude of mutations that cause HPP, and the fact that compound heterozygosity is a common occurrence in HPP, explain the variable expressivity and incomplete penetrance often observed in this disease.

Progress on the human form of HPP has benefited greatly from the existence of the TNALP null mice ($Akp2^{-/-}$), an animal model of HPP. $Akp2^{-/-}$ mice phenocopy infantile HPP remarkably well: they are born with a normally mineralized skeleton but develop radiographically apparent rickets at about 6 days of age, and die between days 12-16 suffering severe skeletal hypomineralization and episodes of apnea and epileptic seizures attributable to disturbances in PLP (vitamin $B_6$) metabolism.

Both $PP_i$ and PLP are confirmed natural substrates of TNALP, and some TNALP active site mutations have been shown to have different effects on the ability of the enzyme to metabolize $PP_i$ and PLP. Abnormalities in PLP metabolism explain the epileptic seizures observed in $Akp2^{-/-}$ mice, while abnormalities in $PP_i$ metabolism explain the skeletal phenotype in this mouse model of HPP.

Formulation

Formulation will depend on the route of administration, as well as on other therapeutic goals. The nucleic acids and polypeptides of the invention can be administered by any route known in the art, e.g., subcutaneous (e.g., by subcutaneous injection), intravenously, orally, nasally, intramuscularly, sublingually, intrathecally, or intradermally. By way of example, pharmaceutical compositions of the invention can be in the form of a liquid, solution, suspension, pill, capsule, tablet, gelcap, powder, gel, ointment, cream, nebulae, mist, atomized vapor, aerosol, or phytosome.

In some embodiments of the invention, the compositions of the invention can be administered subcutaneously. Subcutaneous administration is advantageous because it is relatively non-invasive and offers desirable pharmacokinetic profiles. Suitable volumes are known to those skilled in the art, and are typically 5 mL or smaller (e.g., 4 mL, 3.5 mL, 3 mL, 2.7 mL, 2.5 mL, 2.3 mL, 2.2 mL, 2.1 mL, 2.0 mL, 1.9 mL, 1.8 mL, 1.7 mL, 1.5 mL, 1.3 mL, 1.0 mL, 0.7 mL, 0.5 mL, 0.3 mL, 0.1 mL, 0.05 mL, 0.01 mL, or smaller). The small volumes required for subcutaneous administration require a sufficiently high concentration of the composition to be administered. Thus, not all compositions may be suitable for subcutaneous administration, e.g., polypeptides which aggregate at high concentrations. It has been found that the compositions of the invention can be formulated in a sufficiently high concentration as to be suitable for subcutaneous administration. Typically, the compositions of the invention can be formulated at a concentration between, e.g., 1 mg/mL and 500 mg/mL (e.g., between 10 mg/mL and 300 mg/mL, 20 mg/mL and 120 mg/mL, 40 mg/mL and 200 mg/mL, 30 mg/mL and 150 mg/mL, 40 mg/mL and 100 mg/mL, 50 mg/mL and 80 mg/mL, or 60 mg/mL and 70 mg/mL) for subcutaneous administration.

For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Compositions of the invention for oral administration also can contain pharmaceutically acceptable excipients such as suspending agents, emulsifying agents, non-aqueous vehicles, preservatives, buffer salts, flavoring, coloring, and sweetening agents as appropriate. Preparations for oral administration also can be suitably formulated to give controlled release of the active ingredients.

Enteric coatings can further be used on tablets of the present invention to resist prolonged contact with the strongly acidic gastric fluid, but dissolve in the mildly acidic or neutral intestinal environment. Without being so limited, cellulose acetate phthalate, Eudragit™ and hydroxypropyl methylcellulose phthalate (HPMCP) can be used in enteric coatings of pharmaceutical compositions of the present invention. Cellulose acetate phthalate concentrations generally used are 0.5-9.0% of the core weight. The addition of plasticizers improves the water resistance of this coating material, and formulations using such plasticizers are more effective than when cellulose acetate phthalate is used alone. Cellulose acetate phthalate is compatible with many plasticizers, including acetylated monoglyceride; butyl phthalybutyl glycolate; dibutyl tartrate; diethyl phthalate; dimethyl phthalate; ethyl phthalylethyl glycolate; glycerin; propylene glycol; triacetin; triacetin citrate; and tripropionin. It is also used in combination with other coating agents such as ethyl cellulose, in drug controlled-release preparations.

The compounds of the invention may be administered in combination with pharmaceutically acceptable, sterile, aqueous or non-aqueous solvents, suspensions or emulsions. Examples of nonaqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

In some embodiments, the pharmaceutical compositions of the present invention can be delivered in a controlled release system. In some embodiments, polymeric materials including polylactic acid, polyorthoesters, cross-linked amphipathic block copolymers and hydrogels, polyhydroxy butyric acid and polydihydropyrans can be used (see also Smolen and Ball, Controlled Drug Bioavailability, Drug product design and performance, 1984, John Wiley & Sons; Ranade and Hollinger, Drug Delivery Systems, pharmacology and toxicology series, 2003, 2nd edition, CRRC Press). In another embodiments, a pump may be used (Saudek et al., 1989, N. Engl. J. Med. 321: 574).

The compositions of the invention could be formulated in the form of a lyophilized powder using appropriate excipient solutions (e.g., sucrose) as diluents.

Furthermore, cells (e.g., osteoblasts) can be isolated from an individual having a matrix mineralization disorder, transformed with a nucleic acid of the invention, and reintroduced to the afflicted individual (e.g., subcutaneous or intravenous injection). Alternatively, the nucleic acid can be administered directly to the afflicted individual, for example, by injection. The nucleic acid can also be delivered through a vehicle such as a liposome, which can be designed to be targeted to a specific cell type, and engineered to be administered through different routes.

The compositions of the present invention may also be used in combination with at least one other active ingredient to correct a bone mineralization defect or another detrimental symptom of HPP. For example, it may also be used in combination with at least one other active ingredient to correct a cementum defect.

Gene Therapy

The fusion proteins of the present invention could also be advantageously delivered through gene therapy, where an exogenous nucleic acid encoding the proteins is delivered to tissues of interest and expressed in vivo. Gene therapy methods are discussed, e.g., in Verme et al. (*Nature* 389: 239-242, 1997) and Yamamoto et al. (*Molecular Therapy* 17:S67-S68, 2009), which are hereby incorporated by reference. Both viral and non-viral vector systems can be used. The vectors may be, for example, plasmids, artificial chromosomes (e.g., bacterial, mammalian, or yeast artificial chromosomes), virus or phage vectors provided with an origin of replication, and optionally, a promoter for the expression of the nucleic acid encoding the viral polypeptide and optionally, a regulator of the promoter. The vectors may contain one or more selectable marker genes, for example, an ampicillin or kanamycin resistance gene in the case of a bacterial plasmid or a restistance gene for a fungal vector. Vectors may be used in in vitro, for example, for the production of DNA, RNA, or the viral polypeptide, or may be used to transfect or transform a host cell, for example, a mammalian host cell, e.g., for the production of the viral polypeptide encoded by the vector. The vectors may also be adapted to be used in vivo, for example, in a method of vaccination or gene therapy.

Examples of suitable viral vectors include, retroviral, lentiviral, adenoviral, adeno-associated viral, herpes viral, including herpes simplex viral, alpha-viral, pox viral, such as Canarypox and vaccinia-viral based systems. Gene transfer techniques using these viruses are known in the art. Retrovirus vectors, for example, may be used to stably integrate the nucleic acids of the invention into the host genome. Replication-defective adenovirus vectors by contrast remain episomal and therefore allow transient expression. Vectors capable of driving expression in insect cells (e.g., baculovirus vectors), in human cells, yeast, or in bacteria may be employed in order to produce quantities of the viral polypeptide(s) encoded by the nucleic acids of the invention, for example, for use in subunit vaccines or in immunoassays. Useful gene therapy methods include those described in WO 06/060641, U.S. Pat. No. 7,179,903 and WO 01/36620 (each of which is hereby incorporated by reference), which use an adenovirus vector to target a nucleic acid of interest to hepatocytes as protein producing cells.

In an additional example, a replication-deficient simian adenovirus vector may be used as a live vector. These viruses contain an E1 deletion and can be grown on cell lines that are transformed with an E1 gene. Examples of these replication-deficient simian adenovirus vectors are described in U.S. Pat. No. 6,083,716 and WO 03/046124 (each of which is hereby incorporated by reference). These vectors can be manipulated to insert a nucleic acid of the invention, such that the encoded viral polypeptide(s) may be expressed.

Promoters and other expression regulatory signals may be selected to be compatible with the host cell for which expression is designed. For example, mammalian promoters include the metallothionein promoter, which can be induced in response to heavy metals such as cadmium, and the β-actin promoter. Viral promoters, such as the SV40 large T antigen promoter, human cytomegalovirus (CMV) immediate early (IE) promoter, rous sarcoma virus LTR promoter, adenovirus promoter, or a HPV promoter, particularly the HPV upstream regulatory region (URR) may also be used. All these promoters, as well as additional promoters, are well-described in the art.

The nucleic acid(s) of the invention may also be administered using non-viral based systems. For example, these administration systems include microsphere encapsulation, poly(lactide-co-glycolide), nanoparticle, and liposome-based systems. Non-viral based systems also include techniques facilitating the delivery of "naked" polynucleotides (such as electroporation, "gene gun" delivery and various other techniques used for the introduction of polynucleotides).

The introduced polynucleotide can be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome.

Dosage

Any amount of a pharmaceutical composition of the invention can be administered to a subject. The dosages will depend on many factors including the mode of administration and the age of the subject. Typically, the amount the composition of the invention contained within a single dose will be an amount that is effective to treat a mineral mineralization disorder without inducing significant toxicity. For subcutaneous administration, the polypeptides of the invention can be administered to subjects in individual doses ranging from 0.01 mg/kg to 100 mg/kg (e.g., from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg). The doses can be administered hourly, bihourly, daily, bidaily, twice a week, three times a week, four times a week, five times a week, six times a week, weekly, biweekly, monthly, bimonthly, or yearly. The amount and frequency of dosage will be adapted by the clinician in accordance with conventional factors such as the extent of the disease and different parameters from the subject.

The nucleic acids of the invention can be administered according the formulations described herein to a patient in dosages suitable for gene therapy. The amount of the nucleic acids administered will depend on a number of factors known to those skilled in the art, including: the length and nature of the nucleic acid, the vector (e.g., viral or non-viral) used, the activity of the polypeptide encoded, the presence of excipients, the route and method of administration, and the general condition and fitness of the subject. Exemplary dosages and routes of administration are described, e.g., in Melman et al. (*Isr. Med. Assoc. J.* 9:143-146, 2007; describing the intrapenile injection of 0.5 mg to 7.5 mg of a human cDNA in a plasmid for treating erectile dysfunction), Powell et al. (*Circulation* 118:58-65, 2008; describing the intramuscular injection of 0.4 mg to 4.0 mg of a hepatocyte growth factor plasmid to treat critical limb ischemia, Waddill et al. (*AJR Am. J. Roentgenol.* 169:63-67, 1997; describing the CT-guided intratumoral injection of 0.01 mg to 0.25 mg of plasmid DNA encoding an MHC antigen to treat melanoma), Kastrup et al. (*J. Am. Coll. Cardiol.* 45:982-988, 2005; describing the intramyocardial injection of 0.5 mg of a VEGF plasmid to treat severe angina pectoris), Romero et al. (*Hum. Gene. Ther.* 15:1065-1076, 2004; describing the intramuscular injection of 0.2 mg to 0.6 mg of a plasmid to treat Duchenne/Becker muscular dystrophy), each of which is hereby incorporated by reference.

In certain embodiments, the nucleic acids of the invention can be administered to the subject at a dose in the range from, e.g., 0.01 mg to 100 mg (e.g., from 0.05 mg to 50 mg, 0.1 mg to 10 mg, 0.3 mg to 3 mg, or about 1 mg) of nucleic acid. The total volume at which the nucleic acid can be administered will depend on its concentration, and can range from, e.g., 1 µL to 10 mL (e.g. from 10 µL to 1 mL, 50 µL to 500 µL, 70 µL to 200 µL, 90 µL to 150 µL, or 100 µl, to 120 µL). The nucleic acids can be administered in single or multiple doses (e.g., hourly, bihourly, daily, bidaily, twice a week, three time per week, four times a week, five times a week, six times a week, weekly, biweekly, monthly, bimonthly, or yearly).

These are guidelines, since the actual dose should be carefully selected and titrated by an attending physician or nutritionist based upon clinical factors unique to each subject. The optimal daily dose will be determined by methods known in the art and will be influenced by factors such as the age of the subject, as indicated above, and other clinically relevant factors. In addition, subjects may be taking medications for other diseases or conditions. The other medications may be continued during the time that a polypeptide or nucleic acid of the invention is given to the subject, but it is advisable in such cases to begin with low doses to determine if adverse side effects are experienced.

EXAMPLES

The examples provided below describe the successful treatment of Akp2$^{-/-}$ mice using a novel, soluble recombinant protein that includes human tissue-nonspecific alkaline phosphatase that is fused at its carboxy-terminus to a crystalline fragment (Fc) region of human IgG-1. These examples are intended to illustrate the invention, not limit it.

Example 1

Expression and Production of sALP-Fc sALP-Fc cDNA was generated by PCR amplification from pIRES-sALP-FcD10 plasmid, and cloned into the pSV (Hygromycin) expression vector (Selexis Inc.). CHO-K1 S cells grown in Power CHO2 CD media (Lonza) supplemented with 4 mM L-glutamine (Wisent) were transfected with PvuI-linearized pSV-sALP-Fc plasmid using the manufacturer's protocol. Forty-eight hours after transfection, media was replaced with media containing 200 µg/mL hygromycin B (Invitrogen). Viability was monitored and media was replaced every 96 hours. Once viability attained 90%, culture was screened for high expression clones using Clonepix FL technology platform (Genetix Inc.) using a FITC-coupled anti-sALP antibody. Best clones were amplified and selected in 96-well plates using sALP enzymatic assay on culture supernatant. Selected clones were amplified and grown in 25 L WAVE bioreactor. At the end of the culture, the concentration of sALP-Fc in the spent medium was 135 mg/L as assessed by TNSALP enzymatic activity. When viability dropped below 10%, WAVE motion was stopped to allow cells to settle, and supernatant was harvested by filtration through both Millistak+ Pod (Millipore) and 0.22 µm 1 L sterile filter units (Corning). After 10-fold concentration and dialysis of the media in PBS to 2.5 L using tangential flow filtration through Kvick Lab SCU unit (GE Healthcare, 30 kDa cutoff), media was loaded on a Mab Select Sure column that was previously equilibrated with EQ buffer (50 mM NaPO$_4$, 100 mM NaCl, pH 7.5). Column was then washed with 3.5 volumes of EQ buffer, 5.5 volumes of Wash2 buffer (50 mM Tris-Cl, 1.5 M NaCl, pH 8.0), and 3.5 volumes of Wash3 buffer (50 mM Tris-Cl, pH 8.0). sALPFc was then eluted in 10 volumes of Elution buffer (50 mM Tris-Cl, pH 11.0). Eluted protein was further purified on Butyl-sepharose column using the following procedure: Protein was first mixed with an equal volume of 2× equilibration buffer (eq) (40 mM Hepes, 2.5 M ammonium sulfate, pH 7.5), and then loaded on the column which was previously equilibrated in 6 volumes of 1× equilibration buffer. After washing in 5 volumes of eq buffer and 3 volumes of wash2 buffer (20 mM Hepes, 0.95 ammonium sulfate, pH 7.5), protein was eluted in 5 volumes of elution buffer (25 mM NaPO$_4$, 0.5 M ammonium sulfate, pH 7.4). Purified sALP-Fc was finally concentrated and dialysed against phosphate buffer (25 mM NaPO$_4$, 150 mM NaCl, pH 7.4) using 30 kDa cutoff Vivaspin units (Sartorius VS2022). The overall yield of the purification procedure was 30%, with purity surpassing 95% as assessed by Sypro ruby stained 4-12% SDS-PAGE (Invitrogen Inc.) and size exclusion HPLC. Purified sALP-Fc preparations were stored at 4° C. and remained stable for several months.

Example 2

Papain digestion to generate sALP sALP was generated from sALP-Fc using papain digestion as follows: sALP-Fc was first dialyzed against Digestion buffer (20 mM sodium phosphate, pH 7.0) using Vivaspin units (Sartorius VS2022), adjusted to 10 mg/mL, and added to Eppendorf tubes at 600 µL per tube. In parallel, papain-agarose (Sigma P4406) was resuspended in Wash buffer (20 mM sodium phosphate, 1 mM EDTA, pH 6.9) at 25 units in 1.5 mL. To digest 1 nmol of sALPFc, 42 mU of papain-agarose was transferred to a conical tube, centrifuged for 5 min at 1000 g and washed with 10 volumes of Digestion buffer. After another spin down, the beads were resuspended in Digestion buffer and adjusted to the same total volume as prepared sALPFc. Papain was then activated by adding 10 mM DTT to have a final concentration of 0.5 mM. 600 µL of papain-agarose was then immediately added to each Eppendorf containing sALPFc which was pre-heated at 37° C., and incubated for 2 hours at 37° C. with mild agitation. The mix was then poured onto empty PD-10 columns (GE Healthcare 17-0435-01) and flow-through was collected. Gel was rinsed with 3 volumes of Digestion buffer and this volume was pooled with the flow-through. The Fc region was then separated from sALP by purification on Hitrap protein A Mab Select SuRe column (GE Healthcare 11-0034-9) connected to an AKTAfplc system. Briefly, column was equilibrated with 10 volumes of buffer A (10 mM sodium phosphate, 150 mM NaCl, pH 7.4), and protein was loaded at 1 mL/min for a 5 mL column. The flow-through containing sALP was collected in one fraction. Column was then washed (1 mL/min) with buffer A until 280 nm absorbance returned to baseline. This wash was collected in one fraction. Column was then washed at 1.5 mL/min with at least 3 column volumes of buffer B (50 mM Tris-Cl, pH 8.0), and eluted in buffer C (50 mM Tris-Cl, pH 11.0) until 280 nm absorbance returned to baseline. Flow-through and buffer A wash fractions were pooled and dialyzed against storage buffer (25 mM sodium phosphate, 150 mM NaCl, pH 7.4) using Vivaspin units (Sartorius VS2022). Protein concentration was determined using 280 nm optical density assay, and efficiency of digestion and yield were determined using SDS-PAGE analysis, SEC-HPLC, and sALP enzymatic activity assay.

Example 3

Pharmacokinetic Analysis of sALP and sALP-Fc

In vivo pharmacokinetic (PK) studies were performed on purified sALP and sALP-Fc, which were administered intravenously (IV) and subcutaneously (SC) to 5-6 week old C57BL/6 male mice.

Experimental Design

Animals received a single IV or SC dose as described in Table 1.

TABLE 1

Experimental design of an in vivo PK study of sALP and sALP-Fc in mice

| Group No. | Group Description | Dose Level (U/kg) | PK Time points | Animals No. Males |
|---|---|---|---|---|
| 1 | sALP IV | 10000 | 0.5, 4 and 26 hr post dose | 101, 102, 103 |
| | | | 1, 8 and 32 hr post dose | 104, 105, 106 |
| | | | 2, 12 and 49 hr post dose | 107, 108, 109 |
| | | | 21 and 45 hr post dose | 110, 111, 112 |
| 2 | sALP SC | 10000 | 4, 6 and 26 hr post dose | 201, 202, 203 |
| | | | 1, 8 and 32 hr post dose | 204, 205, 206 |
| | | | 2, 12 and 49 hr post dose | 207, 208, 209 |
| | | | 21 and 45 hr post dose | 210, 211, 212 |
| 3 | sALP-Fc IV | 2000 | 0.5, 26 and 96 hr post dose | 101, 102, 103 |
| | | | 1, 8 and 49 hr post dose | 104, 105, 106 |
| | | | 3, 12 and 32 hr post dose | 107, 108, 109 |
| | | | 21, 45 and 72 hr post dose | 110, 111, 112 |
| 4 | sALP-Fc SC | 2000 | 6, 26 and 96 hr post dose | 201, 202, 203 |
| | | | 1, 8 and 49 hr post dose | 204, 205, 206 |
| | | | 3, 12 and 32 hr post dose | 207, 208, 209 |
| | | | 21, 45 and 72 hr post dose | 210, 211, 212 |

Administration of Test Article Dose Formulation

Dose administrations were performed between 7:00 am and 10:30 am. Each mouse was injected with test article subcutaneously into the scapular region or immobilized in a rodent restrainer and injected with the test article as an intravenous bolus via the caudal vein. The dose volume was set at 3.33-4.0 mL/kg. The animals received only one dose before scheduled blood collection and sacrifice. Individual body weights were assessed before scheduled test article injection and the volume of test article administered was based on this body weight determination.

Blood Sampling and Conditioning

Blood samples (0.1 to 0.12 mL) were collected via a jugular vein under isoflurane anesthesia at different time points. At the last time point, blood samples were collected by cardiac puncture under isoflurane anesthesia. Blood samples were collected into Microvette 200Z/gel tube (Sarstedt, serum/gel clotting activator, #20.1291), incubated at room temperature for 30 to 60 min and centrifuged at 10 000 g for 5 min at 2-8° C. Serum was transferred into a fresh 0.5 mL tube (Sarstedt, #72.699), snap-frozen in liquid nitrogen and stored at −80° C. until analysis.

Test Article Concentration in Serum

The presence of sALP and sALP-Fc in serum samples was assessed upon completion of treatment using a colorimetric enzymatic assay. Enzymatic activity was determined using a chromogenic substrate where increase of absorbance is proportional to substrate conversion to products. Final volume was 200 μL. First, 20 μL of standard or 20 μL of PK serum sample was added. A blank was prepared in duplicate also. The reaction was carried out in 180 μL of buffer (20 mM Bis Tris Propane (HCl) pH 9.0, 50 mM NaCl, 0.5 mM $MgCl_2$ and 50 μM $ZnCl_2$) containing 1 mM of substrate (pNPP: para-nitrophenyl phosphate disodium hexahydrate). The latter was added last to initiate the reaction. The absorbance was recorded at 405 nm every 30 seconds over a twenty minutes period on a spectrophotometric plate reader (Molecular Devices). Enzymatic activity expressed as an initial speed rate was assessed by fitting the steepest slope over 20 adjacent readings on the spectrophotometric plate reader.

Standards of known concentrations of sALP or sALP-Fc were prepared and the enzymatic activity was determined as described above. The standard curve was generated by plotting Log of the initial speed rate as a function of the Log of the standard quantities. The standard curve was used to qualify each assay run.

sALP or sALP-Fc concentration in U/L of PK serum samples was determined by the conversion of their respective Vmax into units. One unit is defined as the amount of sALP or sALP-Fc that hydrolyzes 1 μmol of p-nitrophenyl-phosphate to p-nitrophenol in 1 minute at 37° C. Due to the presence of endogenous forms of sALP or sALP-Fc in serum, the measured concentrations were corrected for the baseline value measured in spare animals.

Non Compartmental Pharmacokinetic Analysis

A non-compartmental analysis (NCA) was used to calculate the pharmacokinetic parameters of testing compound. All measured serum concentrations of testing compound versus time profile were processed using WinNonlin™ Enterprise Edition version 5.2.1. NCA Model 200 was selected for SC input or Model 201 for IV-Bolus input using sparse sampling analysis module for both model.

The following non-compartmental PK parameters were calculated:

area under the curve from time zero to infinity ($AUC_\infty$) calculated as $AUC_{last}+C_{last}/\lambda_z$ (where $\lambda_z$=slope of the terminal phase of the serum concentration vs time curve);

maximum observed serum concentration ($C_{max}$), time of maximum serum concentration ($T_{max}$);

the terminal elimination half-life ($T_{1/2}$, calculated as $0.693/\lambda_z$);

systemic clearance after intravenous administration (CL) and subcutaneous administration (CL_F) was calculated as Dose/$AUC_\infty$;

Absolute bioavailability (F %) between routes was calculated using the following formula:

[$AUC_\infty(sc)$/Dose($sc$)]/[$AUC_\infty(iv)$/Dose($iv$)]×100.

Nominal times were used in the calculations and times were set relative to start of dosing. Nominal doses were used for the calculation of CL and CL_F.

Results

The mean (±SD) concentration profile in serum following single dose IV and SC administration of sALP and sALP-Fc are shown in FIGS. 7(a) and 7(b), respectively. The calculated PK parameters are shown in Tables 2(a) and 2(b).

TABLE 2a

Pharmacokinetic parameters of sALP and sALP-Fc in serum (single dose IV administration).

| PK Parameters (NCA) | Units | sALP | sALP-Fc |
|---|---|---|---|
| Dose | U/kg | 10000 | 2000 |
| $C_{max}$/Dose | U/L/U/kg | 4.32 | 8.54 |
| $AUC_\infty$/Dose | U/L * hr/U/kg | 16.0 | 70.6 |
| CL | L/hr/kg | 0.0627 | 0.0142 |
| Half life | hr | 17.6 | 46.9 |

TABLE 2b

Pharmacokinetic parameters of sALP and sALP-Fc in serum (single dose SC administration).

| PK Parameters (NCA) | Units | sALP | sALP-Fc |
|---|---|---|---|
| Dose | U/kg | 10000 | 2000 |
| $C_{max}$/Dose | U/L/U/kg | 0.0514 | 0.413 |
| $AUC_\infty$/Dose | U/L * hr/U/kg | 0.483 | 26.2 |
| CL_F | L/hr/kg | 2.07 | 0.0382 |
| Half life | hr | 24.5 | 43.7 |
| Bioavailability | % | 3.02 | 37.1 |

Conclusions

From the data, it can be seen that fusion of the IgG1 Fc domain to sALP increases its SC bioavailability by a factor of more than 10 and increases its systemic exposure following SC administration by a factor of more than 50.

Example 4

Evaluation in Akp2$^{-/-}$ Mice of the Relationship Between Dose and Response after 43 Days of Bolus Subcutaneous Injections of sALP-Fc Generation of Akp2$^{-/-}$ Knockout Mice The Akp2$^{-/-}$ knockout mice, a mouse model of infantile HPP, was created by insertion of the Neo cassette into exon 6 of the mouse TNSALP gene (Akp2) via homologous recombination, functionally inactivates the Akp2 gene resulting in no detectable TNSALP mRNA or protein. They are maintained as 12.5% C57B1/6-87.5% 129J Akp2$^{-/-}$. Phenotypically, Akp2$^{-/-}$ mice closely mimic infantile HPP. Like these patients, Akp2$^{-/-}$ mice have global deficiency of TNSALP activity, extracellular accumulation of the ALP substrates PP$_i$, PLP, and phosphoethanolamine (PEA), and postnatally manifest an acquired defect in mineralization of skeletal matrix leading to radiographically and histologically obvious rickets or osteomalacia. They have stunted growth and also develop epileptic seizures and apnea, and die between postnatal days 10-12. Pyridoxine supplementation briefly suppresses their seizures and extends their lifespan, but only until postnatal days 18-22. Therefore, all animals (breeders, nursing mothers and their pups, and weanlings) in this study were given free access to modified laboratory rodent diet 5001 containing increased levels (325 ppm) of pyridoxine.

The Akp2$^{-/-}$ homozygotous mice were identified at birth (Day 0) by PCR of tissue biopsies using specific primers to exon VI of the mouse TNSALP gene: GTCCGTGGGCAT-TGTGACTACCAC (SEQ ID NO: 18) and TGCTGCTC-CACTCACGTCG (SEQ ID NO: 19).

Experimental Design

Akp2$^{-/-}$ mice were divided into 4 treatment groups:

Group 1 (Vehicle): Akp2$^{-/-}$ mice treated with vehicle SC daily (n=18);

Group 2 (Tx-1): Akp2$^{-/-}$ mice treated with sALP-Fc at 1 mg/kg SC daily (n=17);

Group 3 (Tx-3): Akp2$^{-/-}$ mice treated with sALP-Fc at 3 mg/kg SC daily (n=19);

Group 4 (Tx-6): Akp2$^{-/-}$ mice treated with sALP-Fc at 6 mg/kg SC daily (n=17);

Group 5 (WT): wild-type littermates of Akp2$^{-/-}$ mice served as reference animals and did not receive injections (n=35).

Injections were administered between 8:00 and 11:00 am, and dose volume was set at 3.3 mL/kg body weight. The actual volume given was calculated and adjusted based on the daily body weight measured prior to injection. Vehicle or sALP-Fc was injected SC into the scapular region. All treatments began on postnatal Day 1, and repeated daily for up to 43 days or until the time of necropsy.

Terminal Procedures

Necropsy was performed on Day 44, 24 hours after the final injection for those animals that completed the experimental protocol or sooner for those animals that appear terminally ill. All animals were euthanized by bilateral thoracotomy under isoflurane anesthesia. The necropsy consisted of a gross pathology check, with a piece of ear collected to reconfirm the Akp2$^{-/-}$ genotype. The bone samples were cleaned, fixed in 10% neutral buffered formalin for 3 days at 2 to 8° C., and then transferred to 70% ethanol for storage at 2 to 8° C. Femur and tibia lengths were measured using a caliper.

Radiographic Analysis

Radiographic images were obtained with a Faxitron MX-20 DC4 (Faxitron X-ray Corporation, Wheeling, Ill.), using energy of 26 kV and an exposure time of 10 seconds. Defects in bone mineralization were classified in a blinded fashion by a veterinarian radiologist. Animals were "Abnormal" if at least one bone structure (including secondary ossification centers) was absent.

Statistical Analyses

All numerical values are presented as mean values±standard deviation. Non-parametric analysis was preferred for all parameters because of the small sample sizes. The Log-Rank test was used to compare survival curves. Chi-square test was used to compare the distribution of normal and abnormal radiographs between treatments. An Anova model was used to compare the average body weights between groups at each day, and the average bone lengths at the end of the study.

Dose-Response Analysis

The following conceptual pharmacodynamic (PD) models were used to fit dose-response data as describe in Table 3.

TABLE 3

Pharmacodynamic models used to fit dose-response data

| Model | Equations |
| --- | --- |
| Linear Model | $E = E_0 + S * C$ |
| Simple $E_{max}$ Model | $E = (E_{max} * C)/(C + ED_{50})$ |
| Simple $E_{max}$ Model with $E_0$ | $E = E_0 + (E_{max} - E_0) * (C/(C + ED_{50}))$ |
| Sigmoid $E_{max}$ Model | $E = (E_{max} * C^\gamma)/(C^\gamma + ED_{50}^\gamma)$ |
| Sigmoid $E_{max}$ Model with $E_0$ | $E = E_0 + (E_{max} - E0) * (C^\gamma/(C^\gamma + ED_{50}^\gamma))$ |
| Weibull | $E = E_{max} * (1 - \exp(-(C/ED_{50})^S))$ |
| Makoid-Banakar | $E = E_{max} * (C/Cmax)^S * \exp(S * (1 - C/Cmax))$, when $C \le Cmax$, $E = E_{max}$, when $C > C_{max}$ |

$E$ = effects,
$C$ = Dose,
$S$ = Slope,
$\gamma$ = sigmoidicity factor,
$C_{max}$ = maximal dose,
$E_{max}$ = maximal effects,
$E_0$ = baseline effects at $C = 0$;
$ED_{50}$ = dose that induced 50% of $E_{max}$ Akaike Information (AIC) and Schwarz Bayesian (SBC) Criterions were used as a measure of goodness of fit to select the best model for each data set. When comparing several models for a given data set, the model associated with the smallest AIC and SBC was selected during the model discrimination process. The correlation coefficient ($r^2$) and visual assessments of fit (VAF), absolute residual distribution, coefficient of variation of PD parameters were also used for the model discrimination.

Once the appropriate model has been selected, the fit was re-run using predefined weighting schemes (1/Y, 1/Yhat, 1/Y.Y and 1/Yhat. Yhat) in WinNonlin 5.2. The same criteria as those used to select the model were again utilized for selecting the appropriate weighting scheme for each data set. The final PD parameters were generated from selected model using the best weighting scheme. Pharmacodynamic (PD) analysis was performed using WinNonlin™ Enterprise v5.2. Tables and figures were generated using Microsoft Office (Excel) 2003, and SigmaPlot v9.0.1.

All analyses were performed using full precision. Whenever possible, individual data was reported to 3 significant figures. PD parameters and their 95% confidence intervals were determined using WinNonlin 5.2.

Results

The objective of the present study was to define the dose response relationship between increasing amounts of sALP-Fc using bolus SC injections and the therapeutic response after 43 days. Endpoints were survival, body weight, bone length of the tibiae and femora, and bone mineralization defects of feet.

Figure 8:
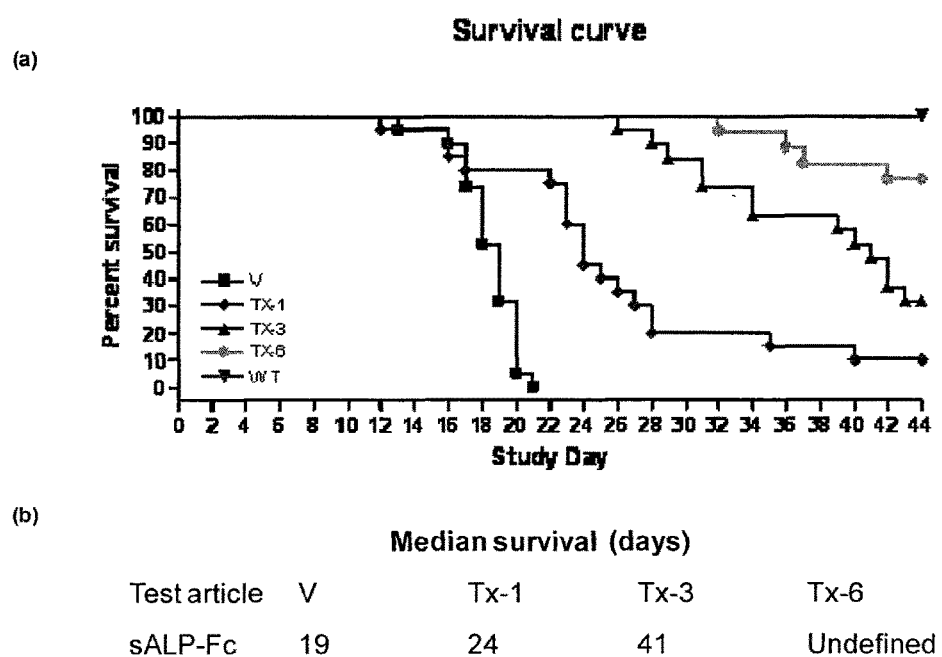
FIG. 8 shows (a) percentage survival and (b) median survival of Akp2$^{-/-}$ mice receiving either Vehicle or escalating doses of sALP-Fc, i.e., Tx-1, Tx-3, and Tx-6.

Survival of mice representing each treatment group was significantly improved when compared to Vehicle (p<0.0001) (FIG. 8(a)). Differences were also statistically significant when the survival curves of the treated groups were compared (p<0.0001). Median survival was 19, 25, and 41 days in the Vehicle, Tx-1, and Tx-3 groups, respectively (FIG. 8(b)). Only four of 17 mice in Tx-6 died before the completion of the study; thus, median survival could not be calculated for this group. However, there was a clear relationship between the sALP-Fc daily dose and the survival of Akp2$^{-/-}$ mice.

Figure 9:
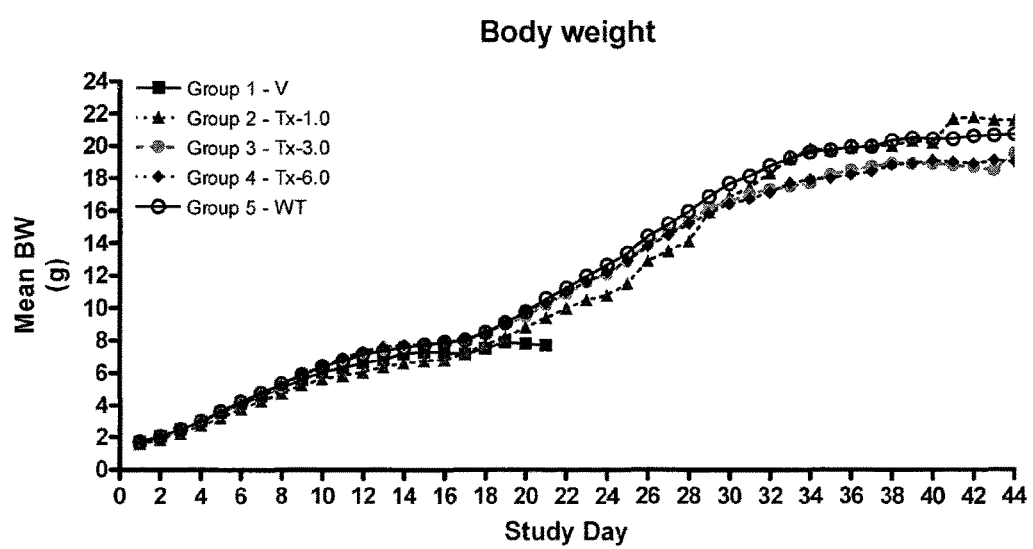
FIG. 9 shows changes in body weight with age as a function of treatment dose. Average daily body weights from Day 1 to the end of the study of Akp2$^{-/-}$ mice treated with Vehicle, Tx-1, Tx-3, Tx-6 or untreated WT mice.

Changes in body weight are depicted in FIG. 9. At the beginning of treatment, average daily body weights (BWs) showed no statistical difference between the newborn Akp2$^{-/-}$ mice of each treatment group and newborn WT mice. At the end of the study, average daily BWs remained similar between the treated Akp2$^{-/-}$ mice and the WT mice.

Figure 10:
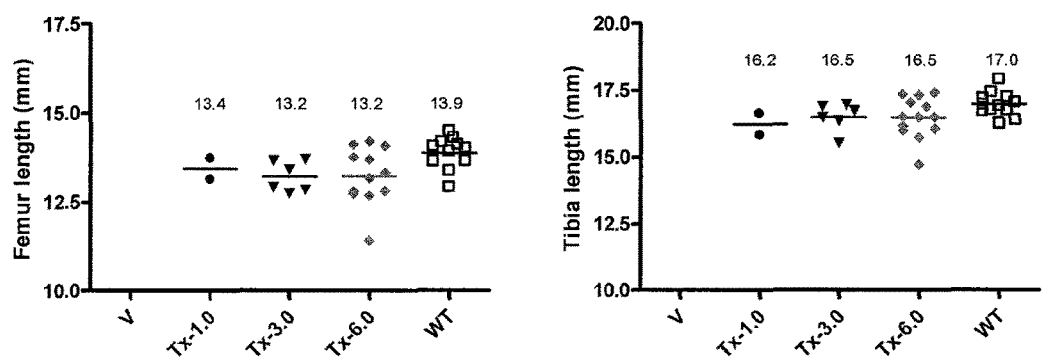
FIG. 10 shows tibiae/femora lengths as a function of treatment dose. Individual lengths of the left tibia and femora at the end of the study for two treatment doses compared to WT.

Changes in femur/tibial lengths of the mice are depicted in FIG. 10. These data show that, at the end of the study, there was no statistically significant difference between Akp2$^{-/-}$ mice of each treatment group and WT mice in the average lengths of the tibiae and femora. Deaths of the vehicle mice precluded age-matched bone length analysis.

Figure 11:
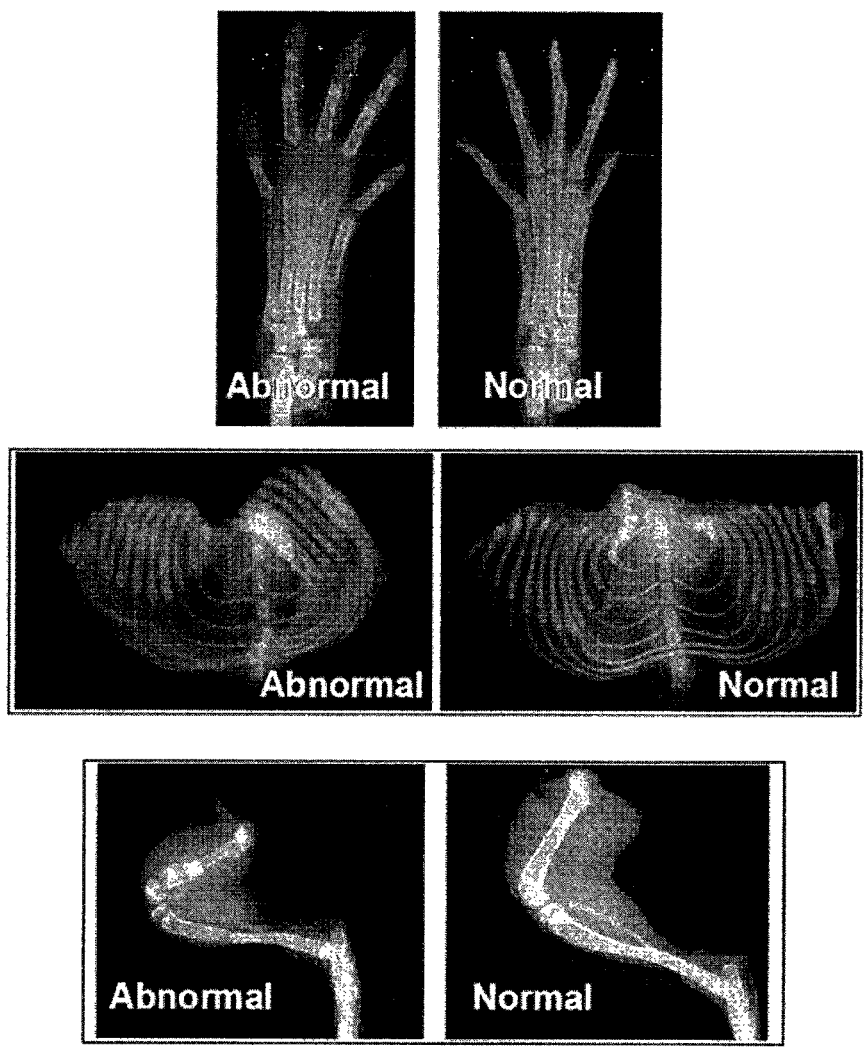
FIG. 11 shows radiographs of representative left foot (radiographic magnification 3×), rib cage (radiographic magnification (2×), and right lower limb specimens (radiographic magnification 2×) in Akp2$^{-/-}$ and normal mice.

Representative radiographs of "normal" and "abnormal" feet, rib cage, and lower limb specimens are depicted in FIG. 11. The radiographic results for each treatment group, i.e., Akp2$^{-/-}$ receiving vehicle alone versus 1, 3, or 6 mg/kg/day sALP-Fc, are summarized in Table 4. Here, the distributions of normal and abnormal radiographic images are presented with the percentages given in parentheses. Individual radiographic image distribution values of every treatment group were corrected for the baseline number of animals with normal mineralization found in the vehicle group. The number of animals in the vehicle group having normal mineralization was considered as the baseline values. The baseline value was subtracted from the corresponding number of normal and abnormal animals found in dosing groups.

TABLE 4

Distribution between normal and abnormal radiographic images of the feet of Akp2$^{-/-}$ mice receiving vehicle or 1, 3, or 6 mg/kg/day sALP-Fc.

| Uncorrected for baseline value | | Corrected for baseline value | |
| --- | --- | --- | --- |
| Group | % Normal | Group | % Normal |
| Vehicle (N = 17) | 8 (47) | Vehicle (N = 9) | 0 (0) |
| Tx-1 (N = 17) | 12 (70) | Tx-1 (N = 9) | 4 (44) |
| Tx-3 (N = 19) | 17 (89) | Tx-3 (N = 11) | 9 (82) |
| Tx-6 (N = 17) | 16 (94) | Tx-6 (N = 9) | 8 (89) |

The dose response to sALP-Fc treatment was examined by evaluating the effect of various doses on the radiographic image distribution (RID) pharmacodynamic endpoint. With the use of mathematical and graphical criteria, a sigmoid $E_{max}$ model was determined to be the best model for fitting the corrected RID feet dataset. A uniform error model was used throughout the model fit procedure.

Figure 12:
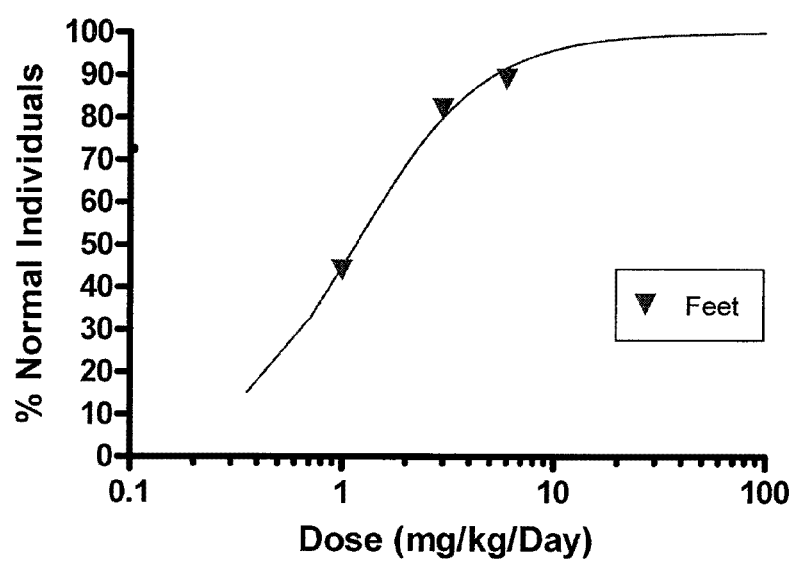
FIG. 12 shows the percentage of normal individuals as a function of sALP-Fc dose in relation to mineralization improvement in feet.

There was a clear relationship between daily dose of sALP-Fc and percent of mice with normal bone of the foot. The 80% effective dose was estimated to be 3.0 mg/kg/day for feet (FIG. 12).

These examples demonstrate that HPP mice treated with sALP-Fc experience therapeutic benefits that are significantly greater than those of sALP.

REFERENCES

The following documents are hereby incorporated by reference:
1. Ali et al., "Isolation and characterization of calcifying matrix vesicles from epiphyseal cartilage," Proc. Natl. Acad. Sci. USA 67:1513-20, 1970.
2. Anderson et al., "Matrix vesicles in osteomalacic hypophosphatasia bone contain apatite-like mineral crystals," Am. J. Pathol. 151:1555-61, 1997.

3. Anderson et al., "The role of matrix vesicles in growth plate development and biomineralization," *Frontiers in Bioscience* 10:822-837, 2005.
4. Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," *Am. J. Pathol.* 166:1711-1720, 2005.
5. Anderson et al., "Pyrophosphate stimulation of calcium uptake into cultured embryonic bones. Fine structure of matrix vesicles and their role in calcification," *Dev. Biol.* 34:211-227, 1973.
6. Anderson et al., "Impaired. Calcification Around Matrix Vesicles of Growth Plate and Bone in Alkaline Phosphatase-Deficient Mice," *Am. J. Pathol.* 164:841-847, 2004.
7. Bernard, "Ultrastructural localization of alkaline phosphatase in initial intramembranous osteogenesis," *Clin. Orthop.* 218-25, 1978.
8. DiMaura et al., "Kinetic characterization of hypophosphatasia mutations with physiological substrates," *J. Bone Miner. Res.* 17:1383-1391, 2002.
9. Farley et al., "Effects of Tunicamycin, Mannosamine, and Other Inhibitors of Glycoprotein Processing on Skeletal Alkaline Phosphatase in Human Osteoblast-Like Cells," *Calcified Tissue International* 76:63-74, 2005.
10. Fedde et al., "Alkaline phosphatase knock-out mice recapitulate the metabolic and skeletal defects of infantile hypophosphatasia,"*J. Bone Miner. Res.* 14:2015-2026, 1999.
11. Greenberg et al. "A homoallelic Gly317->Asp mutation in ALPL causes the perinatal (lethal) form of hypophosphatasia in Canadian mennonites," *Genomics* 17:215-217, 1993.
12. Harmey et al., "Elevated skeletal osteopontin levels contribute to the hypophosphatasia phenotype in Akp2 (−/−) mice," *J. Bone Miner. Res.* 21:1377-1386, 2006.
13. Harmey et al., "Concerted Regulation of Inorganic Pyrophosphate and Osteopontin by Akp2, Enppi, and Ank: An integrated Model of the Pathogenesis of Mineralization Disorders,"*Am. J. Pathol.* 164:1199-1209, 2004.
14. Hawrylak et al., "The solubilization of tetrameric alkaline phosphatase from human liver and its conversion into various forms by phosphatidylinositol phospholipase C or proteolysis," *J. Biol. Chem.* 263:14368-14373, 1988.
15. Henthorn et al., "Different missense mutations at the tissue-nonspecific alkaline phosphatase gene locus in autosomal recessively inherited forms of mild and severe hypophosphatasia," *Proc. Natl. Acad. Sci. USA* 89:9924-9928, 1992.
16. Henthorn et al., "Missense mutations of the tissue-nonspecific alkaline phosphatase gene in hypophosphatasia," *Clin. Chem.* 38:2501-2505, 1992.
17. Hessle et al., "Tissue-nonspecific alkaline phosphatase and plasma cell membrane glycoprotein-1 are central antagonistic regulators of bone mineralization," *Proc. Natl. Acad. Sci. USA* 99:9445-9449, 2002.
18. Ikezawa, "Glycosylphosphatidylinositol (GPI)-Anchored Proteins,"*Biol. Pharm. Bull.* 25:409-417, 2002.
19. Jansonius et al., "Structure, evolution and action of vitamin B6-dependent enzymes," *Curr. Opin. Struct. Biol.* 8:759-769, 1998.
20. Johnson et al., "Matrix vesicle plasma cell membrane glycoprotein-1 regulates mineralization by murine osteoblastic MC3T3 cells," *J. Bone Miner. Res.* 14:883-892, 1999.
21. Mahmood et al., "Selection of the First-Time Dose in Humans: Comparison of Different Approaches Based on Interspecies Scaling of Clearance," *J. Chn. Pharmacol.* 43:692-697, 2003.
22. Meyer, "Can biological calcification occur in the presence of pyrophosphate?" *Arch. Biochem. Biophys.* 231:1-8, 1984.
23. Millan, "Mammalian Alkaline Phosphatases. From Biology to Applications in Medicine and Biotechnology," Wiley-VCH Verlag GmbH & Co., Weinheim, Germany 1-322, 2006.
24. Morris et al., "Immunolocalization of alkaline phosphatase in osteoblasts and matrix vesicles of human fetal bone," *Bone Miner.* 19:287-98, 1992.
25. Murshed et al., "Unique coexpression in osteoblasts of broadly expressed genes accounts for the spatial restriction of ECM mineralization to bone. *Genes Dev.* 19:1093-1104, 2005.
26. Nasu et al., "Aberrant interchain disulfide bridge of tissue-nonspecific alkalinephosphatase with an Arg433Cys substitution associated with severe hypophosphatasia," *FEBS Journal* 273:5612-5624, 2006.
27. Narisawa et al., "Inactivation of two mouse alkaline phosphatase genes and establishment of a model of infantile hypophosphatasia," *Developmental Dynamics* 208:432-446, 1997.
28. Narisawa et al., "Abnormal vitamin B6 metabolism in alkaline phosphatase knock-out mice causes multiple abnormalities, but not the impaired bone mineralization, "*J. Pathol.* 193:125-133, 2001.
29. Nishioka et al., "Enhancement of drug delivery to bone: Characterization of human tissue-non specific alkaline phosphatase tagged with an acidic oligopeptide," *Mol. Genet. Metab.* 88:244-255, 2006.
30. Nosjean et al., "Human tissue non-specific alkaline phosphatases: Sugar-moiety-induced enzymic and antigenic modulations and genetic aspects," *Biochem. J.* 321:297-303, 1997.
31. Oda et al. "A General Method for Rapid Purification of Soluble Versions of Glycosyhphatidylinositol-Anchored Proteins Expressed in Insect Cells: An Application for Human Tissue-Nonspecific Alkaline Phosphatase," *J. Biochem.* 126:694-699, 1999.
32. Rezende et al., "Inorganic pyrophosphate-phosphohydrolytic activity associated with rat osseous plate alkaline phosphatase," *Cell. Mol. Biol.* 44:293-302, 1998.
33. Urlaub et al., "Deletion of the Diploid Dihydrofolate-Reductase Locus from Cultured Mammalian-Cells," *Cell* 33:405-412, 1983.
34. Waymire et al., "Mice Lacking Tissue Nonspecific Alkaline-Phosphatase Die from Seizures Due to Defective Metabolism of Vitamin-B-6," *Nature Genet.* 11:45-51, 1995.
35. Weiss et al. "A missense mutation in the human liver/bone/kidney alkaline phosphatase gene causing a lethal form of hypophosphatasia," *Proc. Natl. Acad. Sci. USA* 85:7666-9, 1988.
36. Weninger et al., "Biochemical and Morphological Effects of Human Hepatic Alkaline-Phosphatase in A Neonate with Hypophosphatasia," *Acta. Paediatrica Scandinavica* 154-160, 1989.
37. Whyte, "Hypophosphatasia and the Role of Alkaline-Phosphatase in Skeletal Mineralization," *Endocrine Reviews* 15:439-461, 1994.
38. Whyte, "Alkaline Phosphatase: Placental and Tissue-nonspecific Isoenzymes hydrolyze Phosphoethanolamine, Inorganic Pyrophosphate, and Pyridoxal 5'-phosphate," *J. Clin. Invest.* 95:1440-1445, 1995.
39. Whyte, "Hypophosphatasia," In The Metabolic and Molecular Bases of Disease, edn 8th, pp 5313-5329. Eds C L Scriver, A L Beaudet, WS Sly, D ValIe & B Vogelstein. New York: McGraw-Hill Book Company, 2001.
40. Whyte, "Hypophosphatasia. Nature's window on alkaline phosphatase function in man," In Principle of Bone Biology, edn Second, pp 1229-1248. Eds J P Bilezikian, L G Raisz & G A Rodan. London: Academic Press. 2002.
41. Whyte et al., "Marrow cell transplantation for infantile hypophosphatasia," *J. Bone Miner. Res.* 18:624-636, 2003.
42. Whyte et al., "Markedly Increased Circulating Pyridoxal-5'-Phosphate Levels in Hypophosphatasia-Alkaline-Phosphatase Acts in Vitamin-B6 Metabolism," *J. Clin. Invest.* 76:752-756, 1985.
43. Whyte et al., "Enzyme replacement therapy for infantile hypophosphatasia attempted by intravenous infusions of alkaline phosphatase-rich Paget plasma: results in three additional patients," *J. Pediatr.* 105:926-933, 1984.
44. Whyte et al., "Infantile hypophosphatasia: enzyme replacement therapy by intravenous infusion of alkaline phosphatase-rich plasma from patients with Paget bone disease," *J. Pediatr.* 101:379-386, 1982.
45. Zurutuza et al., "Correlations of genotype and phenotype in hypophosphatasia," *Human Molecular Genetics* 8:1039-1046, 1999.
46. Beertsen et al., "Root development in mice lacking functional tissue non-specific alkaline phosphatase gene: Inhibition of acellular cementum formation," *J. Dent. Res.* 78:1221-1229, 1999.

Other Embodiments

All publications, patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A method of treating hypophosphatasia (HPP) in a subject, said method comprising administering to said subject a therapeutically effective amount of a pharmaceutical composition comprising:
   (a) a polypeptide comprising the structure Z-sALP-Y-Fc-X or the structure Z-Fc-Y-sALP-X; and
   (b) a pharmaceutically acceptable excipient,
   wherein sALP is the extracellular domain of an alkaline phosphatase comprising an amino acid sequence having at least 85% sequence identity to any one of SEQ ID NOs: 5-14; each of X and Z is absent and Y is an amino acid sequence of from one to twenty amino acids; and said polypeptide does not comprise a polyaspartic acid or polyglutamic acid region longer than three consecutive aspartic acid or glutamic acid residues.

2. The method of claim 1, wherein
   (a) said polypeptide comprises the structure Z-sALP-Y-Fc-X.

3. The method of claim 1, wherein
   (a) the amino acid sequence of said sALP comprises an amino acid sequence having
   at least 95% sequence identity to SEQ ID NO: 5.

4. The method of claim 1, wherein said Fc comprises a CH2 domain, a CH3 domain, and a hinge region.

5. The method of claim 1, wherein Y is two amino acid residues.

6. The method of claim 1, wherein the amino acid sequence of said polypeptide comprises an amino acid sequence having
   (a) at least 85% sequence identity to SEQ ID NO: 4,
   (b) at least 95% sequence identity to SEQ ID NO: 4, or
   (c) at least 99% sequence identity to SEQ ID NO: 4.

7. The method of claim 6, wherein the amino acid sequence of said polypeptide comprises the sequence of SEQ ID NO: 4.

8. The method of claim 1, wherein
   (a) said polypeptide is pegylated,
   (b) said polypeptide is glycosylated,
   (c) said pharmaceutical composition comprises a dimer of said polypeptide,
   (d) said pharmaceutically acceptable excipient comprises saline, or
   (e) said pharmaceutical composition is lyophilized.

9. The method of claim 1, wherein said pharmaceutical composition is administered subcutaneously, intravenously, orally, nasally, intramuscularly, sublingually, intrathecally, or intradermally.

10. The method of claim 1, wherein said HPP is infantile HPP, childhood HPP, perinatal HPP, adult HPP, or odonto-hypophosphatasia.

11. The method of claim 1, wherein said pharmaceutical composition is administered in an amount that is therapeutically effective to treat a hypophosphatasia (HPP) phenotype selected from the group consisting of HPP-related seizure, premature loss of deciduous teeth, incomplete bone mineralization, elevated blood and/or urine levels of inorganic pyrophosphate ($PP_i$), elevated blood and/or urine levels of phosphoethanolamine (PEA), elevated blood and/or urine levels of pyridoxal 5'-phosphate (PLP), inadequate weight gain, rickets, bone pain, calcium pyrophosphate dihydrate crystal deposition, aplasia, hypoplasia, and dysplasia of the dental cementum.

12. The method of claim 1, wherein said subject is human.

13. The method of claim 1, wherein said polypeptide does not comprise a polyaspartic acid or polyglutamic acid region longer than two consecutive aspartic acid or glutamic acid residues.

14. The method of claim 1, wherein said Fc is a constant domain of an immunoglobulin selected from the group consisting of IgG-1, IgG-2, IgG-3, and IgG-4.

15. The method of claim 14, wherein the amino acid sequence of said Fc comprises an amino acid sequence having:
   (i) at least 85% sequence identity to SEQ ID NO: 3,
   (ii) at least 95% sequence identity to SEQ ID NO: 3, or
   (iii) at least 99% sequence identity to SEQ ID NO: 3.

16. The method of claim 14, wherein the amino acid sequence of said Fc comprises the sequence of SEQ ID NO: 3.

17. The method of claim 5, wherein Y is leucine-lysine.

18. The method of claim 9, wherein said pharmaceutical composition is administered subcutaneously to said subject in a dosage of about 0.5 mg/kg/day to about 10 mg/kg/day.

19. The method of claim 18, wherein said pharmaceutical composition is administered subcutaneously to said subject in a dosage of about 2 mg/kg/day to about 3 mg/kg/day.

20. The method of claim 9, wherein said pharmaceutical composition is administered subcutaneously to said subject between one and seven times a week.

21. The method of claim 20, wherein said pharmaceutical composition is administered subcutaneously to said subject three times a week.

22. The method of claim 11, wherein said incomplete bone mineralization is incomplete femoral bone mineralization, incomplete tibial bone mineralization, incomplete metatarsal bone mineralization, or incomplete rib bone mineralization.

23. The method of claim 7, wherein the amino acid sequence of said polypeptide consists of the sequence of SEQ ID NO: 4.

24. The method of claim 10, wherein said HPP is infantile HPP.

25. The method of claim 10, wherein said HPP is perinatal HPP.

26. The method of claim 10, wherein said HPP is childhood HPP.

27. The method of claim 10, wherein said HPP is adult HPP.

28. The method of claim 16, wherein the amino acid sequence of said Fc consists of the sequence of SEQ ID NO: 3.

29. The method of claim 3, wherein the amino acid sequence of said sALP comprises an amino acid sequence having at least 99% sequence identity to SEQ ID NO: 5.

30. The method of claim 29, wherein the amino acid sequence of said sALP comprises the sequence of SEQ ID NO: 5.

31. The method of claim 30, wherein the amino acid sequence of said sALP consists of the sequence of SEQ ID NO: 5.

* * * * *

SEQUENCE LISTING

```
<160> NUMBER OF SEQ ID NOS: 19

<210> SEQ ID NO 1
<211> LENGTH: 731
<212> TYPE: PRT
<213> ORGANISM: Artificial Sequence
<220> FEATURE:
<223> OTHER INFORMATION: hsTNALP-Fc with N-terminal signal sequence

<400> SEQUENCE: 1

Met Val Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205
```

-continued

Met His Asn Ile Arg Asp Ile Asp Val Ile Met Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Leu Lys Asp Lys Thr His Thr Cys Pro Pro
                500                 505                 510

Cys Pro Ala Pro Glu Leu Leu Gly Gly Pro Ser Val Phe Leu Phe Pro
            515                 520                 525

Pro Lys Pro Lys Asp Thr Leu Met Ile Ser Arg Thr Pro Glu Val Thr
        530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
                580                 585                 590

Leu His Gln Asp Trp Leu Asn Gly Lys Glu Tyr Lys Cys Lys Val Ser
        595                 600                 605

Asn Lys Ala Leu Pro Ala Pro Ile Glu Lys Thr Ile Ser Lys Ala Lys
    610                 615                 620

```
Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
            645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
            675                 680                 685

Phe Leu Tyr Ser Lys Leu Thr Val Asp Lys Ser Arg Trp Gln Gln Gly
        690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys
            725                 730

<210> SEQ ID NO 2
<211> LENGTH: 502
<212> TYPE: PRT
<213> ORGANISM: Artificial Sequence
<220> FEATURE:
<223> OTHER INFORMATION: hsTNALP 1-502

<400> SEQUENCE: 2

Met Val Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
        100                 105                 110

Thr Ala Thr Ala Tyr Leu Cys Gly Val Lys Ala Asn Glu Gly Thr Val
    115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
        180                 185                 190

Pro Pro Glu Ala Leu Ser Gln Gly Cys Lys Asp Ile Ala Tyr Gln Leu
    195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
            245                 250                 255
```

```
Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser
            500

<210> SEQ ID NO 3
<211> LENGTH: 227
<212> TYPE: PRT
<213> ORGANISM: Artificial Sequence
<220> FEATURE:
<223> OTHER INFORMATION: IgG-1 Fc fragment

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 714
<212> TYPE: PRT
<213> ORGANISM: Artificial Sequence
<220> FEATURE:
<223> OTHER INFORMATION: hsTNALP-Fc without N-terminal signal sequence

<400> SEQUENCE: 4

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240
```

```
Ser Phe Lys Pro Arg Tyr Lys His Ser His Phe Ile Trp Asn Arg Thr
            245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
            275                 280                 285

Asp Pro Ser Leu Ser Glu Met Val Val Ala Ile Gln Ile Leu Arg
            290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
            355                 360                 365

Gly Gly Tyr Thr Pro Arg Gly Asn Ser Ile Phe Gly Leu Ala Pro Met
370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
            435                 440                 445

Pro Met Ala His Leu Leu His Gly Val His Glu Gln Asn Tyr Val Pro
450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
            530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Glu Glu
            610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
```

-continued

```
                 660                 665                 670
Leu Tyr Ser Lys Leu Thr Val Asp Lys Ser Arg Trp Gln Gln Gly Asn
             675                 680                 685

Val Phe Ser Cys Ser Val Met His Glu Ala Leu His Asn His Tyr Thr
         690                 695                 700

Gln Lys Ser Leu Ser Leu Ser Pro Gly Lys
705                 710

<210> SEQ ID NO 5
<211> LENGTH: 485
<212> TYPE: PRT
<213> ORGANISM: Homo sapiens
<220> FEATURE:
<221> NAME/KEY: MISC_FEATURE
<223> OTHER INFORMATION: hsTNALP without N-terminal signal sequence

<400> SEQUENCE: 5

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Val Ala Ile Gln Ile Leu Arg
    290                 295                 300
```

```
Lys Asn Pro Lys Gly Phe Leu Leu Val Glu Gly Gly Arg Ile Asp
305                 310                 315                 320

His Gly His His Glu Gly Lys Ala Lys Gln Ala Leu His Glu Ala Val
            325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
            355                 360                 365

Gly Gly Tyr Thr Pro Arg Gly Asn Ser Ile Phe Gly Leu Ala Pro Met
            370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
            405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
            435                 440                 445

Pro Met Ala His Leu Leu His Gly Val His Glu Gln Asn Tyr Val Pro
450                 455                 460

His Val Met Ala Tyr Ala Ala Cys Ile Gly Ala Asn Leu Gly His Cys
465                 470                 475                 480

Ala Pro Ala Ser Ser
            485

<210> SEQ ID NO 6
<211> LENGTH: 524
<212> TYPE: PRT
<213> ORGANISM: Homo sapiens
<220> FEATURE:
<221> NAME/KEY: MISC_FEATURE
<223> OTHER INFORMATION: TNALP

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
            165                 170                 175
```

```
Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
        515                 520

<210> SEQ ID NO 7
<211> LENGTH: 524
<212> TYPE: PRT
<213> ORGANISM: Bos taurus
<220> FEATURE:
<221> NAME/KEY: MISC_FEATURE
<223> OTHER INFORMATION: TNALP

<400> SEQUENCE: 7

Met Ile Ser Pro Phe Leu Leu Leu Ala Ile Gly Thr Cys Phe Ala Ser
```

```
1               5                   10                  15
Ser Leu Val Pro Glu Lys Glu Lys Asp Pro Lys Tyr Trp Arg Asp Gln
                20                  25                  30

Ala Gln Gln Thr Leu Lys Asn Ala Leu Arg Leu Gln Thr Leu Asn Thr
                35                  40                  45

Asn Val Ala Lys Asn Val Ile Met Phe Leu Gly Asp Gly Met Gly Val
                50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
                115                 120                 125

Gly Val Ser Ala Ala Thr Gln Arg Ser Gln Cys Asn Thr Thr Gln Gly
                130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Lys Asp Ile Glu Val Ile Met Gly Gly Gly Arg Lys
                210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
                260                 265                 270

Thr Asp Leu Leu Ala Leu Asp Pro His Ser Val Asp Tyr Leu Leu Gly
                275                 280                 285

Leu Phe Glu Pro Gly Asp Met Gln Tyr Glu Leu Asn Arg Asn Asn Ala
                290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Gln Ala Ile Gly Gln Ala Gly Ala Met Thr Ser Val
                355                 360                 365

Glu Asp Thr Leu Thr Val Val Thr Ala Asp His Ser His Val Phe Thr
                370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430
```

-continued

Met Val Asp Tyr Ala His Asn Tyr Gln Ala Gln Ser Ala Val Pro
            435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
                500                 505                 510

Leu Leu Leu Ala Leu Leu Pro Leu Gly Ser Leu Phe
    515                 520

<210> SEQ ID NO 8
<211> LENGTH: 524
<212> TYPE: PRT
<213> ORGANISM: Felis catus
<220> FEATURE:
<221> NAME/KEY: MISC_FEATURE
<223> OTHER INFORMATION: TNALP

<400> SEQUENCE: 8

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Gln Thr Leu Lys Asn Ala Leu Arg Leu Gln Lys Leu Asn Thr
            35                  40                  45

Asn Val Val Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Thr Gln Cys Asn Thr Thr Gln Gly
130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Val Arg Asp Ile Glu Val Ile Met Gly Gly Gly Arg Lys
    210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg

```
            260                 265                 270
Thr Glu Leu Leu Thr Leu Asp Pro Tyr Gly Val Asp Tyr Leu Leu Gly
        275                 280                 285

Leu Phe Glu Pro Gly Asp Met Gln Tyr Glu Leu Asn Arg Asn Ser Thr
        290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Gln Ala Ile Gly Arg Ala Gly Ala Met Thr Ser Val
                355                 360                 365

Glu Asp Thr Leu Thr Ile Val Thr Ala Asp His Ser His Val Phe Thr
                370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ala Lys
                450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
                500                 505                 510

Leu Leu Leu Ala Leu Pro Ser Leu Gly Ile Leu Phe
            515                 520

<210> SEQ ID NO 9
<211> LENGTH: 524
<212> TYPE: PRT
<213> ORGANISM: Mus musculus
<220> FEATURE:
<221> NAME/KEY: MISC_FEATURE
<223> OTHER INFORMATION: TNALP

<400> SEQUENCE: 9

Met Ile Ser Pro Phe Leu Val Leu Ala Ile Gly Thr Cys Leu Thr Asn
1               5                   10                  15

Ser Phe Val Pro Glu Lys Glu Arg Asp Pro Ser Tyr Trp Arg Gln Gln
                20                  25                  30

Ala Gln Glu Thr Leu Lys Asn Ala Leu Lys Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65              70                  75                  80

Thr Gly Glu Glu Thr Arg Leu Glu Met Asp Lys Phe Pro Phe Val Ala
                85                  90                  95
```

```
Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Lys Ala Gly Ala Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Gly Ser Gly Ser Ala Pro Ser Pro Gly Ala Leu Leu
            500                 505                 510

Leu Pro Leu Ala Val Leu Ser Leu Pro Thr Leu Phe
```

```
<210> SEQ ID NO 10
<211> LENGTH: 524
<212> TYPE: PRT
<213> ORGANISM: Rattus norvegicus
<220> FEATURE:
<221> NAME/KEY: MISC_FEATURE
<223> OTHER INFORMATION: TNALP

<400> SEQUENCE: 10

Met Ile Leu Pro Phe Leu Val Leu Ala Ile Gly Thr Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Ile Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350
```

```
Val Glu Met Asp Glu Ala Ile Gly Lys Ala Gly Thr Met Thr Ser Gln
            355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Ser Ser Ala Ser Ser Pro Ser Pro Gly Ala Leu Leu
            500                 505                 510

Leu Pro Leu Ala Leu Phe Pro Leu Arg Thr Leu Phe
        515                 520

<210> SEQ ID NO 11
<211> LENGTH: 502
<212> TYPE: PRT
<213> ORGANISM: Canis familiaris
<220> FEATURE:
<221> NAME/KEY: MISC_FEATURE
<223> OTHER INFORMATION: TNALP

<400> SEQUENCE: 11

Glu Lys Asp Pro Lys Tyr Trp Arg Asp Gln Ala Gln Gln Thr Leu Lys
1               5                   10                  15

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
                85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125

Leu Arg Trp Ala Lys Asp Ala Gly Lys Ser Val Gly Ile Val Thr Thr
    130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp
            180                 185                 190
```

Ile Glu Val Ile Met Gly Gly Arg Lys Tyr Met Phe Pro Lys Asn
            195                 200                 205

Arg Thr Asp Val Glu Tyr Glu Met Asp Glu Lys Ser Thr Gly Ala Arg
    210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                245                 250                 255

Asp Pro Tyr Thr Val Asp Tyr Leu Leu Gly Leu Phe Asp Pro Gly Asp
            260                 265                 270

Met Gln Tyr Glu Leu Asn Arg Asn Asn Val Thr Asp Pro Ser Leu Ser
        275                 280                 285

Glu Met Val Glu Ile Ala Ile Lys Ile Leu Ser Lys Lys Pro Arg Gly
    290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                325                 330                 335

Ile Gly Lys Ala Gly Val Met Thr Ser Leu Glu Asp Thr Leu Thr Val
            340                 345                 350

Val Thr Ala Asp His Ser His Val Phe Thr Phe Gly Gly Tyr Thr Pro
        355                 360                 365

Arg Gly Asn Ser Ile Phe Gly Leu Ala Pro Met Val Ser Asp Thr Asp
    370                 375                 380

Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                405                 410                 415

Asn Asn Tyr Gln Ala Gln Ser Ala Val Pro Leu Arg His Glu Thr His
            420                 425                 430

Gly Gly Glu Asp Val Ala Val Phe Ala Lys Gly Pro Met Ala His Leu
        435                 440                 445

Leu His Gly Val His Glu Gln Asn Tyr Ile Pro His Val Met Ala Tyr
    450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                485                 490                 495

Pro Val Gly Ile Leu Phe
            500

<210> SEQ ID NO 12
<211> LENGTH: 528
<212> TYPE: PRT
<213> ORGANISM: Homo sapiens
<220> FEATURE:
<221> NAME/KEY: MISC_FEATURE
<223> OTHER INFORMATION: IALP

<400> SEQUENCE: 12

Met Gln Gly Pro Trp Val Leu Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile

```
            35                  40                  45
Gln Lys Val Ala Lys Asn Leu Ile Leu Phe Leu Gly Asp Gly Leu Gly
 50                  55                  60

Val Pro Thr Val Thr Ala Thr Arg Ile Leu Lys Gly Gln Lys Asn Gly
 65                  70                  75                  80

Lys Leu Gly Pro Glu Thr Pro Leu Ala Met Asp Arg Phe Pro Tyr Leu
                 85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
                115                 120                 125

Ile Gly Leu Ser Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
                195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
                260                 265                 270

Met Gln Ala Ser Leu Asp Gln Ser Val Thr His Leu Met Gly Leu Phe
                275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
                340                 345                 350

Phe Asp Asp Ala Ile Glu Arg Ala Gly Gln Leu Thr Ser Glu Glu Asp
                355                 360                 365

Thr Leu Thr Leu Val Thr Ala Asp His Ser His Val Phe Ser Phe Gly
370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
                420                 425                 430

Ser Gly Ser Pro Asp Tyr Gln Gln Gln Ala Ala Val Pro Leu Ser Ser
                435                 440                 445

Glu Thr His Gly Gly Glu Asp Val Ala Val Phe Ala Arg Gly Pro Gln
450                 455                 460
```

-continued

```
Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525

<210> SEQ ID NO 13
<211> LENGTH: 532
<212> TYPE: PRT
<213> ORGANISM: Homo sapiens
<220> FEATURE:
<221> NAME/KEY: MISC_FEATURE
<223> OTHER INFORMATION: GCALP

<400> SEQUENCE: 13

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
```

```
            290                 295                 300
Pro Ser Leu Met Glu Met Thr Glu Ala Ala Leu Leu Leu Ser Arg
305                 310                 315                 320

Asn Pro Arg Gly Phe Phe Leu Phe Val Glu Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
530

<210> SEQ ID NO 14
<211> LENGTH: 535
<212> TYPE: PRT
<213> ORGANISM: Homo sapiens
<220> FEATURE:
<221> NAME/KEY: MISC_FEATURE
<223> OTHER INFORMATION: PLALP

<400> SEQUENCE: 14

Met Leu Gly Pro Cys Met Leu Leu Leu Leu Leu Leu Leu Gly Leu Arg
1               5                   10                  15

Leu Gln Leu Ser Leu Gly Ile Ile Pro Val Glu Glu Glu Asn Pro Asp
            20                  25                  30

Phe Trp Asn Arg Glu Ala Ala Glu Ala Leu Gly Ala Ala Lys Lys Leu
        35                  40                  45

Gln Pro Ala Gln Thr Ala Ala Lys Asn Leu Ile Ile Phe Leu Gly Asp
    50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
            100                 105                 110
```

```
Asp Ser Gly Ala Thr Ala Thr Ala Tyr Leu Cys Gly Val Lys Gly Asn
            115                 120                 125
Phe Gln Thr Ile Gly Leu Ser Ala Ala Arg Phe Asn Gln Cys Asn
        130                 135                 140
Thr Thr Arg Gly Asn Glu Val Ile Ser Val Met Asn Arg Ala Lys Lys
145                 150                 155                 160
Ala Gly Lys Ser Val Gly Val Thr Thr Thr Arg Val Gln His Ala
                165                 170                 175
Ser Pro Ala Gly Thr Tyr Ala His Thr Val Asn Arg Asn Trp Tyr Ser
                180                 185                 190
Asp Ala Asp Val Pro Ala Ser Ala Arg Gln Glu Gly Cys Gln Asp Ile
                195                 200                 205
Ala Thr Gln Leu Ile Ser Asn Met Asp Ile Asp Val Ile Leu Gly Gly
        210                 215                 220
Gly Arg Lys Tyr Met Phe Arg Met Gly Thr Pro Asp Pro Glu Tyr Pro
225                 230                 235                 240
Asp Asp Tyr Ser Gln Gly Gly Thr Arg Leu Asp Gly Lys Asn Leu Val
                245                 250                 255
Gln Glu Trp Leu Ala Lys Arg Gln Gly Ala Arg Tyr Val Trp Asn Arg
        260                 265                 270
Thr Glu Leu Met Gln Ala Ser Leu Asp Pro Ser Val Thr His Leu Met
        275                 280                 285
Gly Leu Phe Glu Pro Gly Asp Met Lys Tyr Glu Ile His Arg Asp Ser
        290                 295                 300
Thr Leu Asp Pro Ser Leu Met Glu Met Thr Glu Ala Ala Leu Arg Leu
305                 310                 315                 320
Leu Ser Arg Asn Pro Arg Gly Phe Phe Leu Phe Val Glu Gly Gly Arg
                325                 330                 335
Ile Asp His Gly His His Glu Ser Arg Ala Tyr Arg Ala Leu Thr Glu
                340                 345                 350
Thr Ile Met Phe Asp Asp Ala Ile Glu Arg Ala Gly Gln Leu Thr Ser
        355                 360                 365
Glu Glu Asp Thr Leu Ser Leu Val Thr Ala Asp His Ser His Val Phe
370                 375                 380
Ser Phe Gly Gly Tyr Pro Leu Arg Gly Ser Ser Ile Phe Gly Leu Ala
385                 390                 395                 400
Pro Gly Lys Ala Arg Asp Arg Lys Ala Tyr Thr Val Leu Leu Tyr Gly
                405                 410                 415
Asn Gly Pro Gly Tyr Val Leu Lys Asp Gly Ala Arg Pro Asp Val Thr
                420                 425                 430
Glu Ser Glu Ser Gly Ser Pro Glu Tyr Arg Gln Gln Ser Ala Val Pro
            435                 440                 445
Leu Asp Glu Glu Thr His Ala Gly Glu Asp Val Ala Val Phe Ala Arg
        450                 455                 460
Gly Pro Gln Ala His Leu Val His Gly Val Gln Glu Gln Thr Phe Ile
465                 470                 475                 480
Ala His Val Met Ala Phe Ala Ala Cys Leu Glu Pro Tyr Thr Ala Cys
                485                 490                 495
Asp Leu Ala Pro Pro Ala Gly Thr Thr Asp Ala Ala His Pro Gly Arg
                500                 505                 510
Ser Val Val Pro Ala Leu Leu Pro Leu Leu Ala Gly Thr Leu Leu Leu
                515                 520                 525
Leu Glu Thr Ala Thr Ala Pro
```

<210> SEQ ID NO 15
<211> LENGTH: 541
<212> TYPE: PRT
<213> ORGANISM: Artificial Sequence
<220> FEATURE:
<223> OTHER INFORMATION: Consensus ALP
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: VARIANT
<222> LOCATION: (5)..(9)
<223> OTHER INFORMATION: Xaa can be any naturally occurring amino acid
      or absent
<220> FEATURE:
<221> NAME/KEY: MISC_FEATURE
<222> LOCATION: (10)..(21)
<223> OTHER INFORMATION: Xaa can be any naturally occurring amino acid
<220> FEATURE:
<221> NAME/KEY: VARIANT
<222> LOCATION: (22)..(22)
<223> OTHER INFORMATION: Xaa can be any naturally occurring amino acid
      except phenylalanine
<220> FEATURE:
<221> NAME/KEY: MISC_FEATURE
<222> LOCATION: (23)..(27)
<223> OTHER INFORMATION: Xaa can be any naturally occurring amino acid
<220> FEATURE:
<221> NAME/KEY: MISC_FEATURE
<222> LOCATION: (29)..(30)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa can be any naturally occurring amino acid
<220> FEATURE:
<221> NAME/KEY: VARIANT
<222> LOCATION: (33)..(33)
<223> OTHER INFORMATION: Xaa can be any naturally occurring amino acid
      except cysteine
<220> FEATURE:
<221> NAME/KEY: MISC_FEATURE
<222> LOCATION: (35)..(37)
<223> OTHER INFORMATION: Xaa can be any naturally occurring amino acid
<220> FEATURE:
<221> NAME/KEY: MISC_FEATURE
<222> LOCATION: (39)..(41)
<223> OTHER INFORMATION: Xaa can be any naturally occurring amino acid
<220> FEATURE:
<221> NAME/KEY: MISC_FEATURE
<222> LOCATION: (43)..(44)
<223> OTHER INFORMATION: Xaa can be any naturally occurring amino acid
<220> FEATURE:
<221> NAME/KEY: MISC_FEATURE
<222> LOCATION: (46)..(47)
<223> OTHER INFORMATION: Xaa can be any naturally occurring amino acid
<220> FEATURE:
<221> NAME/KEY: MISC_FEATURE
<222> LOCATION: (50)..(53)
<223> OTHER INFORMATION: Xaa can be any naturally occurring amino acid
<220> FEATURE:
<221> NAME/KEY: VARIANT
<222> LOCATION: (54)..(54)
<223> OTHER INFORMATION: Xaa can be any naturally occurring amino acid
      or absent
<220> FEATURE:
<221> NAME/KEY: MISC_FEATURE
<222> LOCATION: (55)..(55)
<223> OTHER INFORMATION: Xaa can be any naturally occurring amino acid
<220> FEATURE:
<221> NAME/KEY: VARIANT
<222> LOCATION: (56)..(56)
<223> OTHER INFORMATION: Xaa can be any naturally occurring amino acid
      except serine or valine
<220> FEATURE:

-continued

```
<221> NAME/KEY: MISC_FEATURE
<222> LOCATION: (59)..(59)
<223> OTHER INFORMATION: Xaa can be any naturally occurring amino acid
<220> FEATURE:
<221> NAME/KEY: MISC_FEATURE
<222> LOCATION: (61)..(61)
<223> OTHER INFORMATION: Xaa can be any naturally occurring amino acid
<220> FEATURE:
<221> NAME/KEY: VARIANT
<222> LOCATION: (67)..(67)
<223> OTHER INFORMATION: Xaa can be any naturally occurring amino acid
      except leucine, isoleucine or valine
<220> FEATURE:
<221> NAME/KEY: MISC_FEATURE
<222> LOCATION: (70)..(70)
<223> OTHER INFORMATION: Xaa can be any naturally occurring amino acid
<220> FEATURE:
<221> NAME/KEY: MISC_FEATURE
<222> LOCATION: (75)..(75)
<223> OTHER INFORMATION: Xaa can be any naturally occurring amino acid
<220> FEATURE:
<221> NAME/KEY: MISC_FEATURE
<222> LOCATION: (82)..(86)
<223> OTHER INFORMATION: Xaa can be any naturally occurring amino acid
<220> FEATURE:
<221> NAME/KEY: MISC_FEATURE
<222> LOCATION: (88)..(88)
<223> OTHER INFORMATION: Xaa can be any naturally occurring amino acid
<220> FEATURE:
<221> NAME/KEY: MISC_FEATURE
<222> LOCATION: (90)..(91)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: Xaa can be any naturally occurring amino acid
<220> FEATURE:
<221> NAME/KEY: MISC_FEATURE
<222> LOCATION: (99)..(100)
<223> OTHER INFORMATION: Xaa can be any naturally occurring amino acid
<220> FEATURE:
<221> NAME/KEY: MISC_FEATURE
<222> LOCATION: (107)..(111)
<223> OTHER INFORMATION: Xaa can be any naturally occurring amino acid
<220> FEATURE:
<221> NAME/KEY: VARIANT
<222> LOCATION: (116)..(116)
<223> OTHER INFORMATION: Xaa can be any naturally occurring amino acid
      except threonine
<220> FEATURE:
<221> NAME/KEY: VARIANT
<222> LOCATION: (117)..(117)
<223> OTHER INFORMATION: Xaa can be any naturally occurring amino acid
      except serine
<220> FEATURE:
<221> NAME/KEY: VARIANT
<222> LOCATION: (128)..(128)
<223> OTHER INFORMATION: Xaa can be any naturally occurring amino acid
      except aspartate
<220> FEATURE:
<221> NAME/KEY: MISC_FEATURE
<222> LOCATION: (130)..(131)
<223> OTHER INFORMATION: Xaa can be any naturally occurring amino acid
<220> FEATURE:
<221> NAME/KEY: VARIANT
<222> LOCATION: (133)..(133)
<223> OTHER INFORMATION: Xaa can be any naturally occurring amino acid
      except methionine
<220> FEATURE:
<221> NAME/KEY: MISC_FEATURE
<222> LOCATION: (135)..(135)
<223> OTHER INFORMATION: Xaa can be any naturally occurring amino acid
<220> FEATURE:
<221> NAME/KEY: VARIANT
<222> LOCATION: (139)..(139)
```

```
<223> OTHER INFORMATION: Xaa can be any naturally occurring amino acid
      except histidine or asparagine
<220> FEATURE:
<221> NAME/KEY: MISC_FEATURE
<222> LOCATION: (140)..(140)
<223> OTHER INFORMATION: Xaa can be any naturally occurring amino acid
<220> FEATURE:
<221> NAME/KEY: VARIANT
<222> LOCATION: (141)..(141)
<223> OTHER INFORMATION: Xaa can be any naturally occurring amino acid
      except histidine
<220> FEATURE:
<221> NAME/KEY: MISC_FEATURE
<222> LOCATION: (142)..(143)
<223> OTHER INFORMATION: Xaa can be any naturally occurring amino acid
<220> FEATURE:
<221> NAME/KEY: MISC_FEATURE
<222> LOCATION: (148)..(148)
<223> OTHER INFORMATION: Xaa can be any naturally occurring amino acid
<220> FEATURE:
<221> NAME/KEY: VARIANT
<222> LOCATION: (153)..(153)
<223> OTHER INFORMATION: Xaa can be any naturally occurring amino acid
      except alanine or isoleucine
<220> FEATURE:
<221> NAME/KEY: MISC_FEATURE
<222> LOCATION: (155)..(158)
<223> OTHER INFORMATION: Xaa can be any naturally occurring amino acid
<220> FEATURE:
<221> NAME/KEY: MISC_FEATURE
<222> LOCATION: (161)..(162)
<223> OTHER INFORMATION: Xaa can be any naturally occurring amino acid
<220> FEATURE:
<221> NAME/KEY: MISC_FEATURE
<222> LOCATION: (168)..(168)
<223> OTHER INFORMATION: Xaa can be any naturally occurring amino acid
<220> FEATURE:
<221> NAME/KEY: VARIANT
<222> LOCATION: (175)..(175)
<223> OTHER INFORMATION: Xaa can be any naturally occurring amino acid
      except aspartate
<220> FEATURE:
<221> NAME/KEY: MISC_FEATURE
<222> LOCATION: (178)..(178)
<223> OTHER INFORMATION: Xaa can be any naturally occurring amino acid
<220> FEATURE:
<221> NAME/KEY: MISC_FEATURE
<222> LOCATION: (180)..(180)
<223> OTHER INFORMATION: Xaa can be any naturally occurring amino acid
<220> FEATURE:
<221> NAME/KEY: VARIANT
<222> LOCATION: (181)..(181)
<223> OTHER INFORMATION: Xaa can be any naturally occurring amino acid
      except threonine
<220> FEATURE:
<221> NAME/KEY: VARIANT
<222> LOCATION: (182)..(182)
<223> OTHER INFORMATION: Xaa can be any naturally occurring amino acid
      except threonine
<220> FEATURE:
<221> NAME/KEY: VARIANT
<222> LOCATION: (186)..(186)
<223> OTHER INFORMATION: Xaa can be any naturally occurring amino acid
      except leucine
<220> FEATURE:
<221> NAME/KEY: MISC_FEATURE
<222> LOCATION: (187)..(188)
<223> OTHER INFORMATION: Xaa can be any naturally occurring amino acid
<220> FEATURE:
<221> NAME/KEY: MISC_FEATURE
<222> LOCATION: (190)..(190)
<223> OTHER INFORMATION: Xaa can be any naturally occurring amino acid
<220> FEATURE:
<221> NAME/KEY: MISC_FEATURE
<222> LOCATION: (195)..(195)
<223> OTHER INFORMATION: Xaa can be any naturally occurring amino acid
<220> FEATURE:
<221> NAME/KEY: VARIANT
<222> LOCATION: (196)..(196)
```

```
<223> OTHER INFORMATION: Xaa can be any naturally occurring amino acid
      except lysine or glycine
<220> FEATURE:
<221> NAME/KEY: VARIANT
<222> LOCATION: (197)..(197)
<223> OTHER INFORMATION: Xaa can be any naturally occurring amino acid
      except threonine
<220> FEATURE:
<221> NAME/KEY: MISC_FEATURE
<222> LOCATION: (199)..(200)
<223> OTHER INFORMATION: Xaa can be any naturally occurring amino acid
<220> FEATURE:
<221> NAME/KEY: MISC_FEATURE
<222> LOCATION: (202)..(204)
<223> OTHER INFORMATION: Xaa can be any naturally occurring amino acid
<220> FEATURE:
<221> NAME/KEY: MISC_FEATURE
<222> LOCATION: (207)..(207)
<223> OTHER INFORMATION: Xaa can be any naturally occurring amino acid
<220> FEATURE:
<221> NAME/KEY: MISC_FEATURE
<222> LOCATION: (211)..(211)
<223> OTHER INFORMATION: Xaa can be any naturally occurring amino acid
<220> FEATURE:
<221> NAME/KEY: MISC_FEATURE
<222> LOCATION: (214)..(215)
<223> OTHER INFORMATION: Xaa can be any naturally occurring amino acid
<220> FEATURE:
<221> NAME/KEY: VARIANT
<222> LOCATION: (217)..(217)
<223> OTHER INFORMATION: Xaa can be any naturally occurring amino acid
      except phenylalanine
<220> FEATURE:
<221> NAME/KEY: VARIANT
<222> LOCATION: (218)..(218)
<223> OTHER INFORMATION: Xaa can be any naturally occurring amino acid
      or absent
<220> FEATURE:
<221> NAME/KEY: MISC_FEATURE
<222> LOCATION: (221)..(221)
<223> OTHER INFORMATION: Xaa can be any naturally occurring amino acid
<220> FEATURE:
<221> NAME/KEY: MISC_FEATURE
<222> LOCATION: (224)..(224)
<223> OTHER INFORMATION: Xaa can be any naturally occurring amino acid
<220> FEATURE:
<221> NAME/KEY: MISC_FEATURE
<222> LOCATION: (232)..(237)
<223> OTHER INFORMATION: Xaa can be any naturally occurring amino acid
<220> FEATURE:
<221> NAME/KEY: MISC_FEATURE
<222> LOCATION: (239)..(239)
<223> OTHER INFORMATION: Xaa can be any naturally occurring amino acid
<220> FEATURE:
<221> NAME/KEY: VARIANT
<222> LOCATION: (240)..(240)
<223> OTHER INFORMATION: Xaa can be any naturally occurring amino acid
      except glycine
<220> FEATURE:
<221> NAME/KEY: MISC_FEATURE
<222> LOCATION: (242)..(243)
<223> OTHER INFORMATION: Xaa can be any naturally occurring amino acid
<220> FEATURE:
<221> NAME/KEY: MISC_FEATURE
<222> LOCATION: (245)..(248)
<223> OTHER INFORMATION: Xaa can be any naturally occurring amino acid
<220> FEATURE:
<221> NAME/KEY: MISC_FEATURE
<222> LOCATION: (250)..(250)
<223> OTHER INFORMATION: Xaa can be any naturally occurring amino acid
<220> FEATURE:
<221> NAME/KEY: MISC_FEATURE
<222> LOCATION: (255)..(256)
<223> OTHER INFORMATION: Xaa can be any naturally occurring amino acid
<220> FEATURE:
<221> NAME/KEY: MISC_FEATURE
<222> LOCATION: (258)..(260)
<223> OTHER INFORMATION: Xaa can be any naturally occurring amino acid
<220> FEATURE:
```

```
-continued

<221> NAME/KEY: MISC_FEATURE
<222> LOCATION: (262)..(262)
<223> OTHER INFORMATION: Xaa can be any naturally occurring amino acid
<220> FEATURE:
<221> NAME/KEY: VARIANT
<222> LOCATION: (263)..(265)
<223> OTHER INFORMATION: Xaa can be any naturally occurring amino acid
      or absent
<220> FEATURE:
<221> NAME/KEY: MISC_FEATURE
<222> LOCATION: (266)..(268)
<223> OTHER INFORMATION: Xaa can be any naturally occurring amino acid
<220> FEATURE:
<221> NAME/KEY: VARIANT
<222> LOCATION: (269)..(269)
<223> OTHER INFORMATION: Xaa can be any naturally occurring amino acid
      except arginine
<220> FEATURE:
<221> NAME/KEY: MISC_FEATURE
<222> LOCATION: (270)..(274)
<223> OTHER INFORMATION: Xaa can be any naturally occurring amino acid
<220> FEATURE:
<221> NAME/KEY: MISC_FEATURE
<222> LOCATION: (279)..(279)
<223> OTHER INFORMATION: Xaa can be any naturally occurring amino acid
<220> FEATURE:
<221> NAME/KEY: MISC_FEATURE
<222> LOCATION: (281)..(286)
<223> OTHER INFORMATION: Xaa can be any naturally occurring amino acid
<220> FEATURE:
<221> NAME/KEY: VARIANT
<222> LOCATION: (287)..(287)
<223> OTHER INFORMATION: Xaa can be any naturally occurring amino acid
      or absent
<220> FEATURE:
<221> NAME/KEY: MISC_FEATURE
<222> LOCATION: (288)..(288)
<223> OTHER INFORMATION: Xaa can be any naturally occurring amino acid
<220> FEATURE:
<221> NAME/KEY: MISC_FEATURE
<222> LOCATION: (290)..(291)
<223> OTHER INFORMATION: Xaa can be any naturally occurring amino acid
<220> FEATURE:
<221> NAME/KEY: MISC_FEATURE
<222> LOCATION: (293)..(293)
<223> OTHER INFORMATION: Xaa can be any naturally occurring amino acid
<220> FEATURE:
<221> NAME/KEY: VARIANT
<222> LOCATION: (297)..(297)
<223> OTHER INFORMATION: Xaa can be any naturally occurring amino acid
      except lysine
<220> FEATURE:
<221> NAME/KEY: VARIANT
<222> LOCATION: (301)..(301)
<223> OTHER INFORMATION: Xaa can be any naturally occurring amino acid
      except valine, threonine or isoleucine
<220> FEATURE:
<221> NAME/KEY: MISC_FEATURE
<222> LOCATION: (302)..(302)
<223> OTHER INFORMATION: Xaa can be any naturally occurring amino acid
<220> FEATURE:
<221> NAME/KEY: VARIANT
<222> LOCATION: (305)..(305)
<223> OTHER INFORMATION: Xaa can be any naturally occurring amino acid
      except proline
<220> FEATURE:
<221> NAME/KEY: MISC_FEATURE
<222> LOCATION: (306)..(306)
<223> OTHER INFORMATION: Xaa can be any naturally occurring amino acid
<220> FEATURE:
<221> NAME/KEY: MISC_FEATURE
<222> LOCATION: (308)..(311)
<223> OTHER INFORMATION: Xaa can be any naturally occurring amino acid
<220> FEATURE:
<221> NAME/KEY: MISC_FEATURE
<222> LOCATION: (316)..(316)
<223> OTHER INFORMATION: Xaa can be any naturally occurring amino acid
<220> FEATURE:
<221> NAME/KEY: MISC_FEATURE
```

```
<222> LOCATION: (319)..(321)
<223> OTHER INFORMATION: Xaa can be any naturally occurring amino acid
<220> FEATURE:
<221> NAME/KEY: MISC_FEATURE
<222> LOCATION: (323)..(325)
<223> OTHER INFORMATION: Xaa can be any naturally occurring amino acid
<220> FEATURE:
<221> NAME/KEY: MISC_FEATURE
<222> LOCATION: (327)..(331)
<223> OTHER INFORMATION: Xaa can be any naturally occurring amino acid
<220> FEATURE:
<221> NAME/KEY: VARIANT
<222> LOCATION: (334)..(334)
<223> OTHER INFORMATION: Xaa can be any naturally occurring amino acid
      except leucine
<220> FEATURE:
<221> NAME/KEY: MISC_FEATURE
<222> LOCATION: (336)..(336)
<223> OTHER INFORMATION: Xaa can be any naturally occurring amino acid
<220> FEATURE:
<221> NAME/KEY: MISC_FEATURE
<222> LOCATION: (349)..(350)
<223> OTHER INFORMATION: Xaa can be any naturally occurring amino acid
<220> FEATURE:
<221> NAME/KEY: MISC_FEATURE
<222> LOCATION: (352)..(353)
<223> OTHER INFORMATION: Xaa can be any naturally occurring amino acid
<220> FEATURE:
<221> NAME/KEY: MISC_FEATURE
<222> LOCATION: (356)..(356)
<223> OTHER INFORMATION: Xaa can be any naturally occurring amino acid
<220> FEATURE:
<221> NAME/KEY: MISC_FEATURE
<222> LOCATION: (358)..(359)
<223> OTHER INFORMATION: Xaa can be any naturally occurring amino acid
<220> FEATURE:
<221> NAME/KEY: VARIANT
<222> LOCATION: (360)..(360)
<223> OTHER INFORMATION: Xaa can be any naturally occurring amino acid
      except aspartate
<220> FEATURE:
<221> NAME/KEY: VARIANT
<222> LOCATION: (361)..(361)
<223> OTHER INFORMATION: Xaa can be any naturally occurring amino acid
      except threonine or isoleucine
<220> FEATURE:
<221> NAME/KEY: MISC_FEATURE
<222> LOCATION: (363)..(363)
<223> OTHER INFORMATION: Xaa can be any naturally occurring amino acid
<220> FEATURE:
<221> NAME/KEY: MISC_FEATURE
<222> LOCATION: (366)..(367)
<223> OTHER INFORMATION: Xaa can be any naturally occurring amino acid
<220> FEATURE:
<221> NAME/KEY: MISC_FEATURE
<222> LOCATION: (370)..(371)
<223> OTHER INFORMATION: Xaa can be any naturally occurring amino acid
<220> FEATURE:
<221> NAME/KEY: MISC_FEATURE
<222> LOCATION: (374)..(375)
<223> OTHER INFORMATION: Xaa can be any naturally occurring amino acid
<220> FEATURE:
<221> NAME/KEY: MISC_FEATURE
<222> LOCATION: (379)..(379)
<223> OTHER INFORMATION: Xaa can be any naturally occurring amino acid
<220> FEATURE:
<221> NAME/KEY: VARIANT
<222> LOCATION: (380)..(380)
<223> OTHER INFORMATION: Xaa can be any naturally occurring amino acid
      except methionine
<220> FEATURE:
<221> NAME/KEY: MISC_FEATURE
<222> LOCATION: (390)..(390)
<223> OTHER INFORMATION: Xaa can be any naturally occurring amino acid
<220> FEATURE:
<221> NAME/KEY: VARIANT
<222> LOCATION: (395)..(395)
<223> OTHER INFORMATION: Xaa can be any naturally occurring amino acid
      except leucine
```

```
<220> FEATURE:
<221> NAME/KEY: MISC_FEATURE
<222> LOCATION: (396)..(396)
<223> OTHER INFORMATION: Xaa can be any naturally occurring amino acid
<220> FEATURE:
<221> NAME/KEY: MISC_FEATURE
<222> LOCATION: (399)..(399)
<223> OTHER INFORMATION: Xaa can be any naturally occurring amino acid
<220> FEATURE:
<221> NAME/KEY: MISC_FEATURE
<222> LOCATION: (407)..(410)
<223> OTHER INFORMATION: Xaa can be any naturally occurring amino acid
<220> FEATURE:
<221> NAME/KEY: VARIANT
<222> LOCATION: (411)..(411)
<223> OTHER INFORMATION: Xaa can be any naturally occurring amino acid
      or absent
<220> FEATURE:
<221> NAME/KEY: MISC_FEATURE
<222> LOCATION: (413)..(413)
<223> OTHER INFORMATION: Xaa can be any naturally occurring amino acid
<220> FEATURE:
<221> NAME/KEY: MISC_FEATURE
<222> LOCATION: (415)..(415)
<223> OTHER INFORMATION: Xaa can be any naturally occurring amino acid
<220> FEATURE:
<221> NAME/KEY: VARIANT
<222> LOCATION: (416)..(416)
<223> OTHER INFORMATION: Xaa can be any naturally occurring amino acid
      except leucine
<220> FEATURE:
<221> NAME/KEY: MISC_FEATURE
<222> LOCATION: (418)..(419)
<223> OTHER INFORMATION: Xaa can be any naturally occurring amino acid
<220> FEATURE:
<221> NAME/KEY: MISC_FEATURE
<222> LOCATION: (428)..(428)
<223> OTHER INFORMATION: Xaa can be any naturally occurring amino acid
<220> FEATURE:
<221> NAME/KEY: VARIANT
<222> LOCATION: (429)..(429)
<223> OTHER INFORMATION: Xaa can be any naturally occurring amino acid
      except alanine
<220> FEATURE:
<221> NAME/KEY: VARIANT
<222> LOCATION: (430)..(430)
<223> OTHER INFORMATION: Xaa can be any naturally occurring amino acid
      except methionine
<220> FEATURE:
<221> NAME/KEY: MISC_FEATURE
<222> LOCATION: (431)..(431)
<223> OTHER INFORMATION: Xaa can be any naturally occurring amino acid
<220> FEATURE:
<221> NAME/KEY: MISC_FEATURE
<222> LOCATION: (433)..(433)
<223> OTHER INFORMATION: Xaa can be any naturally occurring amino acid
<220> FEATURE:
<221> NAME/KEY: VARIANT
<222> LOCATION: (435)..(435)
<223> OTHER INFORMATION: Xaa can be any naturally occurring amino acid
      except lysine
<220> FEATURE:
<221> NAME/KEY: MISC_FEATURE
<222> LOCATION: (436)..(436)
<223> OTHER INFORMATION: Xaa can be any naturally occurring amino acid
<220> FEATURE:
<221> NAME/KEY: MISC_FEATURE
<222> LOCATION: (438)..(441)
<223> OTHER INFORMATION: Xaa can be any naturally occurring amino acid
<220> FEATURE:
<221> NAME/KEY: VARIANT
<222> LOCATION: (442)..(442)
<223> OTHER INFORMATION: Xaa can be any naturally occurring amino acid
      except histidine
<220> FEATURE:
<221> NAME/KEY: MISC_FEATURE
<222> LOCATION: (443)..(446)
<223> OTHER INFORMATION: Xaa can be any naturally occurring amino acid
<220> FEATURE:
```

-continued

```
<221> NAME/KEY: MISC_FEATURE
<222> LOCATION: (448)..(449)
<223> OTHER INFORMATION: Xaa can be any naturally occurring amino acid
<220> FEATURE:
<221> NAME/KEY: VARIANT
<222> LOCATION: (451)..(451)
<223> OTHER INFORMATION: Xaa can be any naturally occurring amino acid
      except proline
<220> FEATURE:
<221> NAME/KEY: VARIANT
<222> LOCATION: (456)..(456)
<223> OTHER INFORMATION: Xaa can be any naturally occurring amino acid
      except histidine or
      cysteine
<220> FEATURE:
<221> NAME/KEY: MISC_FEATURE
<222> LOCATION: (457)..(457)
<223> OTHER INFORMATION: Xaa can be any naturally occurring amino acid
<220> FEATURE:
<221> NAME/KEY: VARIANT
<222> LOCATION: (461)..(461)
<223> OTHER INFORMATION: Xaa can be any naturally occurring amino acid
      except serine or
      aspartate
<220> FEATURE:
<221> NAME/KEY: MISC_FEATURE
<222> LOCATION: (469)..(470)
<223> OTHER INFORMATION: Xaa can be any naturally occurring amino acid
<220> FEATURE:
<221> NAME/KEY: VARIANT
<222> LOCATION: (473)..(473)
<223> OTHER INFORMATION: Xaa can be any naturally occurring amino acid
      except threonine
<220> FEATURE:
<221> NAME/KEY: MISC_FEATURE
<222> LOCATION: (477)..(477)
<223> OTHER INFORMATION: Xaa can be any naturally occurring amino acid
<220> FEATURE:
<221> NAME/KEY: MISC_FEATURE
<222> LOCATION: (481)..(481)
<223> OTHER INFORMATION: Xaa can be any naturally occurring amino acid
<220> FEATURE:
<221> NAME/KEY: VARIANT
<222> LOCATION: (484)..(484)
<223> OTHER INFORMATION: Xaa can be any naturally occurring amino acid
      except leucine
<220> FEATURE:
<221> NAME/KEY: MISC_FEATURE
<222> LOCATION: (485)..(487)
<223> OTHER INFORMATION: Xaa can be any naturally occurring amino acid
<220> FEATURE:
<221> NAME/KEY: MISC_FEATURE
<222> LOCATION: (492)..(492)
<223> OTHER INFORMATION: Xaa can be any naturally occurring amino acid
<220> FEATURE:
<221> NAME/KEY: MISC_FEATURE
<222> LOCATION: (494)..(494)
<223> OTHER INFORMATION: Xaa can be any naturally occurring amino acid
<220> FEATURE:
<221> NAME/KEY: VARIANT
<222> LOCATION: (496)..(496)
<223> OTHER INFORMATION: Xaa can be any naturally occurring amino acid
      except
      phenylalanine
<220> FEATURE:
<221> NAME/KEY: VARIANT
<222> LOCATION: (497)..(497)
<223> OTHER INFORMATION: Xaa can be any naturally occurring amino acid
      except arginine
<220> FEATURE:
<221> NAME/KEY: VARIANT
<222> LOCATION: (498)..(501)
<223> OTHER INFORMATION: Xaa can be any naturally occurring amino acid
      or absent
<220> FEATURE:
<221> NAME/KEY: MISC_FEATURE
<222> LOCATION: (502)..(507)
<223> OTHER INFORMATION: Xaa can be any naturally occurring amino acid
<220> FEATURE:
```

```
<221> NAME/KEY: MISC_FEATURE
<222> LOCATION: (509)..(516)
<223> OTHER INFORMATION: Xaa can be any naturally occurring amino acid
<220> FEATURE:
<221> NAME/KEY: VARIANT
<222> LOCATION: (517)..(520)
<223> OTHER INFORMATION: Xaa can be any naturally occurring amino acid
      or absent
<220> FEATURE:
<221> NAME/KEY: MISC_FEATURE
<222> LOCATION: (521)..(524)
<223> OTHER INFORMATION: Xaa can be any naturally occurring amino acid
<220> FEATURE:
<221> NAME/KEY: MISC_FEATURE
<222> LOCATION: (526)..(532)
<223> OTHER INFORMATION: Xaa can be any naturally occurring amino acid
<220> FEATURE:
<221> NAME/KEY: MISC_FEATURE
<222> LOCATION: (534)..(534)
<223> OTHER INFORMATION: Xaa can be any naturally occurring amino acid
<220> FEATURE:
<221> NAME/KEY: VARIANT
<222> LOCATION: (535)..(541)
<223> OTHER INFORMATION: Xaa can be any naturally occurring amino acid
      or absent

<400> SEQUENCE: 15

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Glu Xaa Xaa Pro Xaa
                20                  25                  30

Xaa Trp Xaa Xaa Xaa Ala Xaa Xaa Xaa Leu Xaa Xaa Ala Xaa Xaa Leu
        35                  40                  45

Gln Xaa Xaa Xaa Xaa Xaa Xaa Lys Asn Xaa Ile Xaa Phe Leu Gly
50                  55                  60

Asp Gly Xaa Gly Val Xaa Thr Val Thr Ala Xaa Arg Ile Leu Lys Gly
65                  70                  75                  80

Gln Xaa Xaa Xaa Xaa Xaa Gly Xaa Glu Xaa Xaa Leu Xaa Met Asp Xaa
                85                  90                  95

Phe Pro Xaa Xaa Ala Leu Ser Lys Thr Tyr Xaa Xaa Xaa Xaa Xaa Val
            100                 105                 110

Pro Asp Ser Xaa Xaa Thr Ala Thr Ala Tyr Leu Cys Gly Val Lys Xaa
                115                 120                 125

Asn Xaa Xaa Thr Xaa Gly Xaa Ser Ala Ala Xaa Xaa Xaa Xaa Xaa Cys
    130                 135                 140

Asn Thr Thr Xaa Gly Asn Glu Val Xaa Ser Xaa Xaa Xaa Xaa Ala Lys
145                 150                 155                 160

Xaa Xaa Gly Lys Ser Val Gly Xaa Val Thr Thr Arg Val Xaa His
            165                 170                 175

Ala Xaa Pro Xaa Xaa Xaa Tyr Ala His Xaa Xaa Xaa Arg Xaa Trp Tyr
        180                 185                 190

Ser Asp Xaa Xaa Xaa Pro Xaa Xaa Ala Xaa Xaa Xaa Gly Cys Xaa Asp
        195                 200                 205

Ile Ala Xaa Gln Leu Xaa Xaa Asn Xaa Xaa Asp Ile Xaa Val Ile Xaa
        210                 215                 220

Gly Gly Gly Arg Lys Tyr Met Xaa Xaa Xaa Xaa Xaa Asp Xaa Glu
225                 230                 235                 240

Tyr Xaa Xaa Asp Xaa Xaa Xaa Xaa Gly Xaa Arg Leu Asp Gly Xaa Xaa
            245                 250                 255

Leu Xaa Xaa Xaa Trp Xaa Xaa Xaa Xaa Xaa Xaa Xaa Xaa Xaa
        260                 265                 270
```

```
Xaa Xaa Trp Asn Arg Thr Xaa Leu Xaa Xaa Xaa Xaa Xaa Xaa
        275                 280                 285

Val Xaa Xaa Leu Xaa Gly Leu Phe Xaa Pro Gly Asp Xaa Xaa Tyr Glu
    290                 295                 300

Xaa Xaa Arg Xaa Xaa Xaa Xaa Asp Pro Ser Leu Xaa Glu Met Xaa Xaa
305                 310                 315                 320

Xaa Ala Xaa Xaa Xaa Leu Xaa Xaa Xaa Xaa Gly Phe Xaa Leu Xaa
            325                 330                 335

Val Glu Gly Gly Arg Ile Asp His Gly His His Glu Xaa Xaa Ala Xaa
    340                 345                 350

Xaa Ala Leu Xaa Glu Xaa Xaa Xaa Xaa Asp Xaa Ala Ile Xaa Xaa Ala
        355                 360                 365

Gly Xaa Xaa Thr Ser Xaa Xaa Asp Thr Leu Xaa Xaa Val Thr Ala Asp
    370                 375                 380

His Ser His Val Phe Xaa Phe Gly Gly Tyr Xaa Xaa Arg Gly Xaa Ser
385                 390                 395                 400

Ile Phe Gly Leu Ala Pro Xaa Xaa Xaa Xaa Asp Xaa Lys Xaa Xaa
                405                 410                 415

Thr Xaa Xaa Leu Tyr Gly Asn Gly Pro Gly Tyr Xaa Xaa Xaa Xaa Gly
    420                 425                 430

Xaa Arg Xaa Xaa Val Xaa Xaa Xaa Xaa Xaa Xaa Xaa Tyr Xaa
        435                 440                 445

Xaa Gln Xaa Ala Val Pro Leu Xaa Xaa Glu Thr His Xaa Gly Glu Asp
    450                 455                 460

Val Ala Val Phe Xaa Xaa Gly Pro Xaa Ala His Leu Xaa His Gly Val
465                 470                 475                 480

Xaa Glu Gln Xaa Xaa Xaa Xaa His Val Met Ala Xaa Ala Xaa Cys Xaa
                485                 490                 495

Xaa Xaa Xaa Xaa Xaa Xaa Xaa Xaa Xaa Ala Xaa Xaa Xaa Xaa
            500                 505                 510

Xaa Xaa Xaa Xaa Xaa Xaa Xaa Xaa Xaa Leu Xaa Xaa Xaa
            515                 520                 525

Xaa Xaa Xaa Xaa Leu Xaa Xaa Xaa Xaa Xaa Xaa Xaa Xaa
        530                 535                 540

<210> SEQ ID NO 16
<211> LENGTH: 524
<212> TYPE: PRT
<213> ORGANISM: Artificial Sequence
<220> FEATURE:
<223> OTHER INFORMATION: Consensus ALP
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (14)..(16)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid
<220> FEATURE:
```

```
<221> NAME/KEY: MISC_FEATURE
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: Xaa can be any naturally occurring amino acid
<220> FEATURE:
<221> NAME/KEY: MISC_FEATURE
<222> LOCATION: (39)..(39)
<223> OTHER INFORMATION: Xaa can be any naturally occurring amino acid
<220> FEATURE:
<221> NAME/KEY: MISC_FEATURE
<222> LOCATION: (42)..(42)
<223> OTHER INFORMATION: Xaa can be any naturally occurring amino acid
<220> FEATURE:
<221> NAME/KEY: MISC_FEATURE
<222> LOCATION: (45)..(45)
<223> OTHER INFORMATION: Xaa can be any naturally occurring amino acid
<220> FEATURE:
<221> NAME/KEY: VARIANT
<222> LOCATION: (51)..(51)
<223> OTHER INFORMATION: Xaa can be any naturally occurring amino acid
      except serine or valine
<220> FEATURE:
<221> NAME/KEY: MISC_FEATURE
<222> LOCATION: (54)..(54)
<223> OTHER INFORMATION: Xaa can be any naturally occurring amino acid
<220> FEATURE:
<221> NAME/KEY: MISC_FEATURE
<222> LOCATION: (70)..(70)
<223> OTHER INFORMATION: Xaa can be any naturally occurring amino acid
<220> FEATURE:
<221> NAME/KEY: MISC_FEATURE
<222> LOCATION: (80)..(81)
<223> OTHER INFORMATION: Xaa can be any naturally occurring amino acid
<220> FEATURE:
<221> NAME/KEY: MISC_FEATURE
<222> LOCATION: (86)..(86)
<223> OTHER INFORMATION: Xaa can be any naturally occurring amino acid
<220> FEATURE:
<221> NAME/KEY: MISC_FEATURE
<222> LOCATION: (94)..(94)
<223> OTHER INFORMATION: Xaa can be any naturally occurring amino acid
<220> FEATURE:
<221> NAME/KEY: MISC_FEATURE
<222> LOCATION: (135)..(135)
<223> OTHER INFORMATION: Xaa can be any naturally occurring amino acid
<220> FEATURE:
<221> NAME/KEY: MISC_FEATURE
<222> LOCATION: (137)..(138)
<223> OTHER INFORMATION: Xaa can be any naturally occurring amino acid
<220> FEATURE:
<221> NAME/KEY: MISC_FEATURE
<222> LOCATION: (157)..(157)
<223> OTHER INFORMATION: Xaa can be any naturally occurring amino acid
<220> FEATURE:
<221> NAME/KEY: VARIANT
<222> LOCATION: (177)..(177)
<223> OTHER INFORMATION: Xaa can be any naturally occurring amino acid
      except threonine
<220> FEATURE:
<221> NAME/KEY: VARIANT
<222> LOCATION: (212)..(212)
<223> OTHER INFORMATION: Xaa can be any naturally occurring amino acid
      except phenylalanine
<220> FEATURE:
<221> NAME/KEY: MISC_FEATURE
<222> LOCATION: (213)..(213)
<223> OTHER INFORMATION: Xaa can be any naturally occurring amino acid
<220> FEATURE:
<221> NAME/KEY: MISC_FEATURE
<222> LOCATION: (216)..(216)
<223> OTHER INFORMATION: Xaa can be any naturally occurring amino acid
<220> FEATURE:
```

```
<221> NAME/KEY: MISC_FEATURE
<222> LOCATION: (227)..(227)
<223> OTHER INFORMATION: Xaa can be any naturally occurring amino acid
<220> FEATURE:
<221> NAME/KEY: MISC_FEATURE
<222> LOCATION: (231)..(231)
<223> OTHER INFORMATION: Xaa can be any naturally occurring amino acid
<220> FEATURE:
<221> NAME/KEY: MISC_FEATURE
<222> LOCATION: (238)..(238)
<223> OTHER INFORMATION: Xaa can be any naturally occurring amino acid
<220> FEATURE:
<221> NAME/KEY: MISC_FEATURE
<222> LOCATION: (242)..(243)
<223> OTHER INFORMATION: Xaa can be any naturally occurring amino acid
<220> FEATURE:
<221> NAME/KEY: MISC_FEATURE
<222> LOCATION: (245)..(245)
<223> OTHER INFORMATION: Xaa can be any naturally occurring amino acid
<220> FEATURE:
<221> NAME/KEY: MISC_FEATURE
<222> LOCATION: (251)..(251)
<223> OTHER INFORMATION: Xaa can be any naturally occurring amino acid
<220> FEATURE:
<221> NAME/KEY: MISC_FEATURE
<222> LOCATION: (253)..(255)
<223> OTHER INFORMATION: Xaa can be any naturally occurring amino acid
<220> FEATURE:
<221> NAME/KEY: MISC_FEATURE
<222> LOCATION: (258)..(258)
<223> OTHER INFORMATION: Xaa can be any naturally occurring amino acid
<220> FEATURE:
<221> NAME/KEY: MISC_FEATURE
<222> LOCATION: (262)..(263)
<223> OTHER INFORMATION: Xaa can be any naturally occurring amino acid
<220> FEATURE:
<221> NAME/KEY: MISC_FEATURE
<222> LOCATION: (268)..(269)
<223> OTHER INFORMATION: Xaa can be any naturally occurring amino acid
<220> FEATURE:
<221> NAME/KEY: MISC_FEATURE
<222> LOCATION: (274)..(274)
<223> OTHER INFORMATION: Xaa can be any naturally occurring amino acid
<220> FEATURE:
<221> NAME/KEY: MISC_FEATURE
<222> LOCATION: (277)..(277)
<223> OTHER INFORMATION: Xaa can be any naturally occurring amino acid
<220> FEATURE:
<221> NAME/KEY: MISC_FEATURE
<222> LOCATION: (281)..(282)
<223> OTHER INFORMATION: Xaa can be any naturally occurring amino acid
<220> FEATURE:
<221> NAME/KEY: VARIANT
<222> LOCATION: (291)..(291)
<223> OTHER INFORMATION: Xaa can be any naturally occurring amino acid
    except lysine
<220> FEATURE:
<221> NAME/KEY: MISC_FEATURE
<222> LOCATION: (303)..(304)
<223> OTHER INFORMATION: Xaa can be any naturally occurring amino acid
<220> FEATURE:
<221> NAME/KEY: MISC_FEATURE
<222> LOCATION: (314)..(315)
<223> OTHER INFORMATION: Xaa can be any naturally occurring amino acid
<220> FEATURE:
<221> NAME/KEY: MISC_FEATURE
<222> LOCATION: (317)..(318)
<223> OTHER INFORMATION: Xaa can be any naturally occurring amino acid
<220> FEATURE:
<221> NAME/KEY: MISC_FEATURE
<222> LOCATION: (321)..(321)
<223> OTHER INFORMATION: Xaa can be any naturally occurring amino acid
<220> FEATURE:
<221> NAME/KEY: MISC_FEATURE
<222> LOCATION: (323)..(325)
<223> OTHER INFORMATION: Xaa can be any naturally occurring amino acid
<220> FEATURE:
<221> NAME/KEY: MISC_FEATURE
<222> LOCATION: (357)..(357)
```

```
<223> OTHER INFORMATION: Xaa can be any naturally occurring amino acid
<220> FEATURE:
<221> NAME/KEY: MISC_FEATURE
<222> LOCATION: (361)..(361)
<223> OTHER INFORMATION: Xaa can be any naturally occurring amino acid
<220> FEATURE:
<221> NAME/KEY: MISC_FEATURE
<222> LOCATION: (364)..(365)
<223> OTHER INFORMATION: Xaa can be any naturally occurring amino acid
<220> FEATURE:
<221> NAME/KEY: MISC_FEATURE
<222> LOCATION: (368)..(369)
<223> OTHER INFORMATION: Xaa can be any naturally occurring amino acid
<220> FEATURE:
<221> NAME/KEY: VARIANT
<222> LOCATION: (374)..(374)
<223> OTHER INFORMATION: Xaa can be any naturally occurring amino acid
      except methionine
<220> FEATURE:
<221> NAME/KEY: MISC_FEATURE
<222> LOCATION: (402)..(402)
<223> OTHER INFORMATION: Xaa can be any naturally occurring amino acid
<220> FEATURE:
<221> NAME/KEY: MISC_FEATURE
<222> LOCATION: (412)..(412)
<223> OTHER INFORMATION: Xaa can be any naturally occurring amino acid
<220> FEATURE:
<221> NAME/KEY: MISC_FEATURE
<222> LOCATION: (425)..(425)
<223> OTHER INFORMATION: Xaa can be any naturally occurring amino acid
<220> FEATURE:
<221> NAME/KEY: MISC_FEATURE
<222> LOCATION: (463)..(463)
<223> OTHER INFORMATION: Xaa can be any naturally occurring amino acid
<220> FEATURE:
<221> NAME/KEY: MISC_FEATURE
<222> LOCATION: (480)..(480)
<223> OTHER INFORMATION: Xaa can be any naturally occurring amino acid
<220> FEATURE:
<221> NAME/KEY: MISC_FEATURE
<222> LOCATION: (488)..(488)
<223> OTHER INFORMATION: Xaa can be any naturally occurring amino acid
<220> FEATURE:
<221> NAME/KEY: MISC_FEATURE
<222> LOCATION: (494)..(495)
<223> OTHER INFORMATION: Xaa can be any naturally occurring amino acid
<220> FEATURE:
<221> NAME/KEY: MISC_FEATURE
<222> LOCATION: (499)..(499)
<223> OTHER INFORMATION: Xaa can be any naturally occurring amino acid
<220> FEATURE:
<221> NAME/KEY: MISC_FEATURE
<222> LOCATION: (501)..(501)
<223> OTHER INFORMATION: Xaa can be any naturally occurring amino acid
<220> FEATURE:
<221> NAME/KEY: MISC_FEATURE
<222> LOCATION: (503)..(508)
<223> OTHER INFORMATION: Xaa can be any naturally occurring amino acid
<220> FEATURE:
<221> NAME/KEY: MISC_FEATURE
<222> LOCATION: (510)..(510)
<223> OTHER INFORMATION: Xaa can be any naturally occurring amino acid
<220> FEATURE:
<221> NAME/KEY: MISC_FEATURE
<222> LOCATION: (512)..(512)
<223> OTHER INFORMATION: Xaa can be any naturally occurring amino acid
<220> FEATURE:
<221> NAME/KEY: MISC_FEATURE
<222> LOCATION: (514)..(514)
<223> OTHER INFORMATION: Xaa can be any naturally occurring amino acid
<220> FEATURE:
<221> NAME/KEY: MISC_FEATURE
<222> LOCATION: (517)..(522)
<223> OTHER INFORMATION: Xaa can be any naturally occurring amino acid

<400> SEQUENCE: 16

Met Ile Xaa Pro Phe Leu Xaa Leu Ala Ile Gly Thr Cys Xaa Xaa Xaa
1               5                   10                  15
```

```
Ser Xaa Val Pro Glu Lys Glu Xaa Asp Pro Xaa Tyr Trp Arg Xaa Gln
         20                  25                  30

Ala Gln Xaa Thr Leu Lys Xaa Ala Leu Xaa Leu Gln Xaa Leu Asn Thr
             35                  40                  45

Asn Val Xaa Lys Asn Xaa Ile Met Phe Leu Gly Asp Gly Met Gly Val
 50                  55                  60

Ser Thr Val Thr Ala Xaa Arg Ile Leu Lys Gly Gln Leu His His Xaa
 65                  70                  75                  80

Xaa Gly Glu Glu Thr Xaa Leu Glu Met Asp Lys Phe Pro Xaa Val Ala
                 85                  90                  95

Leu Ser Lys Thr Tyr Asn Thr Asn Ala Gln Val Pro Ser Ala Gly
             100                 105                 110

Thr Ala Thr Ala Tyr Leu Cys Gly Val Lys Ala Asn Glu Gly Thr Val
             115                 120                 125

Gly Val Ser Ala Ala Thr Xaa Arg Xaa Xaa Cys Asn Thr Thr Gln Gly
 130                 135                 140

Asn Glu Val Thr Ser Ile Leu Arg Trp Ala Lys Asp Xaa Gly Lys Ser
145                 150                 155                 160

Val Gly Ile Val Thr Thr Thr Arg Val Asn His Ala Thr Pro Ser Ala
                 165                 170                 175

Xaa Tyr Ala His Ser Ala Asp Arg Asp Trp Tyr Ser Asp Asn Glu Met
             180                 185                 190

Pro Pro Glu Ala Leu Ser Gln Gly Cys Lys Asp Ile Ala Tyr Gln Leu
             195                 200                 205

Met His Asn Xaa Xaa Asp Ile Xaa Val Ile Met Gly Gly Gly Arg Lys
             210                 215                 220

Tyr Met Xaa Pro Lys Asn Xaa Thr Asp Val Glu Tyr Glu Xaa Asp Glu
225                 230                 235                 240

Lys Xaa Xaa Gly Xaa Arg Leu Asp Gly Leu Xaa Leu Xaa Xaa Xaa Trp
             245                 250                 255

Lys Xaa Phe Lys Pro Xaa Xaa Lys His Ser His Xaa Xaa Trp Asn Arg
             260                 265                 270

Thr Xaa Leu Leu Xaa Leu Asp Pro Xaa Xaa Val Asp Tyr Leu Leu Gly
             275                 280                 285

Leu Phe Xaa Pro Gly Asp Met Gln Tyr Glu Leu Asn Arg Asn Xaa Xaa
             290                 295                 300

Thr Asp Pro Ser Leu Ser Glu Met Val Xaa Xaa Ala Xaa Xaa Ile Leu
305                 310                 315                 320

Xaa Lys Xaa Xaa Xaa Gly Phe Phe Leu Leu Val Glu Gly Gly Arg Ile
             325                 330                 335

Asp His Gly His His Glu Gly Lys Ala Lys Gln Ala Leu His Glu Ala
             340                 345                 350

Val Glu Met Asp Xaa Ala Ile Gly Xaa Ala Gly Xaa Xaa Thr Ser Xaa
             355                 360                 365

Xaa Asp Thr Leu Thr Xaa Val Thr Ala Asp His Ser His Val Phe Thr
             370                 375                 380

Phe Gly Gly Tyr Thr Pro Arg Gly Asn Ser Ile Phe Gly Leu Ala Pro
385                 390                 395                 400

Met Xaa Ser Asp Thr Asp Lys Lys Pro Phe Thr Xaa Ile Leu Tyr Gly
             405                 410                 415

Asn Gly Pro Gly Tyr Lys Val Val Xaa Gly Glu Arg Glu Asn Val Ser
             420                 425                 430
```

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Xaa Lys
    450                 455                 460

Gly Pro Met Ala His Leu Leu His Gly Val His Glu Gln Asn Tyr Xaa
465                 470                 475                 480

Pro His Val Met Ala Tyr Ala Xaa Cys Ile Gly Ala Asn Xaa Xaa His
                485                 490                 495

Cys Ala Xaa Ala Xaa Ser Xaa Xaa Xaa Xaa Xaa Gly Xaa Leu Xaa
            500                 505                 510

Leu Xaa Leu Ala Xaa Xaa Xaa Xaa Xaa Xaa Leu Phe
    515                 520

<210> SEQ ID NO 17
<211> LENGTH: 2193
<212> TYPE: DNA
<213> ORGANISM: Artificial Sequence
<220> FEATURE:
<223> OTHER INFORMATION: hsTNALP-Fc

<400> SEQUENCE: 17

| | | | | | | |
|---|---|---|---|---|---|---|
| atggtttcac | cattcttagt | actggccatt | ggcacctgcc | ttactaactc | cttagtgcca | 60 |
| gagaaagaga | aagaccccaa | gtactggcga | gaccaagcgc | aagagacact | gaaatatgcc | 120 |
| ctggagcttc | agaagctcaa | caccaacgtg | gctaagaatg | tcatcatgtt | cctgggagat | 180 |
| gggatgggtg | tctccacagt | gacggctgcc | cgcatcctca | agggtcagct | ccaccacaac | 240 |
| cctggggagg | agaccaggct | ggagatggac | aagttcccct | tcgtggccct | ctccaagacg | 300 |
| tacaacacca | atgcccaggt | ccctgacagc | gccggcaccg | ccaccgccta | cctgtgtggg | 360 |
| gtgaaggcca | atgagggcac | cgtggggta | agcgcagcca | ctgagcgttc | cggtgcaac | 420 |
| accacccagg | ggaacgaggt | cacctccatc | ctgcgctggg | ccaaggacgc | tgggaaatct | 480 |
| gtgggcattg | tgaccaccac | gagagtgaac | catgccaccc | cagcgccgc | ctacgcccac | 540 |
| tcggctgacc | gggactggta | ctcagacaac | gagatgcccc | ctgaggcctt | gagccagggc | 600 |
| tgtaaggaca | tcgcctacca | gctcatgcat | aacatcaggg | acattgacgt | gatcatgggg | 660 |
| ggtggccgga | atacatgta | ccccaagaat | aaaactgatg | tggagtatga | gagtgacgag | 720 |
| aaagccaggg | gcacgaggct | ggacggcctg | gacctcgttg | acacctggaa | gagcttcaaa | 780 |
| ccgagataca | agcactccca | cttcatctgg | aaccgcacgg | aactcctgac | ccttgacccc | 840 |
| cacaatgtgg | actacctatt | gggtctcttc | gagccagggg | acatgcagta | cgagctgaac | 900 |
| aggaacaacg | tgacggaccc | gtcactctcc | gagatggtgg | tggtggccat | ccagatcctg | 960 |
| cggaagaacc | ccaaaggctt | cttcttgctg | gtggaaggag | gcagaattga | ccacgggcac | 1020 |
| catgaaggaa | aagccaagca | ggccctgcat | gaggcggtgg | agatggaccg | ggccatcggg | 1080 |
| caggcaggca | gcttgacctc | ctcggaagac | actctgaccg | tggtcactgc | ggaccattcc | 1140 |
| cacgtcttca | catttggtgg | atacaccccc | cgtggcaact | ctatctttgg | tctgccccc | 1200 |
| atgctgagtg | acacagacaa | gaagccctc | actgccatcc | tgtatggcaa | tgggcctggc | 1260 |
| tacaaggtgg | tggcggtga | acgagagaat | gtctccatgg | tggactatgc | tcacaacaac | 1320 |
| taccaggcgc | agtctgctgt | gccctgcgc | acgagaccc | acggcgggga | ggacgtggcc | 1380 |
| gtcttctcca | agggccccat | ggcgcacctg | ctgcacggcg | tccacgagca | gaactacgtc | 1440 |
| ccccacgtga | tggcgtatgc | agcctgcatc | ggggccaacc | tcggccactg | tgctcctgcc | 1500 |
| agctcgctta | aggacaaaac | tcacacatgc | ccaccgtgcc | cagcacctga | actcctgggg | 1560 |

```
ggaccgtcag tcttcctctt cccccaaaa cccaaggaca ccctcatgat ctcccggacc    1620
cctgaggtca catgcgtggt ggtggacgtg agccacgaag accctgaggt caagttcaac    1680
tggtacgtgg acggcgtgga ggtgcataat gccaagacaa agccgcggga ggagcagtac    1740
aacagcacgt accgtgtggt cagcgtcctc accgtcctgc accaggactg gctgaatggc    1800
aaggagtaca agtgcaaggt ctccaacaaa gccctcccag cccccatcga gaaaaccatc    1860
tccaaagcca aagggcagcc ccgagaacca caggtgtaca ccctgccccc atcccgggag    1920
gagatgacca gaaccaggt cagcctgacc tgcctggtca aaggcttcta tcccagcgac     1980
atcgccgtgg agtgggagag caatgggcag ccggagaaca actacaagac cacgcctccc    2040
gtgctggact ccgacggctc cttcttcctc tatagcaagc tcaccgtgga caagagcagg    2100
tggcagcagg ggaacgtctt ctcatgctcc gtgatgcatg aggctctgca caaccactac    2160
acgcagaaga gcctctccct gtctccgggt aaa                                 2193

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
gtccgtgggc attgtgacta ccac                                           24

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tgctgctcca ctcacgtcg                                                 19
```